United States Patent
Polakis et al.

(10) Patent No.: US 9,815,905 B2
(45) Date of Patent: *Nov. 14, 2017

(54) COMPOSITIONS AND METHODS FOR THE DIAGNOSIS AND TREATMENT OF TUMOR

(71) Applicant: Genentech, Inc., South San Francisco, CA (US)

(72) Inventors: Paul Polakis, Mill Valley, CA (US); Jyoti Asundi, Foster City, CA (US); Ron Firestein, South San Francisco, CA (US); Robert F. Kelley, San Bruno, CA (US); Krista McCutcheon, Burlingame, CA (US)

(73) Assignee: Genentech, Inc., South San Francisco, CA (US)

( * ) Notice: Subject to any disclaimer, the term of this patent is extended or adjusted under 35 U.S.C. 154(b) by 103 days.

This patent is subject to a terminal disclaimer.

(21) Appl. No.: 14/500,079

(22) Filed: Sep. 29, 2014

(65) Prior Publication Data

US 2015/0023871 A1    Jan. 22, 2015

Related U.S. Application Data

(63) Continuation of application No. 13/031,848, filed on Feb. 22, 2011, now Pat. No. 8,877,897.

(60) Provisional application No. 61/308,791, filed on Feb. 26, 2010, provisional application No. 61/307,338, filed on Feb. 23, 2010.

(51) Int. Cl.
| | |
|---|---|
| *A61K 31/40* | (2006.01) |
| *C07K 16/30* | (2006.01) |
| *A61K 47/48* | (2006.01) |
| *A61K 39/395* | (2006.01) |
| *A61K 51/10* | (2006.01) |
| *G01N 33/68* | (2006.01) |
| *A61K 39/00* | (2006.01) |

(52) U.S. Cl.
CPC ............ *C07K 16/30* (2013.01); *A61K 31/40* (2013.01); *A61K 39/39558* (2013.01); *A61K 47/48384* (2013.01); *A61K 47/48569* (2013.01); *A61K 51/1045* (2013.01); *G01N 33/6854* (2013.01); *A61K 2039/505* (2013.01); *C07K 2317/24* (2013.01); *C07K 2317/55* (2013.01); *C07K 2317/56* (2013.01); *C07K 2317/732* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| | | |
|---|---|---|
| 5,773,223 A | 6/1998 | Shyamala et al. |
| 6,214,345 B1 | 4/2001 | Firestone et al. |
| 7,303,749 B1 | 12/2007 | Chari et al. |
| 7,498,298 B2 | 3/2009 | Doronina et al. |
| 7,521,541 B2 | 4/2009 | Eigenbrot et al. |
| 7,601,354 B2 | 10/2009 | Chari et al. |
| 7,659,241 B2 | 2/2010 | Senter et al. |
| 7,745,394 B2 | 6/2010 | Doronina et al. |
| 7,829,531 B2 | 11/2010 | Senter et al. |
| 7,851,437 B2 | 12/2010 | Senter et al. |
| 7,855,275 B2 | 12/2010 | Eigenbrot et al. |
| 7,964,566 B2 | 6/2011 | Doronina et al. |
| 7,964,567 B2 | 6/2011 | Doronina et al. |
| 7,994,135 B2 | 8/2011 | Doronina et al. |
| 8,088,387 B2 | 1/2012 | Steeves et al. |
| 8,142,784 B2 | 3/2012 | Ebens et al. |
| 8,198,417 B2 | 6/2012 | Steeves et al. |
| 8,309,300 B2 | 11/2012 | Junutula et al. |
| 8,557,780 B2 | 10/2013 | Doronina et al. |
| 2006/0094676 A1 | 5/2006 | Lahav et al. |
| 2007/0269442 A1 | 11/2007 | Webber et al. |
| 2008/0075712 A1 | 3/2008 | Hattori et al. |
| 2012/0148610 A1 | 6/2012 | Doronina et al. |

FOREIGN PATENT DOCUMENTS

| | | |
|---|---|---|
| EP | 522868 A1 | 1/1993 |
| WO | 00/67024 | 11/2000 |
| WO | 01/00198 | 1/2001 |
| WO | 01/98351 A2 | 12/2001 |
| WO | 02/061087 A2 | 8/2002 |
| WO | 03/016494 A2 | 2/2003 |
| WO | 03/025138 A2 | 3/2003 |
| WO | 2004/048938 A2 | 6/2004 |
| WO | 2005/081711 A2 | 9/2005 |
| WO | 2005/082023 | 9/2005 |
| WO | 2005/095972 | 10/2005 |
| WO | 2005/117986 A2 | 12/2005 |
| WO | 2006/034488 A2 | 3/2006 |
| WO | 2006/034488 A3 | 3/2006 |
| WO | 2006/060533 | 6/2006 |
| WO | 2007/064345 | 6/2007 |

(Continued)

OTHER PUBLICATIONS

Elshourbagy et al., "Molecular Characterization and Regulation of the Human Endothelin Receptors" Journal of Biological Chemistry 268(6):3873-3879 (Feb. 25, 1993).
(Written Opinion for PCT/US2011/025642).
Asundi et al., "An Antibody-Drug Conjugate Targeting the Endothelin B Receptor for the Treatment of Melanoma" Clinical Cancer Research, The American Association for Cancer Research 17(5):965-975 (Mar. 1, 2011).
Bagnato et al., "Endothelin Receptor Blockade Inhibits Proliferation of Kaposi's Sarcoma Cells" The American Journal of Pathology 158(3):841-847 (Mar. 2001).

(Continued)

*Primary Examiner* — Laura B Goddard
*Assistant Examiner* — Meera Natarajan
(74) *Attorney, Agent, or Firm* — Sheridan Ross P.C.

(57) ABSTRACT

The present invention is directed to compositions of matter useful for the diagnosis and treatment of tumor in mammals and to methods of using those compositions of matter for the same.

11 Claims, 9 Drawing Sheets

(56) References Cited

FOREIGN PATENT DOCUMENTS

| WO | 2007/100385 | 9/2007 |
| --- | --- | --- |
| WO | 2009/012256 | 1/2009 |
| WO | 2010/009124 | 1/2010 |
| WO | 2010/099273 | 9/2010 |
| WO | 2011/056983 | 5/2011 |
| WO | 2011/106297 | 9/2011 |
| WO | 2011/156328 | 12/2011 |
| WO | 2012/074757 | 6/2012 |

OTHER PUBLICATIONS

Casset et al., Biochem. Biophys. Res. Commun. (Examiner cited), 307(1):198-205 ( 2003).

Chen et al., "Selection and analysis of an optimized anti-VEGF antibody: crystal structure of an affinity-matured Fab in complex with antigen" J Mol Biol. 293(4):865-81 ( 1999).

De Pascalis et al. et al., J Immunol 169:3076-3084 ( 2002).

Demunter et al., "Expression of the endothelin-B receptor in pigment cell lesions of the skin: evidence for its role as tumor progession marker in malignant melanoma" Virchows Archiv :438(5):485-491 (May 1, 2001).

Grantcharova et al., "The Extracellular N Terminus of the Endothelin B (ETb) Receptor is Cleaved by a Metalloprotease in an Agonist-dependent Process" J Biol Chem 277(46):43933-43941 (Nov. 15, 2002).

Hardwick et al., "Identification of Biomarkers for Tumor Endothelial Cell Proliferation through Gene Expression Profiling" Molecular Cancer Therapeutics 4(3):413-425 (Mar. 2005).

Lahav et al., "An Endothelin Receptor B Antagonist Inhibits Growth and Induces Cell Death in Human Melanoma Cells in Vitro and in Vivo" Proceedings of the National Academy of Sciences of the United States, National Academy of Science 96(20):11496-11500 (Sep. 1, 1999).

Lamminmak et al., "Crystal structure of a recombinant anti-estradiol Fab fragment in complex with 17β-estradiol" Journal of Biological Chemistry 276(39):36687-36694 (Sep. 28, 2001).

MacCallum et al., "Antibody-antigen interactions: contact analysis and binding site topography" J Mol Biol. 262(5):732-45 ( 1996).

Nakamuta et al. et al., "Cloning and sequence analysis of a cDNA encoding human i non-selective type of endothelin receptor" Biochem Bioph Res Co 177(1):34-9 ( 1991).

Ogawa et al. et al., "Jul 15;178(1):. Molecular cloning of a non-isopeptide-selective human endothelin receptor" Biochem Bioph Res Co 178(1):248-55 ( 1991).

Other Database, EBI Accession No. UNIPROT:P24530, Mar. 1, 1992.

Padlan et al., "Structure of an antibody-antigen complex: crystal structure of the HyHEL-10 Fab-lysozyme complex" Proc. Natl. Acad. Sci. 86:5938-5942 (Aug. 1989).

Rosano et al., "Endothelin-B Receptor Blockade Inhibits Molecular Effectors of Melanoma Cell Progression" Journal of Cardiovascular Pharmacology, Raven Press 44( SUPPL 1):S136-S139 (Nov. 1, 2004).

Rudikoff et al., Proc. Natl. Acad. Sci. USA, Immunology, vol. 79, (1982), pp. 1979-1983, abstract on p. 1979.

Sakamoto et al. et al., "Cloning and Functional Expression of Human cDNA for the $ET_B$ Endothelin Receptor" Biochem Bioph Res Co 178(2):656-663 ( 1991).

Takizawa et al., "Immunolocalization of Endothelin-B Receptor in Mouse Intestinal Tract" Journal of Cardiovascular Pharmacology 44( Suppl 1):S329-S331 (Nov. 2004).

Vajdos et al. et al., "Comprehensive functional maps of the antigen-binding site of an anti-ErbB2 antibody obtained with shotgun scanning mutagenesis" J Mol Biol 320(2):415-428 (Jul. 5, 2002).

Vane et al. et al., "Endothelins come home to roost" Nature 348(6303):673 ( 1990).

Wu et al., "Humanization of a Murine Monoclonal Antibody by Simultaneous Optimization of Framework and CDR Residues" J Mol Biol 294:151-162 ( 1999).

Yamaguchi et al., "Characterization and Application of Monoclonal Antibodies Against Human Endothelin B Receptor Expressed in Insect Cells" Biotechnology Letters 26(4):293-299 (Feb. 2004).

Yokomori et al., "Enhanced Expression of Endothelin B Receptor at Protein and Gene Levels in Human Cirrhotic Liver" The American Journal of Pathology 159(4):1353-1362 (Oct. 2001).

FIGURE 1

GCATCTGGTTTGTCAGATCCGAGAGGCTCTGAAACTGCGGAGCGGCCACCGGACGCCTTCTGGAGCAGGTAG
CAGCATGCAGCCGCCTCCAAGTCTGTGCGGACGCGCCCTGGTTGCGCTGGTTCTTGCCTGCGGCCTGTCGCG
GATCTGGGGAGAGGAGAGAGGCTTCCCGCCTGACAGGGCCACTCCGCTTTTGCAAACCGCAGAGATAATGAC
GCCACCCACTAAGACCTTATGGCCCAAGGGTTCCAACGCCAGTCTGGCGCGGTCGTTGGCACCTGCGGAGGT
GCCTAAAGGAGACAGGACGGCAGGATCTCCGCCACGCACCATCTCCCCTCCCCCGTGCCAAGGACCCATCGA
GATCAAGGAGACTTTCAAATACATCAACACGGTTGTGTCCTGCCTTGTGTTCGTGCTGGGGATCATCGGGAA
CTCCACACTTCTGAGAATTATCTACAAGAACAAGTGCATGCGAAACGGTCCCAATATCTTGATCGCCAGCTT
GGCTCTGGGAGACCTGCTGCACATCGTCATTGACATCCCTATCAATGTCTACAAGCTGCTGGCAGAGGACTG
GCCATTTGGAGCTGAGATGTGTAAGCTGGTGCCTTTCATACAGAAAGCCTCCGTGGGAATCACTGTGCTGAG
TCTATGTGCTCTGAGTATTGACAGATATCGAGCTGTTGCTTCTTGGAGTAGAATTAAAGGAATTGGGGTTCC
AAAATGGACAGCAGTAGAAATTGTTTTGATTTGGGTGGTCTCTGTGGTTCTGGCTGTCCCTGAAGCCATAGG
TTTTGATATAATTACGATGGACTACAAAGGAAGTTATCTGCGAATCTGCTTGCTTCATCCCGTTCAGAAGAC
AGCTTTCATGCAGTTTTACAAGACAGCAAAAGATTGGTGGCTGTTCAGTTTCTATTTCTGCTTGCCATTGGC
CATCACTGCATTTTTTTATACACTAATGACCTGTGAAATGTTGAGAAAGAAAAGTGGCATGCAGATTGCTTT
AAATGATCACCTAAAGCAGAGACGGGAAGTGGCCAAAACCGTCTTTTGCCTGGTCCTTGTCTTTGCCCTCTG
CTGGCTTCCCCTTCACCTCAGCAGGATTCTGAAGCTCACTCTTTATAATCAGAATGATCCCAATAGATGTGA
ACTTTTGAGCTTTCTGTTGGTATTGGACTATATTGGTATCAACATGGCTTCACTGAATTCCTGCATTAACCC
AATTGCTCTGTATTTGGTGAGCAAAAGATTCAAAAACTGCTTTAAGTCATGCTTATGCTGCTGGTGCCAGTC
ATTTGAAGAAAAACAGTCCTTGGAGGAAAAGCAGTCGTGCTTAAAGTTCAAAGCTAATGATCACGGATATGA
CAACTTCCGTTCCAGTAATAAATACAGCTCATCTTGAAAGAAAAAAAAAAAAAAAAAAAAAAAAAAAAAAAA
AAAAAAAAAAAAA (SEQ ID NO:1)

FIGURE 2

MQPPPSLCGRALVALVLACGLSRIWGEERGFPPDRATPLLQTAEIMTPPTKTLWPKGSNASLARSLAPAEVPKGD
RTAGSPPRTISPPPCQGPIEIKETFKYINTVVSCLVFVLGIIGNSTLLRIIYKNKCMRNGPNILIASLALGDLLH
IVIDIPINVYKLLAEDWPFGAEMCKLVPFIQKASVGITVLSLCALSIDRYRAVASWSRIKGIGVPKWTAVEIVLI
WVVSVVLAVPEAIGFDIITMDYKGSYLRICLLHPVQKTAFMQFYKTAKDWWLFSFYFCLPLAITAFFYTLMTCEM
LRKKSGMQIALNDHLKQRREVAKTVFCLVLVFALCWLPLHLSRILKLTLYNQNDPNRCELLSFLLVLDYIGINMA
SLNSCINPIALYLVSKRFKNCFKSCLCCWCQSFEEKQSLEEKQSCLKFKANDHGYDNFRSSNKYSSS (SEQ ID
NO:2)

Signal sequence.

amino acids 1-26

Transmembrane domains.

amino acids 101-121, 137-157, 177-197, 216-236, 275-295, 323-343, 362-382

N-glycosylation sites.

amino acids 59-62, 119-122 cAMP- and cGMP-dependent protein kinase phosphorylation site.

amino acids 302-305

Tyrosine kinase phosphorylation site.

amino acids 424-430

N-myristoylation sites.

amino acids 57-62, 115-120, 170-175, 306-311, 371-376

7 transmembrane receptor homology.

amino acids 118-386

FIGURE 3

Full-Length Light Chain of Murine 5E9

DVVMTQTPLTLSVTIGQPASISCKSSQSLLDSDGKTYLNWLLQRPGQSPKRLIYLVSKLDSGVPDRFTGSGSGTD
FTLKITRVEAEDLGVYYCWQGTHFPYTFGGGTKLEIKRADAAPTVSIFPPSSEQLTSGGASVVCFLNNFYPKDIN
VKWKIDGSERQNGVLNSWTDQDSKDSTYSMSSTLTLTKDEYERHNSYTCEATHKTSTSPIVKSFNRNEC (SEQ
ID NO:3)

VL of Murine 5E9

DVVMTQTPLTLSVTIGQPASISCKSSQSLLDSDGKTYLNWLLQRPGQSPKRLIYLVSKLDSGVPDRFTGSGSGTD
FTLKITRVEAEDLGVYYCWQGTHFPYTFGGGTKLEIK (SEQ ID NO:5)

FIGURE 4

Full-Length Heavy Chain of Murine 5E9

QVQLLQSGAELARPGASVKLSCKASGYTFTSYWMQWVKQRPGQGLEWIGTIYPGDGDTSYAQKFKGKATLTTDKY
SSTAYMQLSSLASEDSAVYYCARWGYAYDIDNWGQGTTVTVSSASTKGPSVYPLAPVCGDTTGSSVTLGCLVKGY
FPEPVTLTWNSGSLSSGVHTFPAVLQSDLYTLSSSVTVTSSTWPSQSITCNVAHPASSTKVDKKIEPRGPTIKPC
PPCKCPAPNLLGGPSVFIFPPKIKDVLMISLSPIVTCVVVDVSEDDPDVQISWFVNNVEVHTAQTQTHREDYNST
LRVVSALPIQHQDWMSGKEFKCKVNNKDLPAPIERTISKPKGSVRAPQVYVLPPPEEEMTKKQVTLTCMVTDFMP
EDIYVEWTNNGKTELNYKNTEPVLDSDGSYFMYSKLRVEKKNWVERNSYSCSVVHEGLHNHHTTKSFSRTPGK
(SEQ ID NO:4)

VH of Murine 5E9

QVQLLQSGAELARPGASVKLSCKASGYTFTSYWMQWVKQRPGQGLEWIGTIYPGDGDTSYAQKFKGKATLTTDKY
SSTAYMQLSSLASEDSAVYYCARWGYAYDIDNWG (SEQ ID NO:6)

FIGURE 5

Full-Length Light Chain of hu5E9.v1

DIQMTQSPSSLSASVGDRVTITCKSSQSLLDSDGKTYLNWLQQKPGKAPKRLIYLVSKLDSGVPSRFSGSGSGTD
FTLTISSLQPEDFATYYCWQGTHFPYTFGQGTKVEIKRTVAAPSVFIFPPSDEQLKSGTASVVCLLNNFYPREAK
VQWKVDNALQSGNSQESVTEQDSKDSTYSLSSTLTLSKADYEKHKVYACEVTHQGLSSPVTKSFNRGEC (SEQ
ID NO:13)

VL of hu5E9.v1

DIQMTQSPSSLSASVGDRVTITCKSSQSLLDSDGKTYLNWLQQKPGKAPKRLIYLVSKLDSGVPSRFSGSGSGTD
FTLTISSLQPEDFATYYCWQGTHFPYTFGQGTKVEIK (SEQ ID NO:15)

FIGURE 6

Full-Length Heavy Chain of hu5E9.v1

EVQLVESGGGLVQPGGSLRLSCAASGYTFTSYWMQWVRQAPGKGLEWIGTIYPGDGDTSYAQKFKGRATLSTDKS
KNTAYLQMNSLRAEDTAVYYCARWGYAYDIDNWGQGTLVTVSSASTKGPSVFPLAPSSKSTSGGTAALGCLVKDY
FPEPVTVSWNSGALTSGVHTFPAVLQSSGLYSLSSVVTVPSSSLGTQTYICNVNHKPSNTKVDKKVEPKSCDKTH
TCPPCPAPELLGGPSVFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTLPPSREEMTKNQVSLTCLVKGFYP
SDIAVEWESNGQPENNYKTTPPVLDSDGSFFLYSKLTVDKSRWQQGNVFSCSVMHEALHNHYTQKSLSLSPGK
(SEQ ID NO:14)

VH of hu5E9.v1

EVQLVESGGGLVQPGGSLRLSCAASGYTFTSYWMQWVRQAPGKGLEWIGTIYPGDGDTSYAQKFKGRATLSTDKS
KNTAYLQMNSLRAEDTAVYYCARWGYAYDIDNWG (SEQ ID NO:16)

EVQLVQSGAEVKKPGASVKVSCKASGYTFTSYWMQWVRQAPGQGLEWIGTIYPGDGDTSYAQKFKGRVTITRDTS
TSTAYLELSSLRSEDTAVYYCARWGYAYDIDNWG (SEQ ID NO:17)

SEQUENCE LISTING

```
<160> NUMBER OF SEQ ID NOS: 17

<210> SEQ ID NO 1
<211> LENGTH: 1453
<212> TYPE: DNA
<213> ORGANISM: Homo sapiens

<400> SEQUENCE: 1
gcatctggtt tgtcagatcc gagaggctct gaaactgcgg agcggccacc            50
ggacgccttc tggagcaggt agcagcatgc agccgcctcc aagtctgtgc           100
ggacgcgccc tggttgcgct ggttcttgcc tgcggcctgt cgcggatctg           150
gggagaggag agaggcttcc cgcctgacag ggccactccg cttttgcaaa           200
```

-continued

| | |
|---|---|
| ccgcagagat aatgacgcca cccactaaga ccttatggcc caagggttcc | 250 |
| aacgccagtc tggcgcggtc gttggcacct gcggaggtgc ctaaaggaga | 300 |
| caggacggca ggatctccgc cacgcaccat ctcccctccc ccgtgccaag | 350 |
| gacccatcga gatcaaggag actttcaaat acatcaacac ggttgtgtcc | 400 |
| tgccttgtgt tcgtgctggg gatcatcggg aactccacac ttctgagaat | 450 |
| tatctacaag aacaagtgca tgcgaaacgg tcccaatatc ttgatcgcca | 500 |
| gcttggctct gggagacctg ctgcacatcg tcattgacat ccctatcaat | 550 |
| gtctacaagc tgctggcaga ggactggcca tttggagctg agatgtgtaa | 600 |
| gctggtgcct ttcatacaga aagcctccgt gggaatcact gtgctgagtc | 650 |
| tatgtgctct gagtattgac agatatcgag ctgttgcttc ttggagtaga | 700 |
| attaaaggaa ttggggttcc aaaatggaca gcagtagaaa ttgttttgat | 750 |
| ttgggtggtc tctgtggttc tggctgtccc tgaagccata ggttttgata | 800 |
| taattacgat ggactacaaa ggaagttatc tgcgaatctg cttgcttcat | 850 |
| cccgttcaga agacagcttt catgcagttt tacaagacag caaaagattg | 900 |
| gtggctgttc agtttctatt tctgcttgcc attggccatc actgcatttt | 950 |
| tttatacact aatgacctgt gaaatgttga gaaagaaaag tggcatgcag | 1000 |
| attgctttaa atgatcacct aaagcagaga cgggaagtgg ccaaaaccgt | 1050 |
| cttttgcctg gtccttgtct ttgccctctg ctggcttccc cttcacctca | 1100 |
| gcaggattct gaagctcact ctttataatc agaatgatcc caatagatgt | 1150 |
| gaacttttga gctttctgtt ggtattggac tatattggta tcaacatggc | 1200 |
| ttcactgaat tcctgcatta acccaattgc tctgtatttg gtgagcaaaa | 1250 |
| gattcaaaaa ctgctttaag tcatgcttat gctgctggtg ccagtcattt | 1300 |
| gaagaaaaac agtccttgga ggaaaagcag tcgtgcttaa agttcaaagc | 1350 |
| taatgatcac ggatatgaca acttccgttc cagtaataaa tacagctcat | 1400 |
| cttgaaagaa aaaaaaaaaa aaaaaaaaaa aaaaaaaaaa aaaaaaaaaa | 1450 |
| aaa | 1453 |

<210> SEQ ID NO 2
<211> LENGTH: 442
<212> TYPE: PRT
<213> ORGANISM: Homo sapiens

<400> SEQUENCE: 2

Met Gln Pro Pro Ser Leu Cys Gly Arg Ala Leu Val Ala Leu
 1               5                  10                  15

Val Leu Ala Cys Gly Leu Ser Arg Ile Trp Gly Glu Glu Arg Gly
            20                  25                  30

Phe Pro Pro Asp Arg Ala Thr Pro Leu Leu Gln Thr Ala Glu Ile
        35                  40                  45

Met Thr Pro Pro Thr Lys Thr Leu Trp Pro Lys Gly Ser Asn Ala
    50                  55                  60

Ser Leu Ala Arg Ser Leu Ala Pro Ala Glu Val Pro Lys Gly Asp
65                  70                  75

Arg Thr Ala Gly Ser Pro Pro Arg Thr Ile Ser Pro Pro Pro Cys
            80                  85                  90

Gln Gly Pro Ile Glu Ile Lys Glu Thr Phe Lys Tyr Ile Asn Thr
                    95                  100                 105

Val Val Ser Cys Leu Val Phe Val Leu Gly Ile Ile Gly Asn Ser
            110                 115                 120

Thr Leu Leu Arg Ile Ile Tyr Lys Asn Lys Cys Met Arg Asn Gly
            125                 130                 135

Pro Asn Ile Leu Ile Ala Ser Leu Ala Leu Gly Asp Leu Leu His
            140                 145                 150

Ile Val Ile Asp Ile Pro Ile Asn Val Tyr Lys Leu Leu Ala Glu
            155                 160                 165

Asp Trp Pro Phe Gly Ala Glu Met Cys Lys Leu Val Pro Phe Ile
            170                 175                 180

Gln Lys Ala Ser Val Gly Ile Thr Val Leu Ser Leu Cys Ala Leu
            185                 190                 195

Ser Ile Asp Arg Tyr Arg Ala Val Ala Ser Trp Ser Arg Ile Lys
            200                 205                 210

Gly Ile Gly Val Pro Lys Trp Thr Ala Val Glu Ile Val Leu Ile
            215                 220                 225

Trp Val Val Ser Val Val Leu Ala Val Pro Glu Ala Ile Gly Phe
            230                 235                 240

Asp Ile Ile Thr Met Asp Tyr Lys Gly Ser Tyr Leu Arg Ile Cys
            245                 250                 255

Leu Leu His Pro Val Gln Lys Thr Ala Phe Met Gln Phe Tyr Lys
            260                 265                 270

Thr Ala Lys Asp Trp Trp Leu Phe Ser Phe Tyr Phe Cys Leu Pro
            275                 280                 285

Leu Ala Ile Thr Ala Phe Phe Tyr Thr Leu Met Thr Cys Glu Met
            290                 295                 300

Leu Arg Lys Lys Ser Gly Met Gln Ile Ala Leu Asn Asp His Leu
            305                 310                 315

Lys Gln Arg Arg Glu Val Ala Lys Thr Val Phe Cys Leu Val Leu
            320                 325                 330

Val Phe Ala Leu Cys Trp Leu Pro Leu His Leu Ser Arg Ile Leu
            335                 340                 345

Lys Leu Thr Leu Tyr Asn Gln Asn Asp Pro Asn Arg Cys Glu Leu
            350                 355                 360

Leu Ser Phe Leu Leu Val Leu Asp Tyr Ile Gly Ile Asn Met Ala
            365                 370                 375

Ser Leu Asn Ser Cys Ile Asn Pro Ile Ala Leu Tyr Leu Val Ser
            380                 385                 390

Lys Arg Phe Lys Asn Cys Phe Lys Ser Cys Leu Cys Cys Trp Cys
            395                 400                 405

Gln Ser Phe Glu Glu Lys Gln Ser Leu Glu Glu Lys Gln Ser Cys
            410                 415                 420

Leu Lys Phe Lys Ala Asn Asp His Gly Tyr Asp Asn Phe Arg Ser
            425                 430                 435

Ser Asn Lys Tyr Ser Ser Ser
            440

<210> SEQ ID NO 3
<211> LENGTH: 219
<212> TYPE: PRT
<213> ORGANISM: Homo sapiens

<400> SEQUENCE: 3

-continued

Asp Val Val Met Thr Gln Thr Pro Leu Thr Leu Ser Val Thr Ile
 1               5                  10                  15

Gly Gln Pro Ala Ser Ile Ser Cys Lys Ser Ser Gln Ser Leu Leu
            20                  25                  30

Asp Ser Asp Gly Lys Thr Tyr Leu Asn Trp Leu Leu Gln Arg Pro
            35                  40                  45

Gly Gln Ser Pro Lys Arg Leu Ile Tyr Leu Val Ser Lys Leu Asp
            50                  55                  60

Ser Gly Val Pro Asp Arg Phe Thr Gly Ser Gly Ser Gly Thr Asp
            65                  70                  75

Phe Thr Leu Lys Ile Thr Arg Val Glu Ala Glu Asp Leu Gly Val
            80                  85                  90

Tyr Tyr Cys Trp Gln Gly Thr His Phe Pro Tyr Thr Phe Gly Gly
            95                 100                 105

Gly Thr Lys Leu Glu Ile Lys Arg Ala Asp Ala Ala Pro Thr Val
           110                 115                 120

Ser Ile Phe Pro Pro Ser Ser Glu Gln Leu Thr Ser Gly Gly Ala
           125                 130                 135

Ser Val Val Cys Phe Leu Asn Asn Phe Tyr Pro Lys Asp Ile Asn
           140                 145                 150

Val Lys Trp Lys Ile Asp Gly Ser Glu Arg Gln Asn Gly Val Leu
           155                 160                 165

Asn Ser Trp Thr Asp Gln Asp Ser Lys Asp Ser Thr Tyr Ser Met
           170                 175                 180

Ser Ser Thr Leu Thr Leu Thr Lys Asp Glu Tyr Glu Arg His Asn
           185                 190                 195

Ser Tyr Thr Cys Glu Ala Thr His Lys Thr Ser Thr Ser Pro Ile
           200                 205                 210

Val Lys Ser Phe Asn Arg Asn Glu Cys
           215

<210> SEQ ID NO 4
<211> LENGTH: 448
<212> TYPE: PRT
<213> ORGANISM: Homo sapiens

<400> SEQUENCE: 4

Gln Val Gln Leu Leu Gln Ser Gly Ala Glu Leu Ala Arg Pro Gly
 1               5                  10                  15

Ala Ser Val Lys Leu Ser Cys Lys Ala Ser Gly Tyr Thr Phe Thr
            20                  25                  30

Ser Tyr Trp Met Gln Trp Val Lys Gln Arg Pro Gly Gln Gly Leu
            35                  40                  45

Glu Trp Ile Gly Thr Ile Tyr Pro Gly Asp Gly Asp Thr Ser Tyr
            50                  55                  60

Ala Gln Lys Phe Lys Gly Lys Ala Thr Leu Thr Thr Asp Lys Tyr
            65                  70                  75

Ser Ser Thr Ala Tyr Met Gln Leu Ser Ser Leu Ala Ser Glu Asp
            80                  85                  90

Ser Ala Val Tyr Tyr Cys Ala Arg Trp Gly Tyr Ala Tyr Asp Ile
            95                 100                 105

Asp Asn Trp Gly Gln Gly Thr Thr Val Thr Val Ser Ser Ala Ser
           110                 115                 120

Thr Lys Gly Pro Ser Val Tyr Pro Leu Ala Pro Val Cys Gly Asp

```
                    125                 130                 135
Thr Thr Gly Ser Ser Val Thr Leu Gly Cys Leu Val Lys Gly Tyr
            140                 145                 150

Phe Pro Glu Pro Val Thr Leu Thr Trp Asn Ser Gly Ser Leu Ser
            155                 160                 165

Ser Gly Val His Thr Phe Pro Ala Val Leu Gln Ser Asp Leu Tyr
            170                 175                 180

Thr Leu Ser Ser Ser Val Thr Val Thr Ser Ser Thr Trp Pro Ser
            185                 190                 195

Gln Ser Ile Thr Cys Asn Val Ala His Pro Ala Ser Ser Thr Lys
            200                 205                 210

Val Asp Lys Lys Ile Glu Pro Arg Gly Pro Thr Ile Lys Pro Cys
            215                 220                 225

Pro Pro Cys Lys Cys Pro Ala Pro Asn Leu Leu Gly Gly Pro Ser
            230                 235                 240

Val Phe Ile Phe Pro Pro Lys Ile Lys Asp Val Leu Met Ile Ser
            245                 250                 255

Leu Ser Pro Ile Val Thr Cys Val Val Val Asp Val Ser Glu Asp
            260                 265                 270

Asp Pro Asp Val Gln Ile Ser Trp Phe Val Asn Asn Val Glu Val
            275                 280                 285

His Thr Ala Gln Thr Gln Thr His Arg Glu Asp Tyr Asn Ser Thr
            290                 295                 300

Leu Arg Val Val Ser Ala Leu Pro Ile Gln His Gln Asp Trp Met
            305                 310                 315

Ser Gly Lys Glu Phe Lys Cys Lys Val Asn Asn Lys Asp Leu Pro
            320                 325                 330

Ala Pro Ile Glu Arg Thr Ile Ser Lys Pro Lys Gly Ser Val Arg
            335                 340                 345

Ala Pro Gln Val Tyr Val Leu Pro Pro Glu Glu Glu Met Thr
            350                 355                 360

Lys Lys Gln Val Thr Leu Thr Cys Met Val Thr Asp Phe Met Pro
            365                 370                 375

Glu Asp Ile Tyr Val Glu Trp Thr Asn Asn Gly Lys Thr Glu Leu
            380                 385                 390

Asn Tyr Lys Asn Thr Glu Pro Val Leu Asp Ser Asp Gly Ser Tyr
            395                 400                 405

Phe Met Tyr Ser Lys Leu Arg Val Glu Lys Lys Asn Trp Val Glu
            410                 415                 420

Arg Asn Ser Tyr Ser Cys Ser Val Val His Glu Gly Leu His Asn
            425                 430                 435

His His Thr Thr Lys Ser Phe Ser Arg Thr Pro Gly Lys
            440                 445

<210> SEQ ID NO 5
<211> LENGTH: 112
<212> TYPE: PRT
<213> ORGANISM: Homo sapiens

<400> SEQUENCE: 5

Asp Val Val Met Thr Gln Thr Pro Leu Thr Leu Ser Val Thr Ile
  1               5                  10                  15

Gly Gln Pro Ala Ser Ile Ser Cys Lys Ser Ser Gln Ser Leu Leu
                 20                  25                  30
```

-continued

Asp Ser Asp Gly Lys Thr Tyr Leu Asn Trp Leu Leu Gln Arg Pro
                35                  40                  45

Gly Gln Ser Pro Lys Arg Leu Ile Tyr Leu Val Ser Lys Leu Asp
            50                  55                  60

Ser Gly Val Pro Asp Arg Phe Thr Gly Ser Gly Ser Gly Thr Asp
65                  70                  75

Phe Thr Leu Lys Ile Thr Arg Val Glu Ala Glu Asp Leu Gly Val
            80                  85                  90

Tyr Tyr Cys Trp Gln Gly Thr His Phe Pro Tyr Thr Phe Gly Gly
            95                      100                 105

Gly Thr Lys Leu Glu Ile Lys
            110

<210> SEQ ID NO 6
<211> LENGTH: 109
<212> TYPE: PRT
<213> ORGANISM: Homo sapiens

<400> SEQUENCE: 6

Gln Val Gln Leu Leu Gln Ser Gly Ala Glu Leu Ala Arg Pro Gly
1               5                   10                  15

Ala Ser Val Lys Leu Ser Cys Lys Ala Ser Gly Tyr Thr Phe Thr
            20                  25                  30

Ser Tyr Trp Met Gln Trp Val Lys Gln Arg Pro Gly Gln Gly Leu
            35                  40                  45

Glu Trp Ile Gly Thr Ile Tyr Pro Gly Asp Gly Asp Thr Ser Tyr
            50                  55                  60

Ala Gln Lys Phe Lys Gly Lys Ala Thr Leu Thr Thr Asp Lys Tyr
            65                  70                  75

Ser Ser Thr Ala Tyr Met Gln Leu Ser Ser Leu Ala Ser Glu Asp
            80                  85                  90

Ser Ala Val Tyr Tyr Cys Ala Arg Trp Gly Tyr Ala Tyr Asp Ile
            95                      100                 105

Asp Asn Trp Gly

<210> SEQ ID NO 7
<211> LENGTH: 16
<212> TYPE: PRT
<213> ORGANISM: Homo sapiens

<400> SEQUENCE: 7

Lys Ser Ser Gln Ser Leu Leu Asp Ser Asp Gly Lys Thr Tyr Leu
1               5                   10                  15

Asn

<210> SEQ ID NO 8
<211> LENGTH: 7
<212> TYPE: PRT
<213> ORGANISM: Homo sapiens

<400> SEQUENCE: 8

Leu Val Ser Lys Leu Asp Ser
                5

<210> SEQ ID NO 9
<211> LENGTH: 9
<212> TYPE: PRT
<213> ORGANISM: Homo sapiens

```
<400> SEQUENCE: 9

Trp Gln Gly Thr His Phe Pro Tyr Thr
                5

<210> SEQ ID NO 10
<211> LENGTH: 10
<212> TYPE: PRT
<213> ORGANISM: Homo sapiens

<400> SEQUENCE: 10

Gly Tyr Thr Phe Thr Ser Tyr Trp Met Gln
                5                   10

<210> SEQ ID NO 11
<211> LENGTH: 17
<212> TYPE: PRT
<213> ORGANISM: Homo sapiens

<400> SEQUENCE: 11

Thr Ile Tyr Pro Gly Asp Gly Asp Thr Ser Tyr Ala Gln Lys Phe
 1               5                  10                  15

Lys Gly

<210> SEQ ID NO 12
<211> LENGTH: 9
<212> TYPE: PRT
<213> ORGANISM: Homo sapiens

<400> SEQUENCE: 12

Trp Gly Tyr Ala Tyr Asp Ile Asp Asn
                5

<210> SEQ ID NO 13
<211> LENGTH: 219
<212> TYPE: PRT
<213> ORGANISM: Homo sapiens

<400> SEQUENCE: 13

Asp Ile Gln Met Thr Gln Ser Pro Ser Ser Leu Ser Ala Ser Val
 1               5                  10                  15

Gly Asp Arg Val Thr Ile Thr Cys Lys Ser Ser Gln Ser Leu Leu
                20                  25                  30

Asp Ser Asp Gly Lys Thr Tyr Leu Asn Trp Leu Gln Gln Lys Pro
                35                  40                  45

Gly Lys Ala Pro Lys Arg Leu Ile Tyr Leu Val Ser Lys Leu Asp
                50                  55                  60

Ser Gly Val Pro Ser Arg Phe Ser Gly Ser Gly Ser Gly Thr Asp
                65                  70                  75

Phe Thr Leu Thr Ile Ser Ser Leu Gln Pro Glu Asp Phe Ala Thr
                80                  85                  90

Tyr Tyr Cys Trp Gln Gly Thr His Phe Pro Tyr Thr Phe Gly Gln
                95                  100                 105

Gly Thr Lys Val Glu Ile Lys Arg Thr Val Ala Ala Pro Ser Val
                110                 115                 120

Phe Ile Phe Pro Pro Ser Asp Glu Gln Leu Lys Ser Gly Thr Ala
                125                 130                 135

Ser Val Val Cys Leu Leu Asn Asn Phe Tyr Pro Arg Glu Ala Lys
                140                 145                 150

Val Gln Trp Lys Val Asp Asn Ala Leu Gln Ser Gly Asn Ser Gln
```

```
                    155                 160                 165

Glu Ser Val Thr Glu Gln Asp Ser Lys Asp Ser Thr Tyr Ser Leu
                170                 175                 180

Ser Ser Thr Leu Thr Leu Ser Lys Ala Asp Tyr Glu Lys His Lys
                185                 190                 195

Val Tyr Ala Cys Glu Val Thr His Gln Gly Leu Ser Ser Pro Val
                200                 205                 210

Thr Lys Ser Phe Asn Arg Gly Glu Cys
                215

<210> SEQ ID NO 14
<211> LENGTH: 448
<212> TYPE: PRT
<213> ORGANISM: Homo sapiens

<400> SEQUENCE: 14

Glu Val Gln Leu Val Glu Ser Gly Gly Gly Leu Val Gln Pro Gly
  1               5                  10                  15

Gly Ser Leu Arg Leu Ser Cys Ala Ala Ser Gly Tyr Thr Phe Thr
                 20                  25                  30

Ser Tyr Trp Met Gln Trp Val Arg Gln Ala Pro Gly Lys Gly Leu
                 35                  40                  45

Glu Trp Ile Gly Thr Ile Tyr Pro Gly Asp Gly Asp Thr Ser Tyr
                 50                  55                  60

Ala Gln Lys Phe Lys Gly Arg Ala Thr Leu Ser Thr Asp Lys Ser
                 65                  70                  75

Lys Asn Thr Ala Tyr Leu Gln Met Asn Ser Leu Arg Ala Glu Asp
                 80                  85                  90

Thr Ala Val Tyr Tyr Cys Ala Arg Trp Gly Tyr Ala Tyr Asp Ile
                 95                 100                 105

Asp Asn Trp Gly Gln Gly Thr Leu Val Thr Val Ser Ser Ala Ser
                110                 115                 120

Thr Lys Gly Pro Ser Val Phe Pro Leu Ala Pro Ser Ser Lys Ser
                125                 130                 135

Thr Ser Gly Gly Thr Ala Ala Leu Gly Cys Leu Val Lys Asp Tyr
                140                 145                 150

Phe Pro Glu Pro Val Thr Val Ser Trp Asn Ser Gly Ala Leu Thr
                155                 160                 165

Ser Gly Val His Thr Phe Pro Ala Val Leu Gln Ser Ser Gly Leu
                170                 175                 180

Tyr Ser Leu Ser Ser Val Val Thr Val Pro Ser Ser Ser Leu Gly
                185                 190                 195

Thr Gln Thr Tyr Ile Cys Asn Val Asn His Lys Pro Ser Asn Thr
                200                 205                 210

Lys Val Asp Lys Lys Val Glu Pro Lys Ser Cys Asp Lys Thr His
                215                 220                 225

Thr Cys Pro Pro Cys Pro Ala Pro Glu Leu Leu Gly Gly Pro Ser
                230                 235                 240

Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val
                275                 280                 285
```

```
His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu
            305                 310                 315

Asn Gly Lys Glu Tyr Lys Cys Lys Val Ser Asn Lys Ala Leu Pro
            320                 325                 330

Ala Pro Ile Glu Lys Thr Ile Ser Lys Ala Lys Gly Gln Pro Arg
            335                 340                 345

Glu Pro Gln Val Tyr Thr Leu Pro Pro Ser Arg Glu Glu Met Thr
            350                 355                 360

Lys Asn Gln Val Ser Leu Thr Cys Leu Val Lys Gly Phe Tyr Pro
            365                 370                 375

Ser Asp Ile Ala Val Glu Trp Glu Ser Asn Gly Gln Pro Glu Asn
            380                 385                 390

Asn Tyr Lys Thr Thr Pro Pro Val Leu Asp Ser Asp Gly Ser Phe
            395                 400                 405

Phe Leu Tyr Ser Lys Leu Thr Val Asp Lys Ser Arg Trp Gln Gln
            410                 415                 420

Gly Asn Val Phe Ser Cys Ser Val Met His Glu Ala Leu His Asn
            425                 430                 435

His Tyr Thr Gln Lys Ser Leu Ser Leu Ser Pro Gly Lys
            440                 445

<210> SEQ ID NO 15
<211> LENGTH: 112
<212> TYPE: PRT
<213> ORGANISM: Homo sapiens

<400> SEQUENCE: 15

Asp Ile Gln Met Thr Gln Ser Pro Ser Ser Leu Ser Ala Ser Val
  1               5                  10                  15

Gly Asp Arg Val Thr Ile Thr Cys Lys Ser Ser Gln Ser Leu Leu
             20                  25                  30

Asp Ser Asp Gly Lys Thr Tyr Leu Asn Trp Leu Gln Gln Lys Pro
             35                  40                  45

Gly Lys Ala Pro Lys Arg Leu Ile Tyr Leu Val Ser Lys Leu Asp
             50                  55                  60

Ser Gly Val Pro Ser Arg Phe Ser Gly Ser Gly Ser Gly Thr Asp
             65                  70                  75

Phe Thr Leu Thr Ile Ser Ser Leu Gln Pro Glu Asp Phe Ala Thr
             80                  85                  90

Tyr Tyr Cys Trp Gln Gly Thr His Phe Pro Tyr Thr Phe Gly Gln
             95                 100                 105

Gly Thr Lys Val Glu Ile Lys
            110

<210> SEQ ID NO 16
<211> LENGTH: 109
<212> TYPE: PRT
<213> ORGANISM: Homo sapiens

<400> SEQUENCE: 16

Glu Val Gln Leu Val Glu Ser Gly Gly Gly Leu Val Gln Pro Gly
  1               5                  10                  15

Gly Ser Leu Arg Leu Ser Cys Ala Ala Ser Gly Tyr Thr Phe Thr
             20                  25                  30
```

-continued

```
Ser Tyr Trp Met Gln Trp Val Arg Gln Ala Pro Gly Lys Gly Leu
            35                  40                  45

Glu Trp Ile Gly Thr Ile Tyr Pro Gly Asp Gly Asp Thr Ser Tyr
            50                  55                  60

Ala Gln Lys Phe Lys Gly Arg Ala Thr Leu Ser Thr Asp Lys Ser
            65                  70                  75

Lys Asn Thr Ala Tyr Leu Gln Met Asn Ser Leu Arg Ala Glu Asp
            80                  85                  90

Thr Ala Val Tyr Tyr Cys Ala Arg Trp Gly Tyr Ala Tyr Asp Ile
            95                 100                 105

Asp Asn Trp Gly

<210> SEQ ID NO 17
<211> LENGTH: 109
<212> TYPE: PRT
<213> ORGANISM: Homo sapiens

<400> SEQUENCE: 17

Glu Val Gln Leu Val Gln Ser Gly Ala Glu Val Lys Lys Pro Gly
 1           5                  10                  15

Ala Ser Val Lys Val Ser Cys Lys Ala Ser Gly Tyr Thr Phe Thr
            20                  25                  30

Ser Tyr Trp Met Gln Trp Val Arg Gln Ala Pro Gly Gln Gly Leu
            35                  40                  45

Glu Trp Ile Gly Thr Ile Tyr Pro Gly Asp Gly Asp Thr Ser Tyr
            50                  55                  60

Ala Gln Lys Phe Lys Gly Arg Val Thr Ile Thr Arg Asp Thr Ser
            65                  70                  75

Thr Ser Thr Ala Tyr Leu Glu Leu Ser Ser Leu Arg Ser Glu Asp
            80                  85                  90

Thr Ala Val Tyr Tyr Cys Ala Arg Trp Gly Tyr Ala Tyr Asp Ile
            95                 100                 105

Asp Asn Trp Gly
```

COMPOSITIONS AND METHODS FOR THE DIAGNOSIS AND TREATMENT OF TUMOR

RELATED APPLICATIONS

This application is a divisional of U.S. patent application Ser. No. 13/031,848, filed on Feb. 22, 2011, issued as U.S. Pat. No. 8,877,897 on Nov. 4, 2014 which claims the benefit of US Provisional Patent Application Ser. Nos. 61/307,338, filed Feb. 23, 2010, and 61/308,791, filed Feb. 26, 2010. The contents of the foregoing applications are incorporated herein by reference in their entirety.

The sequence listing includes the sequences identified as Seq ID Nos: 1-17. This file is named P4412R1C1-US_Sequence_Listing.txt, is 23,425 bytes in size, was created on Sep. 25, 2014, and is IBM PC/XT/AT: MS-windows compatible.

FIELD OF THE INVENTION

The present invention is directed to compositions of matter useful for the diagnosis and treatment of tumor in mammals and to methods of using those compositions of matter for the same.

BACKGROUND OF INVENTION

Malignant tumors (cancers) are the second leading cause of death in the United States, after heart disease (Boring et al., CA Cancel J. Clin. 43:7 (1993)). Cancer is characterized by the increase in the number of abnormal, or neoplastic, cells derived from a normal tissue which proliferate to form a tumor mass, the invasion of adjacent tissues by these neoplastic tumor cells, and the generation of malignant cells which eventually spread via the blood or lymphatic system to regional lymph nodes and to distant sites via a process called metastasis. In a cancerous state, a cell proliferates under conditions in which normal cells would not grow. Cancer manifests itself in a wide variety of forms, characterized by different degrees of invasiveness and aggressiveness.

In attempts to discover effective cellular targets for cancer diagnosis and therapy, researchers have sought to identify transmembrane or otherwise membrane-associated polypeptides that are specifically expressed on the surface of one or more particular type(s) of cancer cell as compared to on one or more normal non-cancerous cell(s). Often, such membrane-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies. In this regard, it is noted that antibody-based therapy has proved very effective in the treatment of certain cancers. For example, HERCEPTIN® and RITUXAN® (both from Genentech Inc., South San Francisco, Calif.) are antibodies that have been used successfully to treat breast cancer and non-Hodgkin's lymphoma, respectively. More specifically, HERCEPTIN® is a recombinant DNA-derived humanized monoclonal antibody that selectively binds to the extracellular domain of the human epidermal growth factor receptor 2 (HER2) proto-oncogene. HER2 protein overexpression is observed in 25-30% of primary breast cancers. RITUXAN® is a genetically engineered chimeric murine/human monoclonal antibody directed against the CD20 antigen found on the surface of normal and malignant B lymphocytes. Both these antibodies are recombinantly produced in CHO cells.

Despite the above identified advances in mammalian cancer therapy, there is a great need for additional diagnostic and therapeutic agents capable of detecting the presence of tumor in a mammal and for effectively inhibiting neoplastic cell growth, respectively. Accordingly, it is an objective of the present invention to identify cell membrane-associated polypeptides that are more abundantly expressed on one or more type(s) of cancer cell(s) as compared to on normal cells or on other different cancer cells and to use those polypeptides, and their encoding nucleic acids, to produce compositions of matter useful in the therapeutic treatment and diagnostic detection of cancer in mammals.

SUMMARY OF INVENTION

In the present specification, Applicants describe for the first time the identification of cellular polypeptides (and their encoding nucleic acids or fragments thereof) which are expressed to a greater degree on the surface of one or more types of cancer cell(s) as compared to on the surface of one or more types of normal non-cancer cells. These polypeptides are herein referred to as Tumor-associated Antigenic Target polypeptides ("TAT" polypeptides) and are expected to serve as effective targets for cancer therapy and diagnosis in mammals.

Accordingly, in one embodiment of the present invention, the invention provides an isolated nucleic acid molecule having a nucleotide sequence that encodes a tumor-associated antigenic target polypeptide or fragment thereof (a "TAT" polypeptide).

In certain aspects, the isolated nucleic acid molecule comprises a nucleotide sequence having at least about 80% nucleic acid sequence identity, alternatively at least about 81%, 82%, 83%, 84%, 85%, 86%, 87%, 88%, 89%, 90%, 91%, 92%, 93%, 94%, 95%, 96%, 97%, 98%, 99% or 100% nucleic acid sequence identity, to (a) a DNA molecule encoding a full-length TAT polypeptide having an amino acid sequence as disclosed herein, a TAT polypeptide amino acid sequence lacking the signal peptide as disclosed herein, an extracellular domain of a transmembrane TAT polypeptide, with or without the signal peptide, as disclosed herein or any other specifically defined fragment of a full-length TAT polypeptide amino acid sequence as disclosed herein, or (b) the complement of the DNA molecule of (a).

In other aspects, the isolated nucleic acid molecule comprises a nucleotide sequence having at least about 80% nucleic acid sequence identity, alternatively at least about 81%, 82%, 83%, 84%, 85%, 86%, 87%, 88%, 89%, 90%, 91%, 92%, 93%, 94%, 95%, 96%, 97%, 98%, 99% or 100% nucleic acid sequence identity, to (a) a DNA molecule comprising the coding sequence of a full-length TAT polypeptide cDNA as disclosed herein, the coding sequence of a TAT polypeptide lacking the signal peptide as disclosed herein, the coding sequence of an extracellular domain of a transmembrane TAT polypeptide, with or without the signal peptide, as disclosed herein or the coding sequence of any other specifically defined fragment of the full-length TAT polypeptide amino acid sequence as disclosed herein, or (b) the complement of the DNA molecule of (a).

Another aspect of the invention provides an isolated nucleic acid molecule comprising a nucleotide sequence encoding a TAT polypeptide which is either transmembrane domain-deleted or transmembrane domain-inactivated, or is complementary to such encoding nucleotide sequence, wherein the transmembrane domain(s) of such polypeptide(s) are disclosed herein. Therefore, soluble extracellular domains of the herein described TAT polypeptides are contemplated.

In other aspects, the present invention is directed to isolated nucleic acid molecules which hybridize to (a) a nucleotide sequence encoding a TAT polypeptide having a full-length amino acid sequence as disclosed herein, a TAT polypeptide amino acid sequence lacking the signal peptide as disclosed herein, an extracellular domain of a transmembrane TAT polypeptide, with or without the signal peptide, as disclosed herein or any other specifically defined fragment of a full-length TAT polypeptide amino acid sequence as disclosed herein, or (b) the complement of the nucleotide sequence of (a). In this regard, an embodiment of the present invention is directed to fragments of a full-length TAT polypeptide coding sequence, or the complement thereof, as disclosed herein, that may find use as, for example, hybridization probes useful as, for example, diagnostic probes, PCR primers, antisense oligonucleotide probes, or for encoding fragments of a full-length TAT polypeptide that may optionally encode a polypeptide comprising a binding site for an anti-TAT polypeptide antibody. Such nucleic acid fragments are usually at least about 5 nucleotides in length, alternatively at least about 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides in length, wherein in this context the term "about" means the referenced nucleotide sequence length plus or minus 10% of that referenced length. Moreover, such nucleic acid fragments are usually comprised of consecutive nucleotides derived from the full-length coding sequence of a TAT polypeptide or the complement thereof. It is noted that novel fragments of a TAT polypeptide-encoding nucleotide sequence, or the complement thereof, may be determined in a routine manner by aligning the TAT polypeptide-encoding nucleotide sequence with other known nucleotide sequences using any of a number of well known sequence alignment programs and determining which TAT polypeptide-encoding nucleotide sequence fragment(s), or the complement thereof, are novel. All of such novel fragments of TAT polypeptide-encoding nucleotide sequences, or the complement thereof, are contemplated herein. Also contemplated are the TAT polypeptide fragments encoded by these nucleotide molecule fragments, preferably those TAT polypeptide fragments that comprise a binding site for an anti-TAT antibody.

In another embodiment, the invention provides isolated TAT polypeptides encoded by any of the isolated nucleic acid sequences hereinabove identified.

In a certain aspect, the invention concerns an isolated TAT polypeptide, comprising an amino acid sequence having at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, 99% or 100% amino acid sequence identity, to a TAT polypeptide having a full-length amino acid sequence as disclosed herein, a TAT polypeptide amino acid sequence lacking the signal peptide as disclosed herein, an extracellular domain of a transmembrane TAT polypeptide protein, with or without the signal peptide, as disclosed herein, an amino acid sequence encoded by any of the nucleic acid sequences disclosed herein or any other specifically defined fragment of a full-length TAT polypeptide amino acid sequence as disclosed herein.

In a yet further aspect, the invention concerns an isolated TAT polypeptide comprising an amino acid sequence that is encoded by a nucleotide sequence that hybridizes to the complement of a DNA molecule encoding (a) a TAT polypeptide having a full-length amino acid sequence as disclosed herein, (b) a TAT polypeptide amino acid sequence lacking the signal peptide as disclosed herein, (c) an extracellular domain of a transmembrane TAT polypeptide protein, with or without the signal peptide, as disclosed herein, (d) an amino acid sequence encoded by any of the nucleic acid sequences disclosed herein or (e) any other specifically defined fragment of a full-length TAT polypeptide amino acid sequence as disclosed herein.

In a specific aspect, the invention provides an isolated TAT polypeptide without the N-terminal signal sequence and/or without the initiating methionine and is encoded by a nucleotide sequence that encodes such an amino acid sequence as hereinbefore described. Processes for producing the same are also herein described, wherein those processes comprise culturing a host cell comprising a vector which comprises the appropriate encoding nucleic acid molecule under conditions suitable for expression of the TAT polypeptide and recovering the TAT polypeptide from the cell culture.

Another aspect of the invention provides an isolated TAT polypeptide which is either transmembrane domain-deleted or transmembrane domain-inactivated. Processes for producing the same are also herein described, wherein those processes comprise culturing a host cell comprising a vector which comprises the appropriate encoding nucleic acid molecule under conditions suitable for expression of the TAT polypeptide and recovering the TAT polypeptide from the cell culture.

In other embodiments of the present invention, the invention provides vectors comprising DNA encoding any of the herein described polypeptides. Host cells comprising any such vector are also provided. By way of example, the host cells may be CHO cells, *E. coli* cells, or yeast cells. A process for producing any of the herein described polypeptides is further provided and comprises culturing host cells under conditions suitable for expression of the desired polypeptide and recovering the desired polypeptide from the cell culture.

In other embodiments, the invention provides isolated chimeric polypeptides comprising any of the herein described TAT polypeptides fused to a heterologous (non-TAT) polypeptide. Examples of such chimeric molecules comprise any of the herein described TAT polypeptides fused to a heterologous polypeptide such as, for example, an epitope tag sequence or a Fc region of an immunoglobulin.

In another embodiment, the invention provides an antibody which binds, preferably specifically, to any of the above or below described polypeptides. Optionally, the antibody is a monoclonal antibody, antibody fragment, chimeric antibody, humanized antibody, single-chain antibody or antibody that competitively inhibits the binding of an anti-TAT polypeptide antibody to its respective antigenic epitope. Antibodies of the present invention may optionally be conjugated to a growth inhibitory agent or cytotoxic agent such as a toxin, including, for example, a maytansinoid or calicheamicin, an antibiotic, a radioactive isotope, a nucleolytic enzyme, or the like. The antibodies of the present invention may optionally be produced in CHO cells or bacterial cells and preferably inhibit the growth or proliferation of or induce the death of a cell to which they bind. For diagnostic purposes, the antibodies of the present invention may be detectably labeled, attached to a solid support, or the like.

In other embodiments of the present invention, the invention provides vectors comprising DNA encoding any of the herein described antibodies. Host cell comprising any such vector are also provided. By way of example, the host cells may be CHO cells, *E. coli* cells, or yeast cells. A process for producing any of the herein described antibodies is further provided and comprises culturing host cells under conditions suitable for expression of the desired antibody and recovering the desired antibody from the cell culture.

In a still further embodiment, the invention concerns a composition of matter comprising a TAT polypeptide as described herein, a chimeric TAT polypeptide as described herein, or an anti-TAT antibody as described herein, in combination with a carrier. Optionally, the carrier is a pharmaceutically acceptable carrier.

In yet another embodiment, the invention concerns an article of manufacture comprising a container and a composition of matter contained within the container, wherein the composition of matter may comprise a TAT polypeptide as described herein, a chimeric TAT polypeptide as described herein, or an anti-TAT antibody as described herein. The article may further optionally comprise a label affixed to the container, or a package insert included with the container, that refers to the use of the composition of matter for the therapeutic treatment or diagnostic detection of a tumor.

Another embodiment of the present invention is directed to the use of a TAT polypeptide as described herein, a chimeric TAT polypeptide as described herein, or an anti-TAT polypeptide antibody as described herein, for the preparation of a medicament useful in the treatment of a condition which is responsive to the TAT polypeptide, chimeric TAT polypeptide, or anti-TAT polypeptide antibody.

Other embodiments of the present invention are directed to any isolated antibody comprising one or more of the CDR-L1, CDR-L2, CDR-L3, CDR-H1, CDR-H2, or CDR-H3 sequences disclosed herein, or any antibody that binds to the same epitope as any such antibody.

Another embodiment of the present invention is directed to a method for inhibiting the growth of a cell that expresses a TAT polypeptide, wherein the method comprises contacting the cell with an antibody that binds to the TAT polypeptide, and wherein the binding of the antibody to the TAT polypeptide causes inhibition of the growth of the cell expressing the TAT polypeptide. In preferred embodiments, the cell is a cancer cell and binding of the antibody to the TAT polypeptide causes death of the cell expressing the TAT polypeptide. Optionally, the antibody is a monoclonal antibody, antibody fragment, chimeric antibody, humanized antibody, or single-chain antibody. Antibodies employed in the methods of the present invention may optionally be conjugated to a growth inhibitory agent or cytotoxic agent such as a toxin, including, for example, a maytansinoid or calicheamicin, an antibiotic, a radioactive isotope, a nucleolytic enzyme, or the like. The antibodies employed in the methods of the present invention may optionally be produced in CHO cells or bacterial cells.

Yet another embodiment of the present invention is directed to a method of therapeutically treating a mammal having a cancerous tumor comprising cells that express a TAT polypeptide, wherein the method comprises administering to the mammal a therapeutically effective amount of an antibody that binds to the TAT polypeptide, thereby resulting in the effective therapeutic treatment of the tumor. Optionally, the antibody is a monoclonal antibody, antibody fragment, chimeric antibody, humanized antibody, or single-chain antibody. Antibodies employed in the methods of the present invention may optionally be conjugated to a growth inhibitory agent or cytotoxic agent such as a toxin, including, for example, a maytansinoid or calicheamicin, an antibiotic, a radioactive isotope, a nucleolytic enzyme, or the like. The antibodies employed in the methods of the present invention may optionally be produced in CHO cells or bacterial cells.

Yet another embodiment of the present invention is directed to a method of determining the presence of a TAT polypeptide in a sample suspected of containing the TAT polypeptide, wherein the method comprises exposing the sample to (or contacting the sample with) an antibody that binds to the TAT polypeptide and determining or detecting the binding of the antibody to the TAT polypeptide in the sample, wherein the presence of such binding is indicative of the presence of the TAT polypeptide in the sample. Optionally, the sample may contain cells (which may be cancer cells) suspected of expressing the TAT polypeptide. The antibody employed in the method may optionally be detectably labeled, attached to a solid support, or the like.

A further embodiment of the present invention is directed to a method of diagnosing the presence of a tumor in a mammal, wherein the method comprises detecting the level of expression of a gene encoding a TAT polypeptide (a) in a test sample of tissue cells obtained from said mammal, and (b) in a control sample of known normal non-cancerous cells of the same tissue origin or type, wherein a higher level of expression of the TAT polypeptide in the test sample, as compared to the control sample, is indicative of the presence of tumor in the mammal from which the test sample was obtained.

Another embodiment of the present invention is directed to a method of diagnosing the presence of a tumor in a mammal, wherein the method comprises (a) contacting a test sample comprising tissue cells obtained from the mammal with an antibody that binds to a TAT polypeptide and (b) detecting the formation of a complex between the antibody and the TAT polypeptide in the test sample, wherein the formation of a complex is indicative of the presence of a tumor in the mammal. Optionally, the antibody employed is detectably labeled, attached to a solid support, or the like, and/or the test sample of tissue cells is obtained from an individual suspected of having a cancerous tumor.

Yet another embodiment of the present invention is directed to a method for treating or preventing a cell proliferative disorder associated with altered, preferably increased, expression or activity of a TAT polypeptide, the method comprising administering to a subject in need of such treatment an effective amount of an antagonist of a TAT polypeptide. Preferably, the cell proliferative disorder is cancer and the antagonist of the TAT polypeptide is an anti-TAT polypeptide antibody or antisense oligonucleotide. Effective treatment or prevention of the cell proliferative disorder may be a result of direct killing or growth inhibition of cells that express a TAT polypeptide or by antagonizing the cell growth potentiating activity of a TAT polypeptide.

Yet another embodiment of the present invention is directed to a method of binding an antibody to a cell that expresses a TAT polypeptide, wherein the method comprises contacting a cell that expresses a TAT polypeptide with said antibody under conditions which are suitable for binding of the antibody to said TAT polypeptide and allowing binding therebetween. In preferred embodiments, the antibody is labeled with a molecule or compound that is useful for qualitatively and/or quantitatively determining the location and/or amount of binding of the antibody to the cell.

Yet another embodiment of the present invention is directed to a method of delivering a cytotoxic or a diagnostic agent to a cell that expresses a TAT polypeptide, wherein the method comprises providing a cytotoxic agent or diagnostic agent conjugated to an antibody that binds to said TAT polypeptide to form an antibody-agent conjugate, and exposing the cell to the antibody-agent conjugate. Optionally, the antibody is a monoclonal antibody, antibody fragment, chimeric antibody, humanized antibody, or single-chain antibody.

Other embodiments of the present invention are directed to the use of a TAT polypeptide, a nucleic acid encoding a TAT polypeptide or a vector or host cell comprising that nucleic acid, or an anti-TAT polypeptide antibody in the preparation of a medicament useful for (i) the therapeutic treatment or diagnostic detection of a cancer or tumor, or (ii) the therapeutic treatment or prevention of a cell proliferative disorder.

Another embodiment of the present invention is directed to a method for inhibiting the growth of a cancer cell, wherein the growth of said cancer cell is at least in part dependent upon the growth potentiating effect(s) of a TAT polypeptide (wherein the TAT polypeptide may be expressed either by the cancer cell itself or a cell that produces polypeptide(s) that have a growth potentiating effect on cancer cells), wherein the method comprises contacting the TAT polypeptide with an antibody that binds to the TAT polypeptide, thereby antagonizing the growth-potentiating activity of the TAT polypeptide and, in turn, inhibiting the growth of the cancer cell. Preferably the growth of the cancer cell is completely inhibited. Even more preferably, binding of the antibody to the TAT polypeptide induces the death of the cancer cell. Optionally, the antibody is a monoclonal antibody, antibody fragment, chimeric antibody, humanized antibody, or single-chain antibody. Antibodies employed in the methods of the present invention may optionally be conjugated to a growth inhibitory agent or cytotoxic agent such as a toxin, including, for example, a maytansinoid or calicheamicin, an antibiotic, a radioactive isotope, a nucleolytic enzyme, or the like. The antibodies employed in the methods of the present invention may optionally be produced in CHO cells or bacterial cells.

Yet another embodiment of the present invention is directed to a method of therapeutically treating a tumor in a mammal, wherein the growth of said tumor is at least in part dependent upon the growth potentiating effect(s) of a TAT polypeptide, wherein the method comprises administering to the mammal a therapeutically effective amount of an antibody that binds to the TAT polypeptide, thereby antagonizing the growth potentiating activity of said TAT polypeptide and resulting in the effective therapeutic treatment of the tumor. Optionally, the antibody is a monoclonal antibody, antibody fragment, chimeric antibody, humanized antibody, or single-chain antibody. Antibodies employed in the methods of the present invention may optionally be conjugated to a growth inhibitory agent or cytotoxic agent such as a toxin, including, for example, a maytansinoid or calicheamicin, an antibiotic, a radioactive isotope, a nucleolytic enzyme, or the like. The antibodies employed in the methods of the present invention may optionally be produced in CHO cells or bacterial cells.

In yet further embodiments, the invention is directed to the following set of potential claims for this or future applications:

1. Isolated nucleic acid having a nucleotide sequence that has at least 80% nucleic acid sequence identity to (a) a DNA molecule encoding the amino acid sequence shown as SEQ ID NO:2, (b) a DNA molecule encoding the amino acid sequence shown as SEQ ID NO:2, lacking its associated signal peptide, (c) a DNA molecule encoding an extracellular domain of the polypeptide shown as SEQ ID NO:2, with its associated signal peptide, (d) a DNA molecule encoding an extracellular domain of the polypeptide shown as SEQ ID NO:2, lacking its associated signal peptide, (e) the nucleotide sequence shown as SEQ ID NO:1, (f) the full-length coding sequence of the nucleotide sequence shown as SEQ ID NO:1, or (g) the complement of (a), (b), (c), (d), (e) or (f).

2. Isolated nucleic acid having (a) a nucleotide sequence that encodes the amino acid sequence shown as SEQ ID NO:2, (b) a nucleotide sequence that encodes the amino acid sequence shown as SEQ ID NO:2, lacking its associated signal peptide, (c) a nucleotide sequence that encodes an extracellular domain of the polypeptide shown as SEQ ID NO:2, with its associated signal peptide, (d) a nucleotide sequence that encodes an extracellular domain of the polypeptide shown as SEQ ID NO:2, lacking its associated signal peptide, (e) the nucleotide sequence shown as SEQ ID NO:1, (f) the full-length coding region of the nucleotide sequence shown as SEQ ID NO:1, or (g) the complement of (a), (b), (c), (d), (e) or (f).

3. Isolated nucleic acid that hybridizes to (a) a nucleic acid that encodes the amino acid sequence shown as SEQ ID NO:2, (b) a nucleic acid that encodes the amino acid sequence shown as SEQ ID NO:2, lacking its associated signal peptide, (c) a nucleic acid that encodes an extracellular domain of the polypeptide shown as SEQ ID NO:2, with its associated signal peptide, (d) a nucleic acid that encodes an extracellular domain of the polypeptide shown as SEQ ID NO:2, lacking its associated signal peptide, (e) the nucleotide sequence shown as SEQ ID NO:1, (f) the full-length coding region of the nucleotide sequence shown as SEQ ID NO:1, or (g) the complement of (a), (b), (c), (d), (e) or (f).

4. The nucleic acid of Claim 3, wherein the hybridization occurs under stringent conditions.

5. The nucleic acid of Claim 3 which is at least about 5 nucleotides in length.

6. An expression vector comprising the nucleic acid of Claim 1, 2 or 3.

7. The expression vector of Claim 6, wherein said nucleic acid is operably linked to control sequences recognized by a host cell transformed with the vector.

8. A host cell comprising the expression vector of Claim 7.

9. The host cell of Claim 8 which is a CHO cell, an *E. coli* cell or a yeast cell.

10. A process for producing a polypeptide comprising culturing the host cell of Claim 8 under conditions suitable for expression of said polypeptide and recovering said polypeptide from the cell culture.

11. An isolated polypeptide having at least 80% amino acid sequence identity to (a) the polypeptide shown as SEQ ID NO:2, (b) the polypeptide shown as SEQ ID NO:2, lacking its associated signal peptide, (c) an extracellular domain of the polypeptide shown as SEQ ID NO:2, with its associated signal peptide, (d) an extracellular domain of the polypeptide shown as SEQ ID NO:2, lacking its associated signal peptide, (e) a polypeptide encoded by the nucleotide sequence shown as SEQ ID NO:1, or (f) a polypeptide encoded by the full-length coding region of the nucleotide sequence shown as SEQ ID NO:1.

12. An isolated polypeptide having (a) the amino acid sequence shown as SEQ ID NO:2, (b) the amino acid sequence shown as SEQ ID NO:2, lacking its associated signal peptide sequence, (c) an amino acid sequence of an extracellular domain of the polypeptide shown as SEQ ID NO:2, with its associated signal peptide sequence, (d) an amino acid sequence of an extracellular domain of the polypeptide shown as SEQ ID NO:2, lacking its associated signal peptide sequence, (e) an amino acid sequence encoded by the nucleotide sequence shown as SEQ ID NO:1, or (f) an amino acid sequence encoded by the full-length coding region of the nucleotide sequence shown as SEQ ID NO:1.

13. A chimeric polypeptide comprising the polypeptide of Claim 11 or 12 fused to a heterologous polypeptide.

14. The chimeric polypeptide of Claim 13, wherein said heterologous polypeptide is an epitope tag sequence or an Fc region of an immunoglobulin.

15. An isolated antibody that binds to a polypeptide having at least 80% amino acid sequence identity to (a) the polypeptide shown as SEQ ID NO:2, (b) the polypeptide shown as SEQ ID NO:2, lacking its associated signal peptide, (c) an extracellular domain of the polypeptide shown as SEQ ID NO:2, with its associated signal peptide, (d) an extracellular domain of the polypeptide shown as SEQ ID NO:2, lacking its associated signal peptide, (e) a polypeptide encoded by the nucleotide sequence shown as SEQ ID NO:1, or (f) a polypeptide encoded by the full-length coding region of the nucleotide sequence shown as SEQ ID NO:1.

16. An isolated antibody that binds to a polypeptide having (a) the amino acid sequence shown as SEQ ID NO:2, (b) the amino acid sequence shown as SEQ ID NO:2, lacking its associated signal peptide sequence, (c) an amino acid sequence of an extracellular domain of the polypeptide shown as SEQ ID NO:2, with its associated signal peptide sequence, (d) an amino acid sequence of an extracellular domain of the polypeptide shown as SEQ ID NO:2, lacking its associated signal peptide sequence, (e) an amino acid sequence encoded by the nucleotide sequence shown as SEQ ID NO:1, or (f) an amino acid sequence encoded by the full-length coding region of the nucleotide sequence shown as SEQ ID NO:1.

17. The antibody of Claim 15 or 16 which is a monoclonal antibody.

18. The antibody of Claim 15 or 16 which is an antibody fragment.

19. The antibody of Claim 15 or 16 which is a chimeric or a humanized antibody.

20. The antibody of Claim 15 or 16 which is conjugated to a growth inhibitory agent.

21. The antibody of Claim 15 or 16 which is conjugated to a cytotoxic agent.

22. The antibody of Claim 21, wherein the cytotoxic agent is selected from the group consisting of toxins, antibiotics, radioactive isotopes and nucleolytic enzymes.

23. The antibody of Claim 21, wherein the cytotoxic agent is a toxin.

24. The antibody of Claim 23, wherein the toxin is selected from the group consisting of maytansinoid, calicheamicin and auristatin.

25. The antibody of Claim 23, wherein the toxin is a maytansinoid.

26. The antibody of Claim 15 or 16 which is produced in bacteria.

27. The antibody of Claim 15 or 16 which is produced in CHO cells.

28. The antibody of Claim 15 or 16 which induces death of a cell to which it binds.

29. The antibody of Claim 15 or 16 which is detectably labeled.

30. An isolated nucleic acid having a nucleotide sequence that encodes the antibody of Claim 15 or 16.

31. An expression vector comprising the nucleic acid of Claim 30 operably linked to control sequences recognized by a host cell transformed with the vector.

32. A host cell comprising the expression vector of Claim 31.

33. The host cell of Claim 32 which is a CHO cell, an *E. coli* cell or a yeast cell.

34. A process for producing an antibody comprising culturing the host cell of Claim 32 under conditions suitable for expression of said antibody and recovering said antibody from the cell culture.

35. A composition of matter comprising (a) the polypeptide of Claim 11, (b) the polypeptide of Claim 12, (c) the chimeric polypeptide of Claim 13, (d) the antibody of Claim 15, or (e) the antibody of Claim 16, in combination with a carrier.

36. The composition of matter of Claim 35, wherein said carrier is a pharmaceutically acceptable carrier.

37. An article of manufacture comprising (a) a container; and (b) the composition of matter of Claim 35 contained within said container.

38. The article of manufacture of Claim 37 further comprising a label affixed to said container, or a package insert included with said container, referring to the use of said composition of matter for the therapeutic treatment of or the diagnostic detection of a cancer.

39. A method of inhibiting the growth of a cell that expresses a protein having at least 80% amino acid sequence identity to (a) the polypeptide shown as SEQ ID NO:2, (b) the polypeptide shown as SEQ ID NO:2, lacking its associated signal peptide, (c) an extracellular domain of the polypeptide shown as SEQ ID NO:2, with its associated signal peptide, (d) an extracellular domain of the polypeptide shown as SEQ ID NO:2, lacking its associated signal peptide, (e) a polypeptide encoded by the nucleotide sequence shown as SEQ ID NO:1, or (f) a polypeptide encoded by the full-length coding region of the nucleotide sequence shown as SEQ ID NO:1, said method comprising contacting said cell with an antibody that binds to said protein, the binding of said antibody to said protein thereby causing an inhibition of growth of said cell.

40. The method of Claim 39, wherein said antibody is a monoclonal antibody.

41. The method of Claim 39, wherein said antibody is an antibody fragment.

42. The method of Claim 39, wherein said antibody is a chimeric or a humanized antibody.

43. The method of Claim 39, wherein said antibody is conjugated to a growth inhibitory agent.

44. The method of Claim 39, wherein said antibody is conjugated to a cytotoxic agent.

45. The method of Claim 44, wherein said cytotoxic agent is selected from the group consisting of toxins, antibiotics, radioactive isotopes and nucleolytic enzymes.

46. The method of Claim 44, wherein the cytotoxic agent is a toxin.

47. The method of Claim 46, wherein the toxin is selected from the group consisting of maytansinoid, calicheamicin and auristatin.

48. The method of Claim 46, wherein the toxin is a maytansinoid.

49. The method of Claim 39, wherein said antibody is produced in bacteria.

50. The method of Claim 39, wherein said antibody is produced in CHO cells.

51. The method of Claim 39, wherein said cell is a cancer cell.

52. The method of Claim 51, wherein said cancer cell is further exposed to radiation treatment or a chemotherapeutic agent.

53. The method of Claim 51, wherein said cancer cell is selected from the group consisting of a breast cancer cell, a colorectal cancer cell, a lung cancer cell, an ovarian cancer cell, a central nervous system cancer cell, a liver cancer cell, a bladder cancer cell, a pancreatic cancer cell, a cervical cancer cell, a melanoma cell and a leukemia cell.

54. The method of Claim 51, wherein said protein is more abundantly expressed by said cancer cell as compared to a normal cell of the same tissue origin.

55. The method of Claim 39 which causes the death of said cell.

56. The method of Claim 39, wherein said protein has (a) the amino acid sequence shown as SEQ ID NO:2, (b) the amino acid sequence shown as SEQ ID NO:2, lacking its associated signal peptide sequence, (c) an amino acid sequence of an extracellular domain of the polypeptide shown as SEQ ID NO:2, with its associated signal peptide sequence, (d) an amino acid sequence of an extracellular domain of the polypeptide shown as SEQ ID NO:2, lacking its associated signal peptide sequence, (e) an amino acid sequence encoded by the nucleotide sequence shown as SEQ ID NO:1, or (f) an amino acid sequence encoded by the full-length coding region of the nucleotide sequence shown as SEQ ID NO:1.

57. A method of therapeutically treating a mammal having a cancerous tumor comprising cells that express a protein having at least 80% amino acid sequence identity to (a) the polypeptide shown as SEQ ID NO:2, (b) the polypeptide shown as SEQ ID NO:2, lacking its associated signal peptide, (c) an extracellular domain of the polypeptide shown as SEQ ID NO:2, with its associated signal peptide, (d) an extracellular domain of the polypeptide shown as SEQ ID NO:2, lacking its associated signal peptide, (e) a polypeptide encoded by the nucleotide sequence shown as SEQ ID NO:1; or (f) a polypeptide encoded by the full-length coding region of the nucleotide sequence shown as SEQ ID NO:1, said method comprising administering to said mammal a therapeutically effective amount of an antibody that binds to said protein, thereby effectively treating said mammal.

58. The method of Claim 57, wherein said antibody is a monoclonal antibody.

59. The method of Claim 57, wherein said antibody is an antibody fragment.

60. The method of Claim 57, wherein said antibody is a chimeric or a humanized antibody.

61. The method of Claim 57, wherein said antibody is conjugated to a growth inhibitory agent.

62. The method of Claim 57, wherein said antibody is conjugated to a cytotoxic agent.

63. The method of Claim 62, wherein said cytotoxic agent is selected from the group consisting of toxins, antibiotics, radioactive isotopes and nucleolytic enzymes.

64. The method of Claim 62, wherein the cytotoxic agent is a toxin.

65. The method of Claim 64, wherein the toxin is selected from the group consisting of maytansinoid, calicheamicin and auristatin.

66. The method of Claim 64, wherein the toxin is a maytansinoid.

67. The method of Claim 57, wherein said antibody is produced in bacteria.

68. The method of Claim 57, wherein said antibody is produced in CHO cells.

69. The method of Claim 57, wherein said tumor is further exposed to radiation treatment or a chemotherapeutic agent.

70. The method of Claim 57, wherein said tumor is a breast tumor, a colorectal tumor, a lung tumor, an ovarian tumor, a central nervous system tumor, a liver tumor, a bladder tumor, a pancreatic tumor, or a cervical tumor.

71. The method of Claim 57, wherein said protein is more abundantly expressed by the cancerous cells of said tumor as compared to a normal cell of the same tissue origin.

72. The method of Claim 57, wherein said protein has (a) the amino acid sequence shown as SEQ ID NO:2, (b) the amino acid sequence shown as SEQ ID NO:2, lacking its associated signal peptide sequence, (c) an amino acid sequence of an extracellular domain of the polypeptide shown as SEQ ID NO:2, with its associated signal peptide sequence, (d) an amino acid sequence of an extracellular domain of the polypeptide shown as SEQ ID NO:2, lacking its associated signal peptide sequence, (e) an amino acid sequence encoded by the nucleotide sequence shown as SEQ ID NO:1, or (f) an amino acid sequence encoded by the full-length coding region of the nucleotide sequence shown as SEQ ID NO:1.

73. A method of determining the presence of a protein in a sample suspected of containing said protein, wherein said protein has at least 80% amino acid sequence identity to (a) the polypeptide shown as SEQ ID NO:2, (b) the polypeptide shown as SEQ ID NO:2, lacking its associated signal peptide, (c) an extracellular domain of the polypeptide shown as SEQ ID NO:2, with its associated signal peptide, (d) an extracellular domain of the polypeptide shown as SEQ ID NO:2, lacking its associated signal peptide, (e) a polypeptide encoded by the nucleotide sequence shown as SEQ ID NO:1, or (f) a polypeptide encoded by the full-length coding region of the nucleotide sequence shown as SEQ ID NO:1, said method comprising exposing said sample to an antibody that binds to said protein and determining binding of said antibody to said protein in said sample, wherein binding of the antibody to said protein is indicative of the presence of said protein in said sample.

74. The method of Claim 73, wherein said sample comprises a cell suspected of expressing said protein.

75. The method of Claim 74, wherein said cell is a cancer cell.

76. The method of Claim 73, wherein said antibody is detectably labeled.

77. The method of Claim 73, wherein said protein has (a) the amino acid sequence shown as SEQ ID NO:2, (b) the amino acid sequence shown as SEQ ID NO:2, lacking its associated signal peptide sequence, (c) an amino acid sequence of an extracellular domain of the polypeptide shown as SEQ ID NO:2, with its associated signal peptide sequence, (d) an amino acid sequence of an extracellular domain of the polypeptide shown as SEQ ID NO:2, lacking its associated signal peptide sequence, (e) an amino acid sequence encoded by the nucleotide sequence shown as SEQ ID NO:1, or (f) an amino acid sequence encoded by the full-length coding region of the nucleotide sequence shown as SEQ ID NO:1.

78. A method of diagnosing the presence of a tumor in a mammal, said method comprising determining the level of expression of a gene encoding a protein having at least 80% amino acid sequence identity to (a) the polypeptide shown as SEQ ID NO:2, (b) the polypeptide shown as SEQ ID NO:2, lacking its associated signal peptide, (c) an extracellular domain of the polypeptide shown as SEQ ID NO:2, with its associated signal peptide, (d) an extracellular domain of the polypeptide shown as SEQ ID NO:2, lacking its associated signal peptide, (e) a polypeptide encoded by the nucleotide sequence shown as SEQ ID NO:1, or (f) a polypeptide encoded by the full-length coding region of the nucleotide sequence shown as SEQ ID NO:1, in a test sample of tissue cells obtained from said mammal and in a control sample of known normal cells of the same tissue origin, wherein a higher level of expression of said protein in the test sample, as compared to the control sample, is indicative of the presence of tumor in the mammal from which the test sample was obtained.

79. The method of Claim 78, wherein the step of determining the level of expression of a gene encoding said protein comprises employing an oligonucleotide in an in situ hybridization or RT-PCR analysis.

80. The method of Claim 78, wherein the step determining the level of expression of a gene encoding said protein comprises employing an antibody in an immunohistochemistry or Western blot analysis.

81. The method of Claim 78, wherein said protein has (a) the amino acid sequence shown as SEQ ID NO:2, (b) the amino acid sequence shown as SEQ ID NO:2, lacking its associated signal peptide sequence, (c) an amino acid sequence of an extracellular domain of the polypeptide shown as SEQ ID NO:2, with its associated signal peptide sequence, (d) an amino acid sequence of an extracellular domain of the polypeptide shown as SEQ ID NO:2, lacking its associated signal peptide sequence, (e) an amino acid sequence encoded by the nucleotide sequence shown as SEQ ID NO:1, or (f) an amino acid sequence encoded by the full-length coding region of the nucleotide sequence shown as SEQ ID NO:1.

82. A method of diagnosing the presence of a tumor in a mammal, said method comprising contacting a test sample of tissue cells obtained from said mammal with an antibody that binds to a protein having at least 80% amino acid sequence identity to (a) the polypeptide shown as SEQ ID NO:2, (b) the polypeptide shown as SEQ ID NO:2, lacking its associated signal peptide, (c) an extracellular domain of the polypeptide shown as SEQ ID NO:2, with its associated signal peptide, (d) an extracellular domain of the polypeptide shown as SEQ ID NO:2, lacking its associated signal peptide, (e) a polypeptide encoded by the nucleotide sequence shown as SEQ ID NO:1, or (f) a polypeptide encoded by the full-length coding region of the nucleotide sequence shown as SEQ ID NO:1, and detecting the formation of a complex between said antibody and said protein in the test sample, wherein the formation of a complex is indicative of the presence of a tumor in said mammal.

83. The method of Claim 82, wherein said antibody is detectably labeled.

84. The method of Claim 82, wherein said test sample of tissue cells is obtained from an individual suspected of having a cancerous tumor.

85. The method of Claim 82, wherein said protein has (a) the amino acid sequence shown as SEQ ID NO:2, (b) the amino acid sequence shown as SEQ ID NO:2, lacking its associated signal peptide sequence, (c) an amino acid sequence of an extracellular domain of the polypeptide shown as SEQ ID NO:2, with its associated signal peptide sequence, (d) an amino acid sequence of an extracellular domain of the polypeptide shown as SEQ ID NO:2, lacking its associated signal peptide sequence, (e) an amino acid sequence encoded by the nucleotide sequence shown as SEQ ID NO:1, or (f) an amino acid sequence encoded by the full-length coding region of the nucleotide sequence shown as SEQ ID NO:1.

86. A method for treating or preventing a cell proliferative disorder associated with increased expression or activity of a protein having at least 80% amino acid sequence identity to (a) the polypeptide shown as SEQ ID NO:2, (b) the polypeptide shown as SEQ ID NO:2, lacking its associated signal peptide, (c) an extracellular domain of the polypeptide shown as SEQ ID NO:2, with its associated signal peptide, (d) an extracellular domain of the polypeptide shown as SEQ ID NO:2, lacking its associated signal peptide, (e) a polypeptide encoded by the nucleotide sequence shown as SEQ ID NO:1, or (f) a polypeptide encoded by the full-length coding region of the nucleotide sequence shown as SEQ ID NO:1, said method comprising administering to a subject in need of such treatment an effective amount of an antagonist of said protein, thereby effectively treating or preventing said cell proliferative disorder.

87. The method of Claim 86, wherein said cell proliferative disorder is cancer.

88. The method of Claim 86, wherein said antagonist is an anti-TAT polypeptide antibody or antisense oligonucleotide.

89. A method of binding an antibody to a cell that expresses a protein having at least 80% amino acid sequence identity to (a) the polypeptide shown as SEQ ID NO:2, (b) the polypeptide shown as SEQ ID NO:2, lacking its associated signal peptide, (c) an extracellular domain of the polypeptide shown as SEQ ID NO:2, with its associated signal peptide, (d) an extracellular domain of the polypeptide shown as SEQ ID NO:2, lacking its associated signal peptide, (e) a polypeptide encoded by the nucleotide sequence shown as SEQ ID NO:1, or (f) a polypeptide encoded by the full-length coding region of the nucleotide sequence shown as SEQ ID NO:1, said method comprising contacting said cell with an antibody that binds to said protein and allowing the binding of the antibody to said protein to occur, thereby binding said antibody to said cell.

90. The method of Claim 89, wherein said antibody is a monoclonal antibody.

91. The method of Claim 89, wherein said antibody is an antibody fragment.

92. The method of Claim 89, wherein said antibody is a chimeric or a humanized antibody.

93. The method of Claim 89, wherein said antibody is conjugated to a growth inhibitory agent.

94. The method of Claim 89, wherein said antibody is conjugated to a cytotoxic agent.

95. The method of Claim 94, wherein said cytotoxic agent is selected from the group consisting of toxins, antibiotics, radioactive isotopes and nucleolytic enzymes.

96. The method of Claim 94, wherein the cytotoxic agent is a toxin.

97. The method of Claim 96, wherein the toxin is selected from the group consisting of maytansinoid, calicheamicin and auristatin.

98. The method of Claim 96, wherein the toxin is a maytansinoid.

99. The method of Claim 89, wherein said antibody is produced in bacteria.

100. The method of Claim 89, wherein said antibody is produced in CHO cells.

101. The method of Claim 89, wherein said cell is a cancer cell.

102. The method of Claim 101, wherein said cancer cell is further exposed to radiation treatment or a chemotherapeutic agent.

103. The method of Claim 101, wherein said cancer cell is selected from the group consisting of a breast cancer cell, a colorectal cancer cell, a lung cancer cell, an ovarian cancer cell, a central nervous system cancer cell, a liver cancer cell, a bladder cancer cell, a pancreatic cancer cell, a cervical cancer cell, a melanoma cell and a leukemia cell.

104. The method of Claim 103, wherein said protein is more abundantly expressed by said cancer cell as compared to a normal cell of the same tissue origin.

105. The method of Claim 89 which causes the death of said cell.

106. Use of a nucleic acid as claimed in any of Claims 1 to 5 or 30 in the preparation of a medicament for the therapeutic treatment or diagnostic detection of a cancer.

107. Use of a nucleic acid as claimed in any of Claims 1 to 5 or 30 in the preparation of a medicament for treating a tumor.

108. Use of a nucleic acid as claimed in any of Claims 1 to 5 or 30 in the preparation of a medicament for treatment or prevention of a cell proliferative disorder.

109. Use of an expression vector as claimed in any of Claims 6, 7 or 31 in the preparation of a medicament for the therapeutic treatment or diagnostic detection of a cancer.

110. Use of an expression vector as claimed in any of Claims 6, 7 or 31 in the preparation of medicament for treating a tumor.

111. Use of an expression vector as claimed in any of Claims 6, 7 or 31 in the preparation of a medicament for treatment or prevention of a cell proliferative disorder.

112. Use of a host cell as claimed in any of Claims 8, 9, 32, or 33 in the preparation of a medicament for the therapeutic treatment or diagnostic detection of a cancer.

113. Use of a host cell as claimed in any of Claims 8, 9, 32 or 33 in the preparation of a medicament for treating a tumor.

114. Use of a host cell as claimed in any of Claims 8, 9, 32 or 33 in the preparation of a medicament for treatment or prevention of a cell proliferative disorder.

115. Use of a polypeptide as claimed in any of Claims 11 to 14 in the preparation of a medicament for the therapeutic treatment or diagnostic detection of a cancer.

116. Use of a polypeptide as claimed in any of Claims 11 to 14 in the preparation of a medicament for treating a tumor.

117. Use of a polypeptide as claimed in any of Claims 11 to 14 in the preparation of a medicament for treatment or prevention of a cell proliferative disorder.

118. Use of an antibody as claimed in any of Claims 15 to 29 in the preparation of a medicament for the therapeutic treatment or diagnostic detection of a cancer.

119. Use of an antibody as claimed in any of Claims 15 to 29 in the preparation of a medicament for treating a tumor.

120. Use of an antibody as claimed in any of Claims 15 to 29 in the preparation of a medicament for treatment or prevention of a cell proliferative disorder.

121. Use of a composition of matter as claimed in any of Claims 35 or 36 in the preparation of a medicament for the therapeutic treatment or diagnostic detection of a cancer.

122. Use of a composition of matter as claimed in any of Claims 35 or 36 in the preparation of a medicament for treating a tumor.

123. Use of a composition of matter as claimed in any of Claims 35 or 36 in the preparation of a medicament for treatment or prevention of a cell proliferative disorder.

124. Use of an article of manufacture as claimed in any of Claims 37 or 38 in the preparation of a medicament for the therapeutic treatment or diagnostic detection of a cancer.

125. Use of an article of manufacture as claimed in any of Claims 37 or 38 in the preparation of a medicament for treating a tumor.

126. Use of an article of manufacture as claimed in any of Claims 37 or 38 in the preparation of a medicament for treatment or prevention of a cell proliferative disorder.

127. A method for inhibiting the growth of a cell, wherein the growth of said cell is at least in part dependent upon a growth potentiating effect of a protein having at least 80% amino acid sequence identity to (a) the polypeptide shown as SEQ ID NO:2, (b) the polypeptide shown as SEQ ID NO:2, lacking its associated signal peptide, (c) an extracellular domain of the polypeptide shown as SEQ ID NO:2, with its associated signal peptide, (d) an extracellular domain of the polypeptide shown as SEQ ID NO:2, lacking its associated signal peptide, (e) a polypeptide encoded by the nucleotide sequence shown as SEQ ID NO:1, or (f) a polypeptide encoded by the full-length coding region of the nucleotide sequence shown as SEQ ID NO:1, said method comprising contacting said protein with an antibody that binds to said protein, there by inhibiting the growth of said cell.

128. The method of Claim 127, wherein said cell is a cancer cell.

129. The method of Claim 127, wherein said protein is expressed by said cell.

130. The method of Claim 127, wherein the binding of said antibody to said protein antagonizes a cell growth-potentiating activity of said protein.

131. The method of Claim 127, wherein the binding of said antibody to said protein induces the death of said cell.

132. The method of Claim 127, wherein said antibody is a monoclonal antibody.

133. The method of Claim 127, wherein said antibody is an antibody fragment.

134. The method of Claim 127, wherein said antibody is a chimeric or a humanized antibody.

135. The method of Claim 127, wherein said antibody is conjugated to a growth inhibitory agent.

136. The method of Claim 127, wherein said antibody is conjugated to a cytotoxic agent.

137. The method of Claim 136, wherein said cytotoxic agent is selected from the group consisting of toxins, antibiotics, radioactive isotopes and nucleolytic enzymes.

138. The method of Claim 136, wherein the cytotoxic agent is a toxin.

139. The method of Claim 138, wherein the toxin is selected from the group consisting of maytansinoid, calicheamicin and auristatin.

140. The method of Claim 138, wherein the toxin is a maytansinoid.

141. The method of Claim 127, wherein said antibody is produced in bacteria.

142. The method of Claim 127, wherein said antibody is produced in CHO cells.

143. The method of Claim 127, wherein said protein has (a) the amino acid sequence shown as SEQ ID NO:2, (b) the amino acid sequence shown as SEQ ID NO:2, lacking its associated signal peptide sequence, (c) an amino acid sequence of an extracellular domain of the polypeptide shown as SEQ ID NO:2, with its associated signal peptide sequence, (d) an amino acid sequence of an extracellular domain of the polypeptide shown as SEQ ID NO:2, lacking its associated signal peptide sequence, (e) an amino acid sequence encoded by the nucleotide sequence shown as SEQ ID NO:1, or (f) an amino acid sequence encoded by the full-length coding region of the nucleotide sequence shown as SEQ ID NO:1.

144. A method of therapeutically treating a tumor in a mammal, wherein the growth of said tumor is at least in part dependent upon a growth potentiating effect of a protein having at least 80% amino acid sequence identity to (a) the polypeptide shown in as SEQ ID NO:2, (b) the polypeptide shown as SEQ ID NO:2, lacking its associated signal peptide, (c) an extracellular domain of the polypeptide shown as SEQ ID NO:2, with its associated signal peptide, (d) an extracellular domain of the polypeptide shown as SEQ ID NO:2, lacking its associated signal peptide, (e) a polypeptide encoded by the nucleotide sequence shown as SEQ ID NO:1, or (f) a polypeptide encoded by the full-length coding region of the nucleotide sequence shown as SEQ ID NO:1, said method comprising contacting said protein with an antibody that binds to said protein, thereby effectively treating said tumor.

145. The method of Claim 144, wherein said protein is expressed by cells of said tumor.

146. The method of Claim 144, wherein the binding of said antibody to said protein antagonizes a cell growth-potentiating activity of said protein.

147. The method of Claim 144, wherein said antibody is a monoclonal antibody.

148. The method of Claim 144, wherein said antibody is an antibody fragment.

149. The method of Claim 144, wherein said antibody is a chimeric or a humanized antibody.

150. The method of Claim 144, wherein said antibody is conjugated to a growth inhibitory agent.

151. The method of Claim 144, wherein said antibody is conjugated to a cytotoxic agent.

152. The method of Claim 151, wherein said cytotoxic agent is selected from the group consisting of toxins, antibiotics, radioactive isotopes and nucleolytic enzymes.

153. The method of Claim 151, wherein the cytotoxic agent is a toxin.

154. The method of Claim 153, wherein the toxin is selected from the group consisting of maytansinoid, calicheamicin and auristatin.

155. The method of Claim 153, wherein the toxin is a maytansinoid.

156. The method of Claim 144, wherein said antibody is produced in bacteria.

157. The method of Claim 144, wherein said antibody is produced in CHO cells.

158. The method of Claim 144, wherein said protein has (a) the amino acid sequence shown as SEQ ID NO:2, (b) the amino acid sequence shown as SEQ ID NO:2, lacking its associated signal peptide sequence, (c) an amino acid sequence of an extracellular domain of the polypeptide shown as SEQ ID NO:2, with its associated signal peptide sequence, (d) an amino acid sequence of an extracellular domain of the polypeptide shown as SEQ ID NO:2, lacking its associated signal peptide sequence, (e) an amino acid sequence encoded by the nucleotide sequence shown as SEQ ID NO:1, or (f) an amino acid sequence encoded by the full-length coding region of the nucleotide sequence shown as SEQ ID NO:1.

159. An isolated antibody that binds to the same epitope bound by an antibody of any of Claims 15 to 29.

160. The antibody of Claim 159 which is a monoclonal antibody.

161. The antibody of Claim 159 which is an antibody fragment.

162. The antibody of Claim 159 which is a chimeric or a humanized antibody.

163. The antibody of Claim 159 which is conjugated to a growth inhibitory agent.

164. The antibody of Claim 159 which is conjugated to a cytotoxic agent.

165. The antibody of Claim 164, wherein the cytotoxic agent is selected from the group consisting of toxins, antibiotics, radioactive isotopes and nucleolytic enzymes.

166. The antibody of Claim 164, wherein the cytotoxic agent is a toxin.

167. The antibody of Claim 166, wherein the toxin is selected from the group consisting of maytansinoid, calicheamicin and auristatin.

168. The antibody of Claim 166, wherein the toxin is a maytansinoid.

169. The antibody of Claim 159 which is produced in bacteria.

170. The antibody of Claim 159 which is produced in CHO cells.

171. The antibody of Claim 159 which induces death of a cell to which it binds.

172. The antibody of Claim 159 which is detectably labeled.

173. The antibody of Claim 159 which comprises at least one of the complementarity determining regions of any antibody of Claims 15-29.

174. A hybridoma cell which produces a monoclonal antibody that binds to a TAT polypeptide.

175. A method of identifying an antibody that binds to an epitope bound by any antibody of Claims 15 to 29, said method comprising determining the ability of a test antibody to block binding of any antibody of Claims 15 to 29, wherein the ability of said test antibody to block the binding of said any antibody of Claims 15 to 29 to a TAT polypeptide by at least 40% and at equal antibody concentrations is indicative of said test antibody being capable of binding to an epitope bound by said any antibody of Claims 15 to 29.

Yet further embodiments of the present invention will be evident to the skilled artisan upon a reading of the present specification.

BRIEF DESCRIPTION OF THE DRAWINGS

FIG. 1 shows a nucleotide sequence (SEQ ID NO:1) of a TAT419 cDNA, wherein SEQ ID NO:1 is a clone designated herein as "DNA96945". Putative start and stop codons are underlined.

FIG. 2 shows the amino acid sequence (SEQ ID NO:2) of a TAT419 polypeptide derived from the coding sequence of SEQ ID NO:1 shown in FIG. 1.

FIG. 3 shows the amino acid sequences of the full-length light chain of the murine 5E9 monoclonal antibody (SEQ ID NO:3) and the variable light chain of the murine 5E9 monoclonal antibody (SEQ ID NO:5).

FIG. 4 shows the amino acid sequences of the full-length heavy chain of the murine 5E9 monoclonal antibody (SEQ ID NO:4) and the variable heavy chain of the murine 5E9 monoclonal antibody (SEQ ID NO:6).

FIG. 5 shows the amino acid sequences of the full-length light chain of the humanized hu5E9.v1 antibody (SEQ ID NO:13) and the variable light chain of the humanized hu5E9.v1 antibody (SEQ ID NO:15).

FIG. 6 shows the amino acid sequences of the full-length heavy chain of the humanized hu5E9.v1 antibody (SEQ ID NO:14) and the variable heavy chain of the humanized hu5E9.v1 antibody (SEQ ID NO:16).

FIG. 7 shows the amino acid sequence of the variable heavy chain of the humanized hu5E9.v2 antibody (SEQ ID NO:17).

DETAILED DESCRIPTION OF THE INVENTION

I. Definitions

Figure 8:
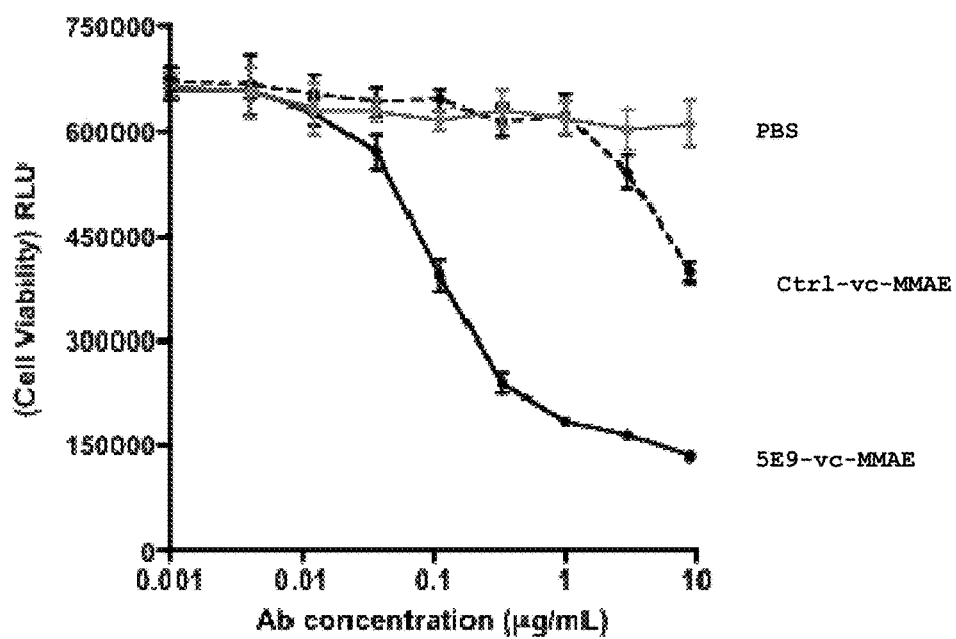
FIG. 8 shows in vitro killing of UACC257X2.2 cells with various concentrations of PBS (PBS), a vc-MMAE toxin-conjugated control antibody that does not bind to TAT419 polypeptide on the surface of live cells (Ctrl-vc-MMAE), and a vc-MMAE toxin-conjugated murine 5E9 monoclonal antibody (5E9-vc-MMAE).

The terms "TAT polypeptide" and "TAT" as used herein and when immediately followed by a numerical designation, refer to various polypeptides, wherein the complete designation (i.e., TAT/number) refers to specific polypeptide sequences as described herein. The terms "TAT/number polypeptide" and "TAT/number" wherein the term "number" is provided as an actual numerical designation as used herein encompass native sequence polypeptides, polypeptide variants and fragments of native sequence polypeptides and polypeptide variants (which are further defined herein). The TAT polypeptides described herein may be isolated from a variety of sources, such as from human tissue types or from another source, or prepared by recombinant or synthetic methods. The term "TAT polypeptide" refers to each individual TAT/number polypeptide disclosed herein. All disclosures in this specification which refer to the "TAT polypeptide" refer to each of the polypeptides individually as well as jointly. For example, descriptions of the preparation of, purification of, derivation of, formation of antibodies to or against, formation of TAT binding oligopeptides to or against, formation of TAT binding organic molecules to or against, administration of, compositions containing, treatment of a disease with, etc., pertain to each polypeptide of the invention individually. The term "TAT polypeptide" also includes variants of the TAT/number polypeptides disclosed herein. In one embodiment, a TAT419 polypeptide sequence is shown as SEQ ID NO:2.

A "native sequence TAT polypeptide" comprises a polypeptide having the same amino acid sequence as the corresponding TAT polypeptide derived from nature. Such native sequence TAT polypeptides can be isolated from nature or can be produced by recombinant or synthetic means. The term "native sequence TAT polypeptide" specifically encompasses naturally-occurring truncated or secreted forms of the specific TAT polypeptide (e.g., an extracellular domain sequence), naturally-occurring variant forms (e.g., alternatively spliced forms) and naturally-occurring allelic variants of the polypeptide. In certain embodiments of the invention, the native sequence TAT polypeptides disclosed herein are mature or full-length native sequence polypeptides comprising the full-length amino acids sequences shown in the accompanying figures. Start and stop codons (if indicated) are shown in bold font and underlined in the figures. Nucleic acid residues indicated as "N" or "X" in the accompanying figures are any nucleic acid residue. However, while the TAT polypeptides disclosed in the accompanying figures are shown to begin with methionine residues designated herein as amino acid position 1 in the figures, it is conceivable and possible that other methionine residues located either upstream or downstream from the amino acid position 1 in the figures may be employed as the starting amino acid residue for the TAT polypeptides.

The TAT polypeptide "extracellular domain" or "ECD" refers to a form of the TAT polypeptide which is essentially free of the transmembrane and cytoplasmic domains. Ordinarily, a TAT polypeptide ECD will have less than 1% of such transmembrane and/or cytoplasmic domains and preferably, will have less than 0.5% of such domains. It will be understood that any transmembrane domains identified for the TAT polypeptides of the present invention are identified pursuant to criteria routinely employed in the art for identifying that type of hydrophobic domain. The exact boundaries of a transmembrane domain may vary but most likely by no more than about 5 amino acids at either end of the domain as initially identified herein. Optionally, therefore, an extracellular domain of a TAT polypeptide may contain from about 5 or fewer amino acids on either side of the transmembrane domain/extracellular domain boundary as identified in the Examples or specification and such polypeptides, with or without the associated signal peptide, and nucleic acid encoding them, are contemplated by the present invention.

The approximate location of the "signal peptides" of the various TAT polypeptides disclosed herein may be shown in the present specification and/or the accompanying figures. It is noted, however, that the C-terminal boundary of a signal peptide may vary, but most likely by no more than about 5 amino acids on either side of the signal peptide C-terminal boundary as initially identified herein, wherein the C-terminal boundary of the signal peptide may be identified pursuant to criteria routinely employed in the art for identifying that type of amino acid sequence element (e.g., Nielsen et al., Prot. Eng. 10:1-6 (1997) and von Heinje et al., Nucl. Acids. Res. 14:4683-4690 (1986)). Moreover, it is also recognized that, in some cases, cleavage of a signal sequence from a secreted polypeptide is not entirely uniform, resulting in more than one secreted species. These mature polypeptides, where the signal peptide is cleaved within no more than about 5 amino acids on either side of the C-terminal boundary of the signal peptide as identified herein, and the polynucleotides encoding them, are contemplated by the present invention.

"TAT polypeptide variant" means a TAT polypeptide, preferably an active TAT polypeptide, as defined herein having at least about 80% amino acid sequence identity with a full-length native sequence TAT polypeptide sequence as disclosed herein, a TAT polypeptide sequence lacking the signal peptide as disclosed herein, an extracellular domain of a TAT polypeptide, with or without the signal peptide, as disclosed herein or any other fragment of a full-length TAT polypeptide sequence as disclosed herein (such as those encoded by a nucleic acid that represents only a portion of the complete coding sequence for a full-length TAT polypeptide). Such TAT polypeptide variants include, for instance, TAT polypeptides wherein one or more amino acid residues are added, or deleted, at the N- or C-terminus of the full-length native amino acid sequence. Ordinarily, a TAT polypeptide variant will have at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to a full-length native sequence TAT polypeptide sequence as disclosed herein, a TAT polypeptide sequence lacking the signal peptide as disclosed herein, an extracellular domain of a TAT polypeptide, with or without the signal peptide, as disclosed herein or any other specifically defined fragment of a full-length TAT polypeptide sequence as disclosed herein. Ordinarily, TAT variant polypeptides are at least about 10 amino acids in length, alternatively at least about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600 amino acids in length, or more. Optionally, TAT variant polypeptides will have no more than one conservative amino acid substitution as compared to the native TAT polypeptide sequence, alternatively no more than 2, 3, 4, 5, 6, 7, 8, 9, or 10 conservative amino acid substitution as compared to the native TAT polypeptide sequence.

"Percent (%) amino acid sequence identity" with respect to the TAT polypeptide sequences identified herein is defined as the percentage of amino acid residues in a candidate sequence that are identical with the amino acid residues in the specific TAT polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, wherein the complete source code for the ALIGN-2 program is provided in U.S. Pat. No. 7,160,985, which is herein incorporated by reference. The ALIGN-2 sequence comparison computer program was authored by Genentech, Inc. and the source code thereof has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction $X/Y$ where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

"TAT variant polynucleotide" or "TAT variant nucleic acid sequence" means a nucleic acid molecule which encodes a TAT polypeptide, preferably an active TAT polypeptide, as defined herein and which has at least about 80% nucleic acid sequence identity with a nucleotide acid sequence encoding a full-length native sequence TAT polypeptide sequence as disclosed herein, a full-length native sequence TAT polypeptide sequence lacking the signal peptide as disclosed herein, an extracellular domain of a TAT polypeptide, with or without the signal peptide, as disclosed herein or any other fragment of a full-length TAT polypeptide sequence as disclosed herein (such as those encoded by a nucleic acid that represents only a portion of the complete coding sequence for a full-length TAT polypeptide). Ordinarily, a TAT variant polynucleotide will have at least about 80% nucleic acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% nucleic acid sequence identity with a nucleic acid sequence encoding a full-length native sequence TAT polypeptide sequence as disclosed herein, a full-length native sequence TAT polypeptide sequence lacking the signal peptide as disclosed herein, an extracellular domain of a TAT polypeptide, with or without the signal sequence, as disclosed herein or any other fragment of a full-length TAT polypeptide sequence as disclosed herein. Variants do not encompass the native nucleotide sequence.

Ordinarily, TAT variant polynucleotides are at least about 5 nucleotides in length, alternatively at least about 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides in length, wherein in this context the term "about" means the referenced nucleotide sequence length plus or minus 10% of that referenced length.

"Percent (%) nucleic acid sequence identity" with respect to TAT-encoding nucleic acid sequences identified herein is defined as the percentage of nucleotides in a candidate sequence that are identical with the nucleotides in the TAT nucleic acid sequence of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. For purposes herein, however, % nucleic acid sequence identity values are generated using the sequence comparison computer program ALIGN-2, wherein the complete source code for the ALIGN-2 program is provided in U.S. Pat. No. 7,160,985, which is herein incorporated by reference. The ALIGN-2 sequence comparison computer program was authored by Genentech, Inc. and the source code thereof has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code. The ALIGN-2 program should be compiled for use on a UNIX operating system, preferably digital UNIX V4.0D. All sequence comparison parameters are set by the ALIGN-2 program and do not vary.

In situations where ALIGN-2 is employed for nucleic acid sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

In other embodiments, TAT variant polynucleotides are nucleic acid molecules that encode a TAT polypeptide and which are capable of hybridizing, preferably under stringent hybridization and wash conditions, to nucleotide sequences encoding a full-length TAT polypeptide as disclosed herein. TAT variant polypeptides may be those that are encoded by a TAT variant polynucleotide.

The term "full-length coding region" when used in reference to a nucleic acid encoding a TAT polypeptide refers to the sequence of nucleotides which encode the full-length TAT polypeptide of the invention (which is often shown between start and stop codons, inclusive thereof, in the accompanying figures). The term "full-length coding region" when used in reference to an ATCC deposited nucleic acid refers to the TAT polypeptide-encoding portion of the cDNA that is inserted into the vector deposited with the ATCC (which is often shown between start and stop codons, inclusive thereof, in the accompanying figures).

"Isolated," when used to describe the various TAT polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the TAT polypeptide natural environment will not be present. Ordinarily, however, isolated polypeptide will be prepared by at least one purification step.

An "isolated" TAT polypeptide-encoding nucleic acid or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) overnight hybridization in a solution that employs 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with a 10 minute wash at 42° C. in 0.2×SSC (sodium chloride/ sodium citrate) followed by a 10 minute high-stringency wash consisting of 0.1×SSC containing EDTA at 55° C.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" when used herein refers to a chimeric polypeptide comprising a TAT polypeptide or anti-TAT antibody fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

"Active" or "activity" for the purposes herein refers to form(s) of a TAT polypeptide which retain a biological and/or an immunological activity of native or naturally-occurring TAT, wherein "biological" activity refers to a biological function (either inhibitory or stimulatory) caused by a native or naturally-occurring TAT other than the ability to induce the production of an antibody against an antigenic epitope possessed by a native or naturally-occurring TAT and an "immunological" activity refers to the ability to induce the production of an antibody against an antigenic epitope possessed by a native or naturally-occurring TAT.

The term "antagonist" is used in the broadest sense, and includes any molecule that partially or fully blocks, inhibits, or neutralizes a biological activity of a native TAT polypeptide disclosed herein. In a similar manner, the term "agonist" is used in the broadest sense and includes any molecule that mimics a biological activity of a native TAT polypeptide disclosed herein. Suitable agonist or antagonist molecules specifically include agonist or antagonist antibodies or antibody fragments, fragments or amino acid sequence variants of native TAT polypeptides, peptides, antisense oligonucleotides, small organic molecules, etc. Methods for identifying agonists or antagonists of a TAT polypeptide may comprise contacting a TAT polypeptide with a candidate agonist or antagonist molecule and measuring a detectable change in one or more biological activities normally associated with the TAT polypeptide.

"Treating" or "treatment" or "alleviation" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for a TAT polypeptide-expressing cancer if, after receiving a therapeutic amount of an anti-TAT antibody, TAT binding oligopeptide or TAT binding organic molecule according to the methods of the present invention, the patient shows observable and/or measurable reduction in or absence of one or more of the following: reduction in the number of cancer cells or absence of the cancer cells; reduction in the tumor size; inhibition (i.e., slow to some extent and preferably stop) of cancer cell infiltration into peripheral organs including the spread of cancer into soft tissue and bone; inhibition (i.e., slow to some extent and preferably stop) of tumor metastasis; inhibition, to some extent, of tumor growth; and/or relief to some extent, one or more of the symptoms associated with the specific cancer; reduced morbidity and mortality, and improvement in quality of life issues. To the extent the anti-TAT antibody or TAT binding oligopeptide may prevent growth and/or kill existing cancer cells, it may be cytostatic and/or cytotoxic. Reduction of these signs or symptoms may also be felt by the patient.

The above parameters for assessing successful treatment and improvement in the disease are readily measurable by routine procedures familiar to a physician. For cancer therapy, efficacy can be measured, for example, by assessing the time to disease progression (TTP) and/or determining the response rate (RR). Metastasis can be determined by staging tests and by bone scan and tests for calcium level and other enzymes to determine spread to the bone. CT scans can also be done to look for spread to the pelvis and lymph nodes in the area. Chest X-rays and measurement of liver enzyme levels by known methods are used to look for metastasis to the lungs and liver, respectively. Other routine methods for monitoring the disease include transrectal ultrasonography (TRUS) and transrectal needle biopsy (TRNB).

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of the treatment of, alleviating the symptoms of or diagnosis of a cancer refers to any animal classified as a mammal, including humans, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

By "solid phase" or "solid support" is meant a non-aqueous matrix to which an antibody, TAT binding oligopeptide or TAT binding organic molecule of the present invention can adhere or attach. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as a TAT polypeptide, an antibody thereto or a TAT binding oligopeptide) to a mammal. The components of the liposome are commonly arranged in a bilayer formation, similar to the lipid arrangement of biological membranes.

A "small" molecule or "small" organic molecule is defined herein to have a molecular weight below about 500 Daltons.

An "effective amount" of a polypeptide, antibody, TAT binding oligopeptide, TAT binding organic molecule or an agonist or antagonist thereof as disclosed herein is an amount sufficient to carry out a specifically stated purpose. An "effective amount" may be determined empirically and in a routine manner, in relation to the stated purpose.

The term "therapeutically effective amount" refers to an amount of an antibody, polypeptide, TAT binding oligopeptide, TAT binding organic molecule or other drug effective to "treat" a disease or disorder in a subject or mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. See the definition herein of "treating". To the extent the drug may prevent growth and/or kill existing cancer cells, it may be cytostatic and/or cytotoxic.

A "growth inhibitory amount" of an anti-TAT antibody, TAT polypeptide, TAT binding oligopeptide or TAT binding organic molecule is an amount capable of inhibiting the growth of a cell, especially tumor, e.g., cancer cell, either in vitro or in vivo. A "growth inhibitory amount" of an anti-TAT antibody, TAT polypeptide, TAT binding oligopeptide or TAT binding organic molecule for purposes of inhibiting neoplastic cell growth may be determined empirically and in a routine manner.

A "cytotoxic amount" of an anti-TAT antibody, TAT polypeptide, TAT binding oligopeptide or TAT binding organic molecule is an amount capable of causing the destruction of a cell, especially tumor, e.g., cancer cell, either in vitro or in vivo. A "cytotoxic amount" of an anti-TAT antibody, TAT polypeptide, TAT binding oligopeptide or TAT binding organic molecule for purposes of inhibiting neoplastic cell growth may be determined empirically and in a routine manner.

The term "antibody" is used in the broadest sense and specifically covers, for example, single anti-TAT monoclonal antibodies (including agonist, antagonist, and neutralizing antibodies), anti-TAT antibody compositions with polyepitopic specificity, polyclonal antibodies, single chain anti-TAT antibodies, and fragments of anti-TAT antibodies (see below) as long as they exhibit the desired biological or immunological activity. The term "immunoglobulin" (Ig) is used interchangeable with antibody herein.

An "isolated antibody" is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic 4-chain antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to a H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the α and γ chains and four CH domains for μ and ε isotypes. Each L chain has at the N-terminus, a variable domain (VL) followed by a constant domain (CL) at its other end. The VL is aligned with the VH and the CL is aligned with the first constant domain of the heavy chain (CH1). Particular amino acid residues are believed to form an interface between the light chain and heavy chain variable domains. The pairing of a VH and VL together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated α, δ, ε, γ, and μ, respectively. The γ and α classes are further divided into subclasses on the basis of relatively minor differences in CH sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen binding and define specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222: 581-597 (1991), for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)). Chimeric antibodies of interest herein include "primatized" antibodies comprising variable domain antigen-binding sequences derived from a non-human primate (e.g. Old World Monkey, Ape etc), and human constant region sequences.

An "intact" antibody is one which comprises an antigen-binding site as well as a CL and at least heavy chain constant domains, CH1, CH2 and CH3. The constant domains may be native sequence constant domains (e.g. human native sequence constant domains) or amino acid sequence variant thereof. Preferably, the intact antibody has one or more effector functions.

"Antibody fragments" comprise a portion of an intact antibody, preferably the antigen binding or variable region of the intact antibody. Examples of antibody fragments include Fab, Fab', F(ab')2, and Fv fragments; diabodies; linear antibodies (see U.S. Pat. No. 5,641,870, Example 2; Zapata et al., Protein Eng. 8(10): 1057-1062 [1995]); single-chain antibody molecules; and multispecific antibodies formed from antibody fragments.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain (CH1). Each Fab fragment is monovalent with respect to antigen binding, i.e., it has a single antigen-binding site. Pepsin treatment of an antibody yields a single large F(ab')2 fragment which roughly corresponds to two disulfide linked Fab fragments having divalent antigen-binding activity and is still capable of cross-linking antigen. Fab' fragments differ from Fab fragments by having additional few residues at the carboxy terminus of the CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the VH and VL domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the VH and VL domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

A "species-dependent antibody," e.g., a mammalian anti-human IgE antibody, is an antibody which has a stronger binding affinity for an antigen from a first mammalian species than it has for a homologue of that antigen from a second mammalian species. Normally, the species-dependent antibody "bind specifically" to a human antigen (i.e., has a binding affinity (Kd) value of no more than about $1 \times 10^{-7}$ M, preferably no more than about $1 \times 10^{-8}$ and most preferably no more than about $1 \times 10^{-9}$ M) but has a binding affinity for a homologue of the antigen from a second non-human mammalian species which is at least about 50 fold, or at least about 500 fold, or at least about 1000 fold, weaker than its binding affinity for the human antigen. The species-dependent antibody can be of any of the various types of antibodies as defined above, but preferably is a humanized or human antibody.

The term "variable domain residue numbering as in Kabat" or "amino acid position numbering as in Kabat", and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g. residues 82a, 82b, and 82c, etc according to Kabat) after heavy chain FR residue 82. The Kabat numbering of residues may be determined for a given antibody by alignment at regions of homology of the sequence of the antibody with a "standard" Kabat numbered sequence.

The phrase "substantially similar," or "substantially the same", as used herein, denotes a sufficiently high degree of similarity between two numeric values (generally one associated with an antibody of the invention and the other associated with a reference/comparator antibody) such that one of skill in the art would consider the difference between the two values to be of little or no biological and/or statistical significance within the context of the biological characteristic measured by said values (e.g., Kd values). The difference between said two values is preferably less than about 50%, preferably less than about 40%, preferably less than about 30%, preferably less than about 20%, preferably less than about 10% as a function of the value for the reference/comparator antibody.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

In one embodiment, the "Kd" or "Kd value" according to this invention is measured by a radiolabeled antigen binding assay (RIA) performed with the Fab version of an antibody of interest and its antigen as described by the following assay that measures solution binding affinity of Fabs for antigen by equilibrating Fab with a minimal concentration of (125I)-labeled antigen in the presence of a titration series of unlabeled antigen, then capturing bound antigen with an anti-Fab antibody-coated plate (Chen, et al., (1999) J. Mol Biol 293:865-881). To establish conditions for the assay, microtiter plates (Dynex) are coated overnight with 5 ug/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbant plate (Nunc #269620), 100 pM or 26 pM [125I]-antigen are mixed with serial dilutions of a Fab of interest (e.g., consistent with assessment of an anti-VEGF antibody, Fab-12, in Presta et al., (1997) Cancer Res. 57:4593-4599). The Fab of interest is then incubated overnight; however, the incubation may continue for a longer period (e.g., 65 hours) to insure that equilibrium is reached. Thereafter, the mixtures are transferred to the capture plate for incubation at room temperature (e.g., for one hour). The solution is then removed and the plate washed eight times with 0.1% Tween-20 in PBS. When the plates have dried, 150 ul/well of scintillant (MicroScint-20; Packard) is added, and the plates are counted on a Topcount gamma counter (Packard) for ten minutes. Concentrations of each Fab that give less than or equal to 20% of maximal binding are chosen for use in competitive binding assays. According to another embodiment the Kd or Kd value is measured by using surface plasmon resonance assays using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 ug/ml (~0.2 uM) before injection at a flow rate of 5 ul/minute to achieve approximately 10 response units (RU) of coupled protein. Following the injection of antigen, 1M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 ul/min. Association rates (kon) and dissociation rates (koff) are calculated using a simple one-to-one Langmuir binding model (BIAcore Evaluation Software version 3.2) by simultaneous fitting the association and dissociation sensorgram. The equilibrium dissociation constant (Kd) is calculated as the ratio koff/kon. See, e.g., Chen, Y., et al., (1999) J. Mol Biol 293:865-881. If the on-rate exceeds 106 M-1 S-1 by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stir red cuvette.

An "on-rate" or "rate of association" or "association rate" or "kon" according to this invention can also be determined with the same surface plasmon resonance technique described above using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 ug/ml (~0.2 uM) before injection at a flow rate of 5 ul/minute to achieve approximately 10 response units (RU) of coupled protein. Following the injection of 1M ethanolamine to block unreacted groups. For kinetics measurements, two-fold serial dilutions of Fab (0.78 nM to 500 nM) are injected in PBS with 0.05% Tween 20 (PBST) at 25° C. at a flow rate of approximately 25 ul/min. Association rates (kon) and dissociation rates (koff) are calculated using a simple one-to-one Langmuir binding model (BIAcore Evaluation Software version 3.2) by simultaneous fitting the association and dissociation sensorgram. The equilibrium dissociation constant (Kd) was calculated as the ratio koff/kon. See, e.g., Chen, Y., et al., (1999) J. Mol Biol 293:865-881. However, if the on-rate exceeds 106 M-1 S-1 by the surface plasmon resonance assay above, then the on-rate is preferably determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stirred cuvette. The "Kd" or "Kd value" according to this invention is in one embodiment measured by a radiolabeled antigen binding assay (RIA) performed with the Fab version of the antibody and antigen molecule as described by the following assay that measures solution binding affinity of Fabs for antigen by equilibrating Fab with a minimal concentration of (125I)-labeled antigen in the presence of a titration series of unlabeled antigen, then capturing bound antigen with an anti-Fab antibody-coated plate (Chen, et al., (1999) J. Mol Biol 293:865-881). To establish conditions for the assay, microtiter plates (Dynex) are coated overnight with 5 ug/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbant plate (Nunc #269620), 100 pM or 26 pM [125I]-antigen are mixed with serial dilutions of a Fab of interest (consistent with assessment of an anti-VEGF antibody, Fab-12, in Presta et al., (1997) Cancer Res. 57:4593-4599). The Fab of interest is then incubated overnight; however, the incubation may continue for a longer period (e.g., 65 hours) to insure that equilibrium is reached. Thereafter, the mixtures are transferred to the capture plate for incubation at room temperature for one hour. The solution is then removed and the plate washed eight times with 0.1% Tween-20 in PBS. When the plates have dried, 150 ul/well of scintillant (MicroScint-20; Packard) is added, and the plates are counted on a Topcount gamma counter (Packard) for ten minutes. Concentrations of each Fab that give less than or equal to 20% of maximal binding are chosen for use in competitive binding assays. According to another embodiment, the Kd or Kd value is measured by using surface plasmon resonance assays using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 ug/ml (~0.2 uM) before injection at a flow rate of 5 ul/minute to achieve approximately 10 response units (RU) of coupled protein. Following the injection of antigen, 1M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 ul/min. Association rates (kon) and dissociation rates (koff) are calculated using a simple one-to-one Langmuir binding model (BIAcore Evaluation Software version 3.2) by simultaneous fitting the association and dissociation sensorgram. The equilibrium dissociation constant (Kd) is calculated as the ratio koff/kon. See, e.g., Chen, Y., et al., (1999) J. Mol Biol 293:865-881. If the on-rate exceeds 106 M-1 S-1 by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stir red cuvette.

In one embodiment, an "on-rate" or "rate of association" or "association rate" or "kon" according to this invention is determined with the same surface plasmon resonance technique described above using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 ug/ml (~0.2 uM) before injection at a flow rate of 5 ul/minute to achieve approximately 10 response units (RU) of coupled protein. Following the injection of 1M ethanolamine to block unreacted groups. For kinetics measurements, two-fold serial dilutions of Fab (0.78 nM to 500 nM) are injected in PBS with 0.05% Tween 20 (PBST) at 25° C. at a flow rate of approximately 25 ul/min. Association rates (kon) and dissociation rates (koff) are calculated using a simple one-to-one Langmuir binding model (BIAcore Evaluation Software version 3.2) by simultaneously fitting the association and dissociation sensorgram. The equilibrium dissociation constant (Kd) was calculated as the ratio koff/kon. See, e.g., Chen, Y., et al., (1999) J. Mol Biol 293:865-881. However, if the on-rate exceeds 106 M-1 S-1 by the surface plasmon resonance assay above, then the on-rate is preferably determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-Aminco spectrophotometer (ThermoSpectronic) with a stirred cuvette.

The phrase "substantially reduced," or "substantially different", as used herein, denotes a sufficiently high degree of difference between two numeric values (generally one associated with an antibody of the invention and the other associated with a reference/comparator antibody) such that one of skill in the art would consider the difference between the two values to be of statistical significance within the context of the biological characteristic measured by said values (e.g., Kd values, HAMA response). The difference between said two values is preferably greater than about 10%, preferably greater than about 20%, preferably greater than about 30%, preferably greater than about 40%, preferably greater than about 50% as a function of the value for the reference/comparator antibody.

An "antigen" is a predetermined antigen to which an antibody can selectively bind. The target antigen may be polypeptide, carbohydrate, nucleic acid, lipid, hapten or other naturally occurring or synthetic compound. Preferably, the target antigen is a polypeptide. An "acceptor human framework" for the purposes herein is a framework comprising the amino acid sequence of a VL or VH framework derived from a human immunoglobulin framework, or from a human consensus framework. An acceptor human framework "derived from" a human immunoglobulin framework or human consensus framework may comprise the same amino acid sequence thereof, or may contain pre-existing amino acid sequence changes. Where pre-existing amino acid changes are present, preferably no more than 5 and preferably 4 or less, or 3 or less, pre-existing amino acid changes are present. Where pre-existing amino acid changes are present in a VH, preferably those changes are only at three, two or one of positions 71H, 73H and 78H; for instance, the amino acid residues at those positions may be 71A, 73T and/or 78A. In one embodiment, the VL acceptor human framework is identical in sequence to the VL human immunoglobulin framework sequence or human consensus framework sequence.

Antibodies of the present invention may be able to compete for binding to the same epitope as is bound by a second antibody. Monoclonal antibodies are considered to share the "same epitope" if each blocks binding of the other by 40% or greater at the same antibody concentration in a standard in vitro antibody competition binding analysis.

A "human consensus framework" is a framework which represents the most commonly occurring amino acid residue in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al. In one embodiment, for the VL, the subgroup is subgroup kappa I as in Kabat et al. In one embodiment, for the VH, the subgroup is subgroup III as in Kabat et al.

A "VH subgroup III consensus framework" comprises the consensus sequence obtained from the amino acid sequences in variable heavy subgroup III of Kabat et al.

A "VL subgroup I consensus framework" comprises the consensus sequence obtained from the amino acid sequences in variable light kappa subgroup I of Kabat et al.

An "unmodified human framework" is a human framework which has the same amino acid sequence as the acceptor human framework, e.g. lacking human to non-human amino acid substitution(s) in the acceptor human framework.

An "altered hypervariable region" for the purposes herein is a hypervariable region comprising one or more (e.g. one to about 16) amino acid substitution(s) therein.

An "un-modified hypervariable region" for the purposes herein is a hypervariable region having the same amino acid sequence as a non-human antibody from which it was derived, i.e. one which lacks one or more amino acid substitutions therein.

The term "hypervariable region", "HVR", "HV" or "CDR", when used herein refers to the regions of an antibody variable domain which are hypervariable in sequence and/or form structurally defined loops. Generally, antibodies comprise six hypervariable regions; three in the VH (CDR-H1, CDR-H2, CDR-H3), and three in the VL (CDR-L1, CDR-L2, CDR-L3). A number of hypervariable region delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk J. Mol. Biol. 196:901-917 (1987)). The "contact" hypervariable regions are based on an analysis of the available complex crystal structures. The residues from each of these hypervariable regions are noted below. Unless otherwise denoted, Kabat numbering will be employed. Hypervariable region locations are generally as follows: amino acids 24-34 (CDR-L1), amino acids 49-56 (CDR-L2), amino acids 89-97 (CDR-L3), amino acids 26-35A (CDR-H1), amino acids 49-65 (CDR-H2), and amino acids 93-102 (CDR-H3).

Hypervariable regions may also comprise "extended hypervariable regions" as follows: amino acids 24-36 (L1), and amino acids 46-56 (L2) in the VL. The variable domain residues are numbered according to Kabat et al., supra for each of these definitions.

"Framework" or "FR" residues are those variable domain residues other than the hypervariable region residues as herein defined.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

An "affinity matured" antibody is one with one or more alterations in one or more CDRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. Bio/Technology 10:779-783 (1992) describes affinity maturation by VH and VL domain shuffling. Random mutagenesis of CDR and/or framework residues is described by: Barbas et al. Proc Nat. Acad. Sci, USA 91:3809-3813 (1994); Schier et al. Gene 169:147-155 (1995); Yelton et al. J. Immunol. 155:1994-2004 (1995); Jackson et al., J. Immunol. 154(7):3310-9 (1995); and Hawkins et al, J. Mol. Biol. 226:889-896 (1992).

A "blocking" antibody or an "antagonist" antibody is one which inhibits or reduces biological activity of the antigen it bind. Preferred blocking antibodies or antagonist antibodies substantially or completely inhibit the biological activity of the antigen.

A "TAT binding oligopeptide" is an oligopeptide that binds, preferably specifically, to a TAT polypeptide as described herein. TAT binding oligopeptides may be chemically synthesized using known oligopeptide synthesis methodology or may be prepared and purified using recombinant technology. TAT binding oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such oligopeptides that are capable of binding, preferably specifically, to a TAT polypeptide as described herein. TAT binding oligopeptides may be identified without undue experimentation using well known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750,373, 4,708,871, 4,833,092, 5,223,409, 5,403,484, 5,571,689, 5,663,143; PCT Publication Nos. WO 84/03506 and WO84/03564; Geysen et al., Proc. Natl. Acad. Sci. U.S.A., 81:3998-4002 (1984); Geysen et al., Proc. Natl. Acad. Sci. U.S.A., 82:178-182 (1985); Geysen et al., in Synthetic Peptides as Antigens, 130-149 (1986); Geysen et al., J. Immunol. Meth., 102:259-274 (1987); Schoofs et al., J. Immunol., 140:611-616 (1988), Cwirla, S. E. et al. (1990) Proc. Natl. Acad. Sci. USA, 87:6378; Lowman, H. B. et al. (1991) Biochemistry, 30:10832; Clackson, T. et al. (1991) Nature, 352: 624; Marks, J. D. et al. (1991), J. Mol. Biol., 222:581; Kang, A. S. et al. (1991) Proc. Natl. Acad. Sci. USA, 88:8363, and Smith, G. P. (1991) Current Opin. Biotechnol., 2:668).

A "TAT binding organic molecule" is an organic molecule other than an oligopeptide or antibody as defined herein that binds, preferably specifically, to a TAT polypeptide as described herein. TAT binding organic molecules may be identified and chemically synthesized using known methodology (see, e.g., PCT Publication Nos. WO00/00823 and WO00/39585). TAT binding organic molecules are usually less than about 2000 daltons in size, alternatively less than about 1500, 750, 500, 250 or 200 daltons in size, wherein such organic molecules that are capable of binding, preferably specifically, to a TAT polypeptide as described herein may be identified without undue experimentation using well known techniques. In this regard, it is noted that techniques for screening organic molecule libraries for molecules that are capable of binding to a polypeptide target are well known in the art (see, e.g., PCT Publication Nos. WO00/00823 and WO00/39585).

An antibody, oligopeptide or other organic molecule "which binds" an antigen of interest, e.g. a tumor-associated polypeptide antigen target, is one that binds the antigen with sufficient affinity such that the antibody, oligopeptide or other organic molecule is useful as a diagnostic and/or therapeutic agent in targeting a cell or tissue expressing the antigen, and does not significantly cross-react with other proteins. In such embodiments, the extent of binding of the antibody, oligopeptide or other organic molecule to a "non-target" protein will be less than about 10% of the binding of the antibody, oligopeptide or other organic molecule to its particular target protein as determined by fluorescence activated cell sorting (FACS) analysis or radioimmunoprecipitation (RIA). With regard to the binding of an antibody, oligopeptide or other organic molecule to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. In one embodiment, the term "specific binding" refers to binding where a molecule binds to a particular polypeptide or epitope on a particular polypeptide without substantially binding to any other polypeptide or polypeptide epitope.

An antibody, oligopeptide or other organic molecule that "inhibits the growth of tumor cells expressing a TAT polypeptide" or a "growth inhibitory" antibody, oligopeptide or other organic molecule is one which results in measurable growth inhibition of cancer cells expressing or overexpressing the appropriate TAT polypeptide. The TAT polypeptide may be a transmembrane polypeptide expressed on the surface of a cancer cell or may be a polypeptide that is produced and secreted by a cancer cell. Preferred growth inhibitory anti-TAT antibodies, oligopeptides or organic molecules inhibit growth of TAT-expressing tumor cells by greater than 20%, preferably from about 20% to about 50%, and even more preferably, by greater than 50% (e.g., from about 50% to about 100%) as compared to the appropriate control, the control typically being tumor cells not treated with the antibody, oligopeptide or other organic molecule being tested. In one embodiment, growth inhibition can be measured at an antibody concentration of about 0.1 to 30 µg/ml or about 0.5 nM to 200 nM in cell culture, where the growth inhibition is determined 1-10 days after exposure of the tumor cells to the antibody. Growth inhibition of tumor cells in vivo can be determined in various ways such as is described in the Experimental Examples section below. The antibody is growth inhibitory in vivo if administration of the anti-TAT antibody at about 1 µg/kg to about 100 mg/kg body weight results in reduction in tumor size or tumor cell proliferation within about 5 days to 3 months from the first administration of the antibody, preferably within about 5 to 30 days.

An antibody, oligopeptide or other organic molecule which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is usually one which overexpresses a TAT polypeptide. Preferably the cell is a tumor cell, e.g., a prostate, breast, ovarian, stomach, endometrial, lung, kidney, colon, bladder cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody, oligopeptide or other organic molecule which induces apoptosis is one which results in about 2 to 50 fold, preferably about 5 to 50 fold, and most preferably about 10 to 50 fold, induction of annexin binding relative to untreated cell in an annexin binding assay.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu Rev. Immunol. 9:457-92 (1991). To assess ADCC activity of a molecule of interest, an in vitro ADCC assay, such as that described in U.S. Pat. No. 5,500,362 or U.S. Pat. No. 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. (USA) 95:652-656 (1998).

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daëron, Annu Rev. Immunol. 15:203-234 (1997)). FcRs are reviewed in Ravetch and Kinet, Annu Rev. Immunol. 9:457-492 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976) and Kim et al., J. Immunol. 24:249 (1994)).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source, e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., J. Immunol. Methods 202:163 (1996), may be performed.

The terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, multiple myeloma and B-cell lymphoma, brain, as well as head and neck cancer, and associated metastases.

The terms "cell proliferative disorder" and "proliferative disorder" refer to disorders that are associated with some degree of abnormal cell proliferation. In one embodiment, the cell proliferative disorder is cancer.

"Tumor", as used herein, refers to all neoplastic cell growth and proliferation, whether malignant or benign, and all pre-cancerous and cancerous cells and tissues.

An antibody, oligopeptide or other organic molecule which "induces cell death" is one which causes a viable cell to become nonviable. The cell is one which expresses a TAT polypeptide, preferably a cell that overexpresses a TAT polypeptide as compared to a normal cell of the same tissue type. The TAT polypeptide may be a transmembrane polypeptide expressed on the surface of a cancer cell or may be a polypeptide that is produced and secreted by a cancer cell.

Preferably, the cell is a cancer cell, e.g., a breast, ovarian, stomach, endometrial, salivary gland, lung, kidney, colon, thyroid, pancreatic or bladder cell. Cell death in vitro may be determined in the absence of complement and immune effector cells to distinguish cell death induced by antibody-dependent cell-mediated cytotoxicity (ADCC) or complement dependent cytotoxicity (CDC). Thus, the assay for cell death may be performed using heat inactivated serum (i.e., in the absence of complement) and in the absence of immune effector cells. To determine whether the antibody, oligopeptide or other organic molecule is able to induce cell death, loss of membrane integrity as evaluated by uptake of propidium iodide (PI), trypan blue (see Moore et al. Cytotechnology 17:1-11 (1995)) or 7AAD can be assessed relative to untreated cells. Preferred cell death-inducing antibodies, oligopeptides or other organic molecules are those which induce PI uptake in the PI uptake assay in BT474 cells.

A "TAT-expressing cell" is a cell which expresses an endogenous or transfected TAT polypeptide either on the cell surface or in a secreted form. A "TAT-expressing cancer" is a cancer comprising cells that have a TAT polypeptide present on the cell surface or that produce and secrete a TAT polypeptide. A "TAT-expressing cancer" optionally produces sufficient levels of TAT polypeptide on the surface of cells thereof, such that an anti-TAT antibody, oligopeptide to other organic molecule can bind thereto and have a therapeutic effect with respect to the cancer. In another embodiment, a "TAT-expressing cancer" optionally produces and secretes sufficient levels of TAT polypeptide, such that an anti-TAT antibody, oligopeptide to other organic molecule antagonist can bind thereto and have a therapeutic effect with respect to the cancer. With regard to the latter, the antagonist may be an antisense oligonucleotide which reduces, inhibits or prevents production and secretion of the secreted TAT polypeptide by tumor cells. A cancer which "overexpresses" a TAT polypeptide is one which has significantly higher levels of TAT polypeptide at the cell surface thereof, or produces and secretes, compared to a noncancerous cell of the same tissue type. Such overexpression may be caused by gene amplification or by increased transcription or translation. TAT polypeptide overexpression may be determined in a diagnostic or prognostic assay by evaluating increased levels of the TAT protein present on the surface of a cell, or secreted by the cell (e.g., via an immunohistochemistry assay using anti-TAT antibodies prepared against an isolated TAT polypeptide which may be prepared using recombinant DNA technology from an isolated nucleic acid encoding the TAT polypeptide; FACS analysis, etc.). Alternatively, or additionally, one may measure levels of TAT polypeptide-encoding nucleic acid or mRNA in the cell, e.g., via fluorescent in situ hybridization using a nucleic acid based probe corresponding to a TAT-encoding nucleic acid or the complement thereof; (FISH; see WO98/45479 published October, 1998), Southern blotting, Northern blotting, or polymerase chain reaction (PCR) techniques, such as real time quantitative PCR (RT-PCR). One may also study TAT polypeptide overexpression by measuring shed antigen in a biological fluid such as serum, e.g., using antibody-based assays (see also, e.g., U.S. Pat. No. 4,933,294 issued Jun. 12, 1990; WO91/05264 published Apr. 18, 1991; U.S. Pat. No. 5,401,638 issued Mar. 28, 1995; and Sias et al., J. Immunol. Methods 132:73-80 (1990)). Aside from the above assays, various in vivo assays are available to the skilled practitioner. For example, one may expose cells within the body of the patient to an antibody which is optionally labeled with a detectable label, e.g., a radioactive isotope, and binding of the antibody to cells in the patient can be evaluated, e.g., by external scanning for radioactivity or by analyzing a biopsy taken from a patient previously exposed to the antibody.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

The word "label" when used herein refers to a detectable compound or composition which is conjugated directly or indirectly to the antibody, oligopeptide or other organic molecule so as to generate a "labeled" antibody, oligopeptide or other organic molecule. The label may be detectable by itself (e.g. radioisotope labels or fluorescent labels) or, in the case of an enzymatic label, may catalyze chemical alteration of a substrate compound or composition which is detectable.

The term "cytotoxic agent" as used herein refers to a substance that inhibits or prevents the function of cells and/or causes destruction of cells. The term is intended to include radioactive isotopes (e.g., At211, I131, I125, Y90, Re186, Re188, Sm153, Bi212, P32 and radioactive isotopes of Lu), chemotherapeutic agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaI1 (see, e.g., Agnew, Chem Intl. Ed. Engl., 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

A "growth inhibitory agent" when used herein refers to a compound or composition which inhibits growth of a cell, especially a TAT-expressing cancer cell, either in vitro or in vivo. Thus, the growth inhibitory agent may be one which significantly reduces the percentage of TAT-expressing cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Doxorubicin" is an anthracycline antibiotic. The full chemical name of doxorubicin is (8S-cis)-10-[(3-amino-2, 3,6-trideoxy-α-L-lyxo-hexapyranosyl)oxy]-7,8,9,10-tetrahydro-6,8,11-trihydroxy-8-(hydroxyacetyl)-1-methoxy-5,12-naphthacenedione.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1a, IL-2, IL-3, IL-4, IL-5, IL-6, IL-7, IL-8, IL-9, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

The term "package insert" is used to refer to instructions customarily included in commercial packages of therapeutic products, that contain information about the indications, usage, dosage, administration, contraindications and/or warnings concerning the use of such therapeutic products.

II. Compositions and Methods of the Invention

A. Anti-TAT Antibodies

In one embodiment, the present invention provides anti-TAT antibodies which may find use herein as therapeutic and/or diagnostic agents. Exemplary antibodies include polyclonal, monoclonal, humanized, bispecific, and heteroconjugate antibodies.

1. Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen (especially when synthetic peptides are used) to a protein that is immunogenic in the species to be immunized. For example, the antigen can be conjugated to keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, SOCl2, or R1N=C=NR, where R and R1 are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later, the animals are boosted with ⅕ to ⅒ the original amount of peptide or conjugate in Freund's complete adjuvant by subcutaneous injection at multiple sites. Seven to 14 days later, the animals are bled and the serum is assayed for antibody titer. Animals are boosted until the titer plateaus. Conjugates also can be made in recombinant cell culture as protein fusions. Also, aggregating agents such as alum are suitably used to enhance the immune response.

2. Monoclonal Antibodies

Monoclonal antibodies may be made using the hybridoma method first described by Kohler et al., Nature, 256:495 (1975), or may be made by recombinant DNA methods (U.S. Pat. No. 4,816,567).

In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium which medium preferably contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as those derived from MOPC-21 and MPC-11 mouse tumors available from the Salk Institute Cell Distribution Center, San Diego, Calif. USA, and SP-2 and derivatives e.g., X63-Ag8-653 cells available from the American Type Culture Collection, Manassas, Va., USA. Human myeloma and mouse-human heteromyeloma cell lines also have been described for the production of human monoclonal antibodies (Kozbor, J. Immunol., 133:3001 (1984); and Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis described in Munson et al., Anal. Biochem., 107:220 (1980).

Once hybridoma cells that produce antibodies of the desired specificity, affinity, and/or activity are identified, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal e.g., by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as E. coli cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., Curr. Opinion in Immunol., 5:256-262 (1993) and Plückthun, Immunol. Revs. 130:151-188 (1992).

In a further embodiment, monoclonal antibodies or antibody fragments can be isolated from antibody phage libraries generated using the techniques described in McCafferty et al., Nature, 348:552-554 (1990). Clackson et al., Nature, 352:624-628 (1991) and Marks et al., J. Mol. Biol., 222: 581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res. 21:2265-2266 (1993)). Thus, these techniques are viable alternatives to traditional monoclonal antibody hybridoma techniques for isolation of monoclonal antibodies.

The DNA that encodes the antibody may be modified to produce chimeric or fusion antibody polypeptides, for example, by substituting human heavy chain and light chain constant domain (CH and CL) sequences for the homologous murine sequences (U.S. Pat. No. 4,816,567; and Morrison, et al., Proc. Natl. Acad. Sci. USA, 81:6851 (1984)), or by fusing the immunoglobulin coding sequence with all or part of the coding sequence for a non-immunoglobulin polypeptide (heterologous polypeptide). The non-immunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

3. Human and Humanized Antibodies

The anti-TAT antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., Nature, 321:522-525 (1986); Riechmann et al., Nature, 332:323-327 (1988); Verhoeyen et al., Science, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity and HAMA response (human anti-mouse antibody) when the antibody is intended for human therapeutic use. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., J. Immunol. 151:2296 (1993); Chothia et al., J. Mol. Biol., 196:901 (1987)). Another method uses a particular framework region derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol. 151:2623 (1993)).

It is further important that antibodies be humanized with retention of high binding affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Various forms of a humanized anti-TAT antibody are contemplated. For example, the humanized antibody may be an antibody fragment, such as a Fab, which is optionally conjugated with one or more cytotoxic agent(s) in order to generate an immunoconjugate. Alternatively, the humanized antibody may be an intact antibody, such as an intact IgG1 antibody.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggemann et al., Year in Immuno. 7:33 (1993); U.S. Pat. Nos. 5,545,806, 5,569,825, 5,591,669 (all of GenPharm); U.S. Pat. No. 5,545,807; and WO 97/17852.

Alternatively, phage display technology (McCafferty et al., Nature 348:552-553 [1990]) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S. and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-597 (1991), or Griffith et al., EMBO J. 12:725-734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275).

4. Antibody Fragments

In certain circumstances there are advantages of using antibody fragments, rather than whole antibodies. The smaller size of the fragments allows for rapid clearance, and may lead to improved access to solid tumors.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from E. coli, thus allowing the facile production of large amounts of these fragments. Antibody fragments can be isolated from the antibody phage libraries discussed above. Alternatively, Fab'-SH fragments can be directly recovered from E. coli and chemically coupled to form F(ab')2 fragments (Carter et al., Bio/Technology 10:163-167 (1992)). According to another approach, F(ab')2 fragments can be isolated directly from recombinant host cell culture. Fab and F(ab')2 fragment with increased in vivo half-life comprising a salvage receptor binding epitope residues are described in U.S. Pat. No. 5,869,046. Other techniques for the production of antibody fragments will be apparent to the skilled practitioner. In other embodiments, the antibody of choice is a single chain Fv fragment (scFv). See WO 93/16185; U.S. Pat. No. 5,571,894; and U.S. Pat. No. 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody", e.g., as described in U.S. Pat. No. 5,641,870 for example. Such linear antibody fragments may be monospecific or bispecific.

5. Bispecific Antibodies

Bispecific antibodies are antibodies that have binding specificities for at least two different epitopes. Exemplary bispecific antibodies may bind to two different epitopes of a TAT protein as described herein. Other such antibodies may combine a TAT binding site with a binding site for another protein. Alternatively, an anti-TAT arm may be combined with an arm which binds to a triggering molecule on a leukocyte such as a T-cell receptor molecule (e.g. CD3), or Fc receptors for IgG (FcγR), such as FcγRI (CD64), FcγRII (CD32) and FcγRIII (CD16), so as to focus and localize cellular defense mechanisms to the TAT-expressing cell. Bispecific antibodies may also be used to localize cytotoxic agents to cells which express TAT. These antibodies possess a TAT-binding arm and an arm which binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., F(ab')2 bispecific antibodies).

WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (Millstein et al., Nature 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J. 10:3655-3659 (1991).

According to a different approach, antibody variable domains with the desired binding specificities (antibody-antigen combining sites) are fused to immunoglobulin constant domain sequences. Preferably, the fusion is with an Ig heavy chain constant domain, comprising at least part of the hinge, CH2, and CH3 regions. It is preferred to have the first heavy-chain constant region (CH1) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the CH3 domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science 229:81 (1985) describe a procedure wherein intact antibodies are proteolytically cleaved to generate F(ab')2 fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from E. coli, which can be chemically coupled to form bispecific antibodies. Shalaby et al., J. Exp. Med. 175: 217-225 (1992) describe the production of a fully humanized bispecific antibody F(ab')2 molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a VH connected to a VL by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

Antibodies with more than two valencies are contemplated. For example, trispecific antibodies can be prepared. Tutt et al., J. Immunol. 147:60 (1991).

6. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents.

For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

7. Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

8. Effector Function Engineering

It may be desirable to modify the antibody of the invention with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176:1191-1195 (1992) and Shopes, B. J. Immunol. 148:2918-2922 (1992). Homodimeric antibodies with enhanced anti-tumor activity may also be prepared using heterobifunctional cross-linkers as described in Wolff et al., Cancer Research 53:2560-2565 (1993). Alternatively, an antibody can be engineered which has dual Fc regions and may thereby have enhanced complement lysis and ADCC capabilities. See Stevenson et al., Anti-Cancer Drug Design 3:219-230 (1989). To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule.

9. Immunoconjugates

The invention also pertains to immunoconjugates comprising an antibody conjugated to a cytotoxic agent such as a chemotherapeutic agent, a growth inhibitory agent, a toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include 212Bi, 131I, 131In, 90Y, and 186Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, a trichothene, and CC1065, and the derivatives of these toxins that have toxin activity, are also contemplated herein.

Maytansine and Maytansinoids

In one preferred embodiment, an anti-TAT antibody (full length or fragments) of the invention is conjugated to one or more maytansinoid molecules.

Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, the disclosures of which are hereby expressly incorporated by reference.

Maytansinoid-Antibody Conjugates

In an attempt to improve their therapeutic index, maytansine and maytansinoids have been conjugated to antibodies specifically binding to tumor cell antigens. Immunoconjugates containing maytansinoids and their therapeutic use are disclosed, for example, in U.S. Pat. Nos. 5,208,020, 5,416,064 and European Patent EP 0 425 235 B1, the disclosures of which are hereby expressly incorporated by reference. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., Cancer Research 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansonoid conjugate was tested in vitro on the human breast cancer cell line SK-BR-3, which expresses 3×105 HER-2 surface antigens per cell. The drug conjugate achieved a degree of cytotoxicity similar to the free maytansonid drug, which could be increased by increasing the number of maytansinoid molecules per antibody molecule. The A7-maytansinoid conjugate showed low systemic cytotoxicity in mice.

Anti-TAT Polypeptide Antibody-Maytansinoid Conjugates (Immunoconjugates)

Anti-TAT antibody-maytansinoid conjugates are prepared by chemically linking an anti-TAT antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0425235B1, Chari et al., Cancer Research 52:127-131 (1992), and U.S. patent application Ser. No. 10/960,602, filed Oct. 8, 2004, the disclosures of which are hereby expressly incorporated by reference. Antibody-maytansinoid conjugates comprising the linker component SMCC may be prepared as disclosed in U.S. patent application Ser. No. 10/960,602, filed Oct. 8, 2004. The linking groups include disulfide groups, thioether groups, acid labile groups, photolabile groups, peptidase labile groups, or esterase labile groups, as disclosed in the above-identified patents, disulfide and thioether groups being preferred. Additional linking groups are described and exemplified herein.

Conjugates of the antibody and maytansinoid may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio)propionate (SPDP) (Carlsson et al., Biochem. J. 173:723-737 [1978]) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hyrdoxymethyl, the C-15 position modified with a hydroxyl group, and the C-20 position having a hydroxyl group. In a preferred embodiment, the linkage is formed at the C-3 position of maytansinol or a maytansinol analogue.

Auristatins and Dolostatins

In some embodiments, the immunoconjugate comprises an antibody of the invention conjugated to dolastatins or dolostatin peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF (i.e., MMAE and MMAF), disclosed in "Senter et al, Proceedings of the American Association for Cancer Research, Volume 45, Abstract Number 623, presented Mar. 28, 2004, the disclosure of which is expressly incorporated by reference in its entirety.

Typically, peptide-based drug moieties can be prepared by forming a peptide bond between two or more amino acids and/or peptide fragments. Such peptide bonds can be prepared, for example, according to the liquid phase synthesis method (see E. Schröder and K. Lübke, "The Peptides", volume 1, pp 76-136, 1965, Academic Press) that is well known in the field of peptide chemistry. The auristatin/dolastatin drug moieties may be prepared according to the methods of: U.S. Pat. No. 5,635,483; U.S. Pat. No. 5,780,588; Pettit et al (1989) J. Am. Chem. Soc. 111:5463-5465; Pettit et al (1998) Anti-Cancer Drug Design 13:243-277; Pettit, G. R., et al. Synthesis, 1996, 719-725; Pettit et al (1996) J. Chem. Soc. Perkin Trans. 1 5:859-863; and Doronina (2003) Nat Biotechnol 21(7):778-784.

Calicheamicin

Another immunoconjugate of interest comprises an anti-TAT antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, γ1I, α2I, α3I, N-acetyl-γ1I, PSAG and θI1 (Hinman et al., Cancer Research 53:3336-3342 (1993), Lode et al., Cancer Research 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to the anti-TAT antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated anti-TAT antibodies. Examples include At211, I131, I125, Y90, Re186, Re188, Sm153, Bi212, P32, Pb212 and radioactive isotopes of Lu. When the conjugate is used for diagnosis, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as tc99m or I123, Re186, Re188 and In111 can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

The compounds of the invention expressly contemplate, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

Alternatively, a fusion protein comprising the anti-TAT antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

10. Immunoliposomes

The anti-TAT antibodies disclosed herein may also be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., Proc. Natl. Acad. Sci. USA 82:3688 (1985); Hwang et al., Proc. Natl. Acad. Sci. USA 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem. 257:286-288 (1982) via a disulfide interchange reaction. A chemotherapeutic agent is optionally contained within the liposome. See Gabizon et al., J. National Cancer Inst. 81(19):1484 (1989).

B. TAT Binding Oligopeptides

TAT binding oligopeptides of the present invention are oligopeptides that bind, preferably specifically, to a TAT polypeptide as described herein. TAT binding oligopeptides may be chemically synthesized using known oligopeptide synthesis methodology or may be prepared and purified using recombinant technology. TAT binding oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such oligopeptides that are capable of binding, preferably specifically, to a TAT polypeptide as described herein. TAT binding oligopeptides may be identified without undue experimentation using well known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750,373, 4,708,871, 4,833,092, 5,223,409, 5,403,484, 5,571,689, 5,663,143; PCT Publication Nos. WO 84/03506 and WO84/03564; Geysen et al., Proc. Natl. Acad. Sci. U.S.A., 81:3998-4002 (1984); Geysen et al., Proc. Natl. Acad. Sci. U.S.A., 82:178-182 (1985); Geysen et al., in Synthetic Peptides as Antigens, 130-149 (1986); Geysen et al., J. Immunol. Meth., 102:259-274 (1987); Schoofs et al., J. Immunol., 140:611-616 (1988); Cwirla, S. E. et al. (1990) Proc. Natl. Acad. Sci. USA, 87:6378; Lowman, H. B. et al. (1991) Biochemistry, 30:10832; Clackson, T. et al. (1991) Nature, 352: 624; Marks, J. D. et al. (1991), J. Mol. Biol., 222:581; Kang, A. S. et al. (1991) Proc. Natl. Acad. Sci. USA, 88:8363, and Smith, G. P. (1991) Current Opin. Biotechnol., 2:668).

In this regard, bacteriophage (phage) display is one well known technique which allows one to screen large oligopeptide libraries to identify member(s) of those libraries which are capable of specifically binding to a polypeptide target. Phage display is a technique by which variant polypeptides are displayed as fusion proteins to the coat protein on the surface of bacteriophage particles (Scott, J. K. and Smith, G. P. (1990) Science 249: 386). The utility of phage display lies in the fact that large libraries of selectively randomized protein variants (or randomly cloned cDNAs) can be rapidly and efficiently sorted for those sequences that bind to a target molecule with high affinity. Display of peptide (Cwirla, S. E. et al. (1990) Proc. Natl. Acad. Sci. USA, 87:6378) or protein (Lowman, H. B. et al. (1991) Biochemistry, 30:10832; Clackson, T. et al. (1991) Nature, 352: 624; Marks, J. D. et al. (1991), J. Mol. Biol., 222:581; Kang, A. S. et al. (1991) Proc. Natl. Acad. Sci. USA, 88:8363) libraries on phage have been used for screening millions of polypeptides or oligopeptides for ones with specific binding properties (Smith, G. P. (1991) Current Opin. Biotechnol., 2:668). Sorting phage libraries of random mutants requires a strategy for constructing and propagating a large number of variants, a procedure for affinity purification using the target receptor, and a means of evaluating the results of binding enrichments. U.S. Pat. Nos. 5,223,409, 5,403,484, 5,571,689, and 5,663,143.

Although most phage display methods have used filamentous phage, lambdoid phage display systems (WO 95/34683; U.S. Pat. No. 5,627,024), T4 phage display systems (Ren et al., Gene, 215: 439 (1998); Zhu et al., Cancer Research, 58(15): 3209-3214 (1998); Jiang et al., Infection & Immunity, 65(11): 4770-4777 (1997); Ren et al., Gene, 195(2): 303-311 (1997); Ren, Protein Sci., 5: 1833 (1996); Efimov et al., Virus Genes, 10: 173 (1995) and T7 phage display systems (Smith and Scott, Methods in Enzymology, 217: 228-257 (1993); U.S. Pat. No. 5,766,905) are also known.

Many other improvements and variations of the basic phage display concept have now been developed. These improvements enhance the ability of display systems to screen peptide libraries for binding to selected target molecules and to display functional proteins with the potential of screening these proteins for desired properties. Combinatorial reaction devices for phage display reactions have been developed (WO 98/14277) and phage display libraries have been used to analyze and control bimolecular interactions (WO 98/20169; WO 98/20159) and properties of constrained helical peptides (WO 98/20036). WO 97/35196 describes a method of isolating an affinity ligand in which a phage display library is contacted with one solution in which the ligand will bind to a target molecule and a second solution in which the affinity ligand will not bind to the target molecule, to selectively isolate binding ligands. WO 97/46251 describes a method of biopanning a random phage display library with an affinity purified antibody and then isolating binding phage, followed by a micropanning process using microplate wells to isolate high affinity binding phage. The use of Staphlylococcus aureus protein A as an affinity tag has also been reported (Li et al. (1998) Mol Biotech., 9:187). WO 97/47314 describes the use of substrate subtraction libraries to distinguish enzyme specificities using a combinatorial library which may be a phage display library. A method for selecting enzymes suitable for use in detergents using phage display is described in WO 97/09446. Additional methods of selecting specific binding proteins are described in U.S. Pat. Nos. 5,498,538, 5,432,018, and WO 98/15833.

Methods of generating peptide libraries and screening these libraries are also disclosed in U.S. Pat. Nos. 5,723,286, 5,432,018, 5,580,717, 5,427,908, 5,498,530, 5,770,434, 5,734,018, 5,698,426, 5,763,192, and 5,723,323.

C. TAT Binding Organic Molecules

TAT binding organic molecules are organic molecules other than oligopeptides or antibodies as defined herein that bind, preferably specifically, to a TAT polypeptide as described herein. TAT binding organic molecules may be identified and chemically synthesized using known methodology (see, e.g., PCT Publication Nos. WO00/00823 and WO00/39585). TAT binding organic molecules are usually less than about 2000 daltons in size, alternatively less than about 1500, 750, 500, 250 or 200 daltons in size, wherein such organic molecules that are capable of binding, preferably specifically, to a TAT polypeptide as described herein may be identified without undue experimentation using well known techniques. In this regard, it is noted that techniques for screening organic molecule libraries for molecules that are capable of binding to a polypeptide target are well known in the art (see, e.g., PCT Publication Nos. WO00/00823 and WO00/39585). TAT binding organic molecules may be, for example, aldehydes, ketones, oximes, hydrazones, semicarbazones, carbazides, primary amines, secondary amines, tertiary amines, N-substituted hydrazines, hydrazides, alcohols, ethers, thiols, thioethers, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, aziridines, isocyanates, sulfonyl chlorides, diazo compounds, acid chlorides, or the like.

D. Screening for Anti-TAT Antibodies, TAT Binding Oligopeptides and TAT Binding Organic Molecules with the Desired Properties Techniques for generating antibodies, oligopeptides and organic molecules that bind to TAT polypeptides have been described above. One may further select antibodies, oligopeptides or other organic molecules with certain biological characteristics, as desired.

The growth inhibitory effects of an anti-TAT antibody, oligopeptide or other organic molecule of the invention may be assessed by methods known in the art, e.g., using cells which express a TAT polypeptide either endogenously or following transfection with the TAT gene. For example, appropriate tumor cell lines and TAT-transfected cells may treated with an anti-TAT monoclonal antibody, oligopeptide or other organic molecule of the invention at various concentrations for a few days (e.g., 2-7) days and stained with crystal violet or MTT or analyzed by some other colorimetric assay. Another method of measuring proliferation would be by comparing 3H-thymidine uptake by the cells treated in the presence or absence an anti-TAT antibody, TAT binding oligopeptide or TAT binding organic molecule of the invention. After treatment, the cells are harvested and the amount of radioactivity incorporated into the DNA quantitated in a scintillation counter. Appropriate positive controls include treatment of a selected cell line with a growth inhibitory antibody known to inhibit growth of that cell line. Growth inhibition of tumor cells in vivo can be determined in various ways known in the art. Preferably, the tumor cell is one that overexpresses a TAT polypeptide. Preferably, the anti-TAT antibody, TAT binding oligopeptide or TAT binding organic molecule will inhibit cell proliferation of a TAT-expressing tumor cell in vitro or in vivo by about 25-100% compared to the untreated tumor cell, more preferably, by about 30-100%, and even more preferably by about 50-100% or 70-100%, in one embodiment, at an antibody concentration of about 0.5 to 30 µg/ml. Growth inhibition can be measured at an antibody concentration of about 0.5 to 30 µg/ml or about 0.5 nM to 200 nM in cell culture, where the growth inhibition is determined 1-10 days after exposure of the tumor cells to the antibody. The antibody is growth inhibitory in vivo if administration of the anti-TAT antibody at about 1 µg/kg to about 100 mg/kg body weight results in reduction in tumor size or reduction of tumor cell proliferation within about 5 days to 3 months from the first administration of the antibody, preferably within about 5 to 30 days.

To select for an anti-TAT antibody, TAT binding oligopeptide or TAT binding organic molecule which induces cell death, loss of membrane integrity as indicated by, e.g., propidium iodide (PI), trypan blue or 7AAD uptake may be assessed relative to control. A PI uptake assay can be performed in the absence of complement and immune effector cells. TAT polypeptide-expressing tumor cells are incubated with medium alone or medium containing the appropriate anti-TAT antibody (e.g, at about 10 µg/ml), TAT binding oligopeptide or TAT binding organic molecule. The cells are incubated for a 3 day time period. Following each treatment, cells are washed and aliquoted into 35 mm strainer-capped 12×75 tubes (1 ml per tube, 3 tubes per treatment group) for removal of cell clumps. Tubes then receive PI (10 µg/ml). Samples may be analyzed using a FACSCAN® flow cytometer and FACSCONVERT® CellQuest software (Becton Dickinson). Those anti-TAT antibodies, TAT binding oligopeptides or TAT binding organic molecules that induce statistically significant levels of cell death as determined by PI uptake may be selected as cell death-inducing anti-TAT antibodies, TAT binding oligopeptides or TAT binding organic molecules.

To screen for antibodies, oligopeptides or other organic molecules which bind to an epitope on a TAT polypeptide bound by an antibody of interest, a routine cross-blocking assay such as that described in Antibodies, A Laboratory Manual, Cold Spring Harbor Laboratory, Ed Harlow and David Lane (1988), can be performed. This assay can be used to determine if a test antibody, oligopeptide or other organic molecule binds the same site or epitope as a known anti-TAT antibody. Alternatively, or additionally, epitope mapping can be performed by methods known in the art. For example, the antibody sequence can be mutagenized such as by alanine scanning, to identify contact residues. The mutant antibody is initially tested for binding with polyclonal antibody to ensure proper folding. In a different method, peptides corresponding to different regions of a TAT polypeptide can be used in competition assays with the test antibodies or with a test antibody and an antibody with a characterized or known epitope.

E. Antibody Dependent Enzyme Mediated Prodrug Therapy (ADEPT)

The antibodies of the present invention may also be used in ADEPT by conjugating the antibody to a prodrug-activating enzyme which converts a prodrug (e.g., a peptidyl chemotherapeutic agent, see WO81/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, Nature 328:457-458 (1987)). Antibody-abzyme conjugates can be prepared as described herein for delivery of the abzyme to a tumor cell population.

The enzymes of this invention can be covalently bound to the anti-TAT antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., Nature 312:604-608 (1984)).

F. Full-Length TAT Polypeptides

The present invention also provides newly identified and isolated nucleotide sequences encoding polypeptides referred to in the present application as TAT polypeptides. In particular, cDNAs (partial and full-length) encoding various TAT polypeptides have been identified and isolated, as disclosed in further detail in the Examples below.

As disclosed in the Examples below, various cDNA clones have been deposited with the ATCC. The actual nucleotide sequences of those clones can readily be determined by the skilled artisan by sequencing of the deposited clone using routine methods in the art. The predicted amino acid sequence can be determined from the nucleotide sequence using routine skill. For the TAT polypeptides and encoding nucleic acids described herein, in some cases, Applicants have identified what is believed to be the reading frame best identifiable with the sequence information available at the time.

G. Anti-TAT Antibody and TAT Polypeptide Variants

In addition to the anti-TAT antibodies and full-length native sequence TAT polypeptides described herein, it is contemplated that anti-TAT antibody and TAT polypeptide variants can be prepared. Anti-TAT antibody and TAT polypeptide variants can be prepared by introducing appropriate nucleotide changes into the encoding DNA, and/or by synthesis of the desired antibody or polypeptide. Those skilled in the art will appreciate that amino acid changes may alter post-translational processes of the anti-TAT antibody or TAT polypeptide, such as changing the number or position of glycosylation sites or altering the membrane anchoring characteristics.

Variations in the anti-TAT antibodies and TAT polypeptides described herein, can be made, for example, using any of the techniques and guidelines for conservative and nonconservative mutations set forth, for instance, in U.S. Pat. No. 5,364,934. Variations may be a substitution, deletion or insertion of one or more codons encoding the antibody or polypeptide that results in a change in the amino acid sequence as compared with the native sequence antibody or polypeptide. Optionally the variation is by substitution of at least one amino acid with any other amino acid in one or more of the domains of the anti-TAT antibody or TAT polypeptide. Guidance in determining which amino acid residue may be inserted, substituted or deleted without adversely affecting the desired activity may be found by comparing the sequence of the anti-TAT antibody or TAT polypeptide with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

Anti-TAT antibody and TAT polypeptide fragments are provided herein. Such fragments may be truncated at the N-terminus or C-terminus, or may lack internal residues, for example, when compared with a full length native antibody or protein. Certain fragments lack amino acid residues that are not essential for a desired biological activity of the anti-TAT antibody or TAT polypeptide.

Anti-TAT antibody and TAT polypeptide fragments may be prepared by any of a number of conventional techniques. Desired peptide fragments may be chemically synthesized. An alternative approach involves generating antibody or polypeptide fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired antibody or polypeptide fragment, by polymerase chain reaction (PCR). Oligonucleotides that define the desired termini of the DNA fragment are employed at the 5' and 3' primers in the PCR. Preferably, anti-TAT antibody and TAT polypeptide fragments share at least one biological and/or immunological activity with the native anti-TAT antibody or TAT polypeptide disclosed herein.

In particular embodiments, conservative substitutions of interest are shown in Table 6 under the heading of preferred substitutions. If such substitutions result in a change in biological activity, then more substantial changes, denominated exemplary substitutions in Table 1, or as further described below in reference to amino acid classes, are introduced and the products screened.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp; Lys; Arg | Gln |
| Asp (D) | Glu; Asn | Glu |
| Cys (C) | Ser, Ala | Ser |
| Gln (Q) | Asn; Glu | Asn |
| Glu (E) | Asp, Gln | Asp |
| Gly (G) | Pro; Ala | Ala |
| His (H) | Asn; Gln; Lys; Arg | Arg |
| Ile (I) | Leu; Val; Met; Ala; Phe; Leu | Norleucine |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Leu |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in function or immunological identity of the anti-TAT antibody or TAT polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: Norleucine, Met, Ala, Val, Leu, Ile;
(2) neutral hydrophilic: Cys, Ser, Thr; Asn; Gln
(3) acidic: Asp, Glu;
(4) basic: H is, Lys, Arg;
(5) residues that influence chain orientation: Gly, Pro; and
(6) aromatic: Trp, Tyr, Phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., Nucl. Acids Res., 13:4331 (1986); Zoller et al., Nucl. Acids Res., 10:6487 (1987)], cassette mutagenesis [Wells et al., Gene, 34:315 (1985)], restriction selection mutagenesis [Wells et al., Philos. Trans. R. Soc. London SerA, 317:415 (1986)] or other known techniques can be performed on the cloned DNA to produce the anti-TAT antibody or TAT polypeptide variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, Science, 244:1081-1085 (1989)]. Alanine is also typically preferred because it is the most common amino acid. Further, it is frequently found in both buried and exposed positions [Creighton, The Proteins, (W.H. Freeman & Co., N.Y.); Chothia, J. Mol. Biol., 150:1 (1976)]. If alanine substitution does not yield adequate amounts of variant, an isoteric amino acid can be used.

Any cysteine residue not involved in maintaining the proper conformation of the anti-TAT antibody or TAT polypeptide also may be substituted, generally with serine, to improve the oxidative stability of the molecule and prevent aberrant crosslinking Conversely, cysteine bond(s) may be added to the anti-TAT antibody or TAT polypeptide to improve its stability (particularly where the antibody is an antibody fragment such as an Fv fragment).

A particularly preferred type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and human TAT polypeptide. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the anti-TAT antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-TAT antibody.

H. Modifications of Anti-TAT Antibodies and TAT Polypeptides

Covalent modifications of anti-TAT antibodies and TAT polypeptides are included within the scope of this invention. One type of covalent modification includes reacting targeted amino acid residues of an anti-TAT antibody or TAT polypeptide with an organic derivatizing agent that is capable of reacting with selected side chains or the N- or C-terminal residues of the anti-TAT antibody or TAT polypeptide. Derivatization with bifunctional agents is useful, for instance, for crosslinking anti-TAT antibody or TAT polypeptide to a water-insoluble support matrix or surface for use in the method for purifying anti-TAT antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, Proteins: Structure and Molecular Properties, W.H. Freeman & Co., San Francisco, pp. 79-86 (1983)], acetylation of the N-terminal amine, and amidation of any C-terminal carboxyl group.

Another type of covalent modification of the anti-TAT antibody or TAT polypeptide included within the scope of this invention comprises altering the native glycosylation pattern of the antibody or polypeptide. "Altering the native glycosylation pattern" is intended for purposes herein to mean deleting one or more carbohydrate moieties found in native sequence anti-TAT antibody or TAT polypeptide (either by removing the underlying glycosylation site or by deleting the glycosylation by chemical and/or enzymatic means), and/or adding one or more glycosylation sites that are not present in the native sequence anti-TAT antibody or TAT polypeptide. In addition, the phrase includes qualitative changes in the glycosylation of the native proteins, involving a change in the nature and proportions of the various carbohydrate moieties present.

Glycosylation of antibodies and other polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the anti-TAT antibody or TAT polypeptide is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original anti-TAT antibody or TAT polypeptide (for O-linked glycosylation sites). The anti-TAT antibody or TAT polypeptide amino acid sequence may optionally be altered through changes at the DNA level, particularly by mutating the DNA encoding the anti-TAT antibody or TAT polypeptide at preselected bases such that codons are generated that will translate into the desired amino acids.

Another means of increasing the number of carbohydrate moieties on the anti-TAT antibody or TAT polypeptide is by chemical or enzymatic coupling of glycosides to the polypeptide. Such methods are described in the art, e.g., in WO 87/05330 published 11 Sep. 1987, and in Aplin and Wriston, CRC Crit. Rev. Biochem., pp. 259-306 (1981).

Removal of carbohydrate moieties present on the anti-TAT antibody or TAT polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties on polypeptides can be achieved by the use of a variety of endo- and exo-glycosidases as described by Thotakura et al., Meth. Enzymol., 138:350 (1987).

Another type of covalent modification of anti-TAT antibody or TAT polypeptide comprises linking the antibody or polypeptide to one of a variety of nonproteinaceous polymers, e.g., polyethylene glycol (PEG), polypropylene glycol, or polyoxyalkylenes, in the manner set forth in U.S. Pat. No. 4,640,835; 4,496,689; 4,301,144; 4,670,417; 4,791,192 or 4,179,337. The antibody or polypeptide also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nanoparticles and nanocapsules), or in macroemulsions. Such techniques are disclosed in Remington's Pharmaceutical Sciences, 16th edition, Oslo, A., Ed., (1980).

The anti-TAT antibody or TAT polypeptide of the present invention may also be modified in a way to form chimeric molecules comprising an anti-TAT antibody or TAT polypeptide fused to another, heterologous polypeptide or amino acid sequence.

In one embodiment, such a chimeric molecule comprises a fusion of the anti-TAT antibody or TAT polypeptide with a tag polypeptide which provides an epitope to which an anti-tag antibody can selectively bind. The epitope tag is generally placed at the amino- or carboxyl-terminus of the anti-TAT antibody or TAT polypeptide. The presence of such epitope-tagged forms of the anti-TAT antibody or TAT polypeptide can be detected using an antibody against the tag polypeptide. Also, provision of the epitope tag enables the anti-TAT antibody or TAT polypeptide to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., Mol. Cell. Biol., 8:2159-2165 (1988)]; the c-myc tag and the 8F9, 3C7, 6E10, G4, B7 and 9E10 antibodies thereto [Evan et al., Molecular and Cellular Biology, 5:3610-3616 (1985)]; and the Herpes Simplex virus glycoprotein D (gD) tag and its antibody [Paborsky et al., Protein Engineering, 3(6):547-553 (1990)]. Other tag polypeptides include the Flag-peptide [Hopp et al., BioTechnology, 6:1204-1210 (1988)]; the KT3 epitope peptide [Martin et al., Science, 255:192-194 (1992)]; an α-tubulin epitope peptide [Skinner et al., J. Biol. Chem., 266:15163-15166 (1991)]; and the T7 gene 10 protein peptide tag [Lutz-Freyermuth et al., Proc. Natl. Acad. Sci. USA, 87:6393-6397 (1990)].

In an alternative embodiment, the chimeric molecule may comprise a fusion of the anti-TAT antibody or TAT polypeptide with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of an anti-TAT antibody or TAT polypeptide in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

I. Preparation of Anti-TAT Antibodies and TAT Polypeptides

The description below relates primarily to production of anti-TAT antibodies and TAT polypeptides by culturing cells transformed or transfected with a vector containing anti-TAT antibody- and TAT polypeptide-encoding nucleic acid. It is, of course, contemplated that alternative methods, which are well known in the art, may be employed to prepare anti-TAT antibodies and TAT polypeptides. For instance, the appropriate amino acid sequence, or portions thereof, may be produced by direct peptide synthesis using solid-phase techniques [see, e.g., Stewart et al., Solid-Phase Peptide Synthesis, W.H. Freeman Co., San Francisco, Calif. (1969); Merrifield, J. Am. Chem. Soc., 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the anti-TAT antibody or TAT polypeptide may be chemically synthesized separately and combined using chemical or enzymatic methods to produce the desired anti-TAT antibody or TAT polypeptide.

1. Isolation of DNA Encoding Anti-TAT Antibody or TAT Polypeptide

DNA encoding anti-TAT antibody or TAT polypeptide may be obtained from a cDNA library prepared from tissue believed to possess the anti-TAT antibody or TAT polypeptide mRNA and to express it at a detectable level. Accordingly, human anti-TAT antibody or TAT polypeptide DNA can be conveniently obtained from a cDNA library prepared from human tissue. The anti-TAT antibody- or TAT polypeptide-encoding gene may also be obtained from a genomic library or by known synthetic procedures (e.g., automated nucleic acid synthesis).

Libraries can be screened with probes (such as oligonucleotides of at least about 20-80 bases) designed to identify the gene of interest or the protein encoded by it. Screening the cDNA or genomic library with the selected probe may be conducted using standard procedures, such as described in Sambrook et al., Molecular Cloning: A Laboratory Manual (New York: Cold Spring Harbor Laboratory Press, 1989). An alternative means to isolate the gene encoding anti-TAT antibody or TAT polypeptide is to use PCR methodology [Sambrook et al., supra; Dieffenbach et al., PCR Primer: A Laboratory Manual (Cold Spring Harbor Laboratory Press, 1995)].

Techniques for screening a cDNA library are well known in the art. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like 32P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for anti-TAT antibody or TAT polypeptide production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in Mammalian Cell Biotechnology: a Practical Approach, M. Butler, ed. (IRL Press, 1991) and Sambrook et al., supra.

Methods of eukaryotic cell transfection and prokaryotic cell transformation are known to the ordinarily skilled artisan, for example, CaCl2, CaPO4, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., Gene, 23:315 (1983) and WO 89/05859 published 29 Jun. 1989. For mammalian cells without such cell walls, the calcium phosphate precipitation method of Graham and van der Eb, Virology, 52:456-457 (1978) can be employed. General aspects of mammalian cell host system transfections have been described in U.S. Pat. No. 4,399,216. Transformations into yeast are typically carried out according to the method of Van Solingen et al., J. Bact., 130:946 (1977) and Hsiao et al., Proc. Natl. Acad. Sci. (USA), 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., Methods in Enzymology, 185:527-537 (1990) and Mansour et al., Nature, 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac)169 degP ompT kan$^r$; *E. coli* W3110 strain 37D6, which has the complete genotype tonA ptr3 phoA E15 (argF-lac)169 degP ompT rbs7 ilvG kan$^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

Full length antibody, antibody fragments, and antibody fusion proteins can be produced in bacteria, in particular when glycosylation and Fc effector function are not needed, such as when the therapeutic antibody is conjugated to a cytotoxic agent (e.g., a toxin) and the immunoconjugate by itself shows effectiveness in tumor cell destruction. Full length antibodies have greater half life in circulation. Production in *E. coli* is faster and more cost efficient. For expression of antibody fragments and polypeptides in bacteria, see, e.g., U.S. Pat. No. 5,648,237 (Carter et. al.), U.S. Pat. No. 5,789,199 (Joly et al.), and U.S. Pat. No. 5,840,523 (Simmons et al.) which describes translation initiation regio (TIR) and signal sequences for optimizing expression and secretion, these patents incorporated herein by reference. After expression, the antibody is isolated from the *E. coli* cell paste in a soluble fraction and can be purified through, e.g., a protein A or G column depending on the isotype. Final purification can be carried out similar to the process for purifying antibody expressed e.g., in CHO cells.

In addition to prokaryotes, eukaryotic microbes such as filamentous fungi or yeast are suitable cloning or expression hosts for anti-TAT antibody- or TAT polypeptide-encoding vectors. *Saccharomyces cerevisiae* is a commonly used lower eukaryotic host microorganism. Others include *Schizosaccharomyces pombe* (Beach and Nurse, Nature, 290: 140 [1981]; EP 139,383 published 2 May 1985); *Kluyveromyces* hosts (U.S. Pat. No. 4,943,529; Fleer et al., Bio/

Technology, 9:968-975 (1991)) such as, e.g., *K. lactis* (MW98-8C, CBS683, CBS4574; Louvencourt et al., J. Bacteriol., 154(2):737-742 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., Bio/Technology, 8:135 (1990)), *K. thermotolerans*, and *K. marxianus; yarrowia* (EP 402,226); *Pichia pastoris* (EP 183,070; Sreekrishna et al., J. Basic Microbiol., 28:265-278 [1988]); *Candida; Trichoderma reesia* (EP 244,234); *Neurospora crassa* (Case et al., Proc. Natl. Acad. Sci. USA, 76:5259-5263 [1979]); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., Biochem. Biophys. Res. Commun., 112:284-289 [1983]; Tilburn et al., Gene, 26:205-221 [1983]; Yelton et al., Proc. Natl. Acad. Sci. USA, 81: 1470-1474 [1984]) and *A. niger* (Kelly and Hynes, EMBO J., 4:475-479 [1985]). Methylotropic yeasts are suitable herein and include, but are not limited to, yeast capable of growth on methanol selected from the genera consisting of *Hansenula, Candida, Kloeckera, Pichia, Saccharomyces, Torulopsis*, and *Rhodotorula*. A list of specific species that are exemplary of this class of yeasts may be found in C. Anthony, The Biochemistry of Methylotrophs, 269 (1982).

Suitable host cells for the expression of glycosylated anti-TAT antibody or TAT polypeptide are derived from multicellular organisms. Examples of invertebrate cells include insect cells such as *Drosophila* S2 and *Spodoptera* Sf9, as well as plant cells, such as cell cultures of cotton, corn, potato, soybean, petunia, tomato, and tobacco. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/–DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for anti-TAT antibody or TAT polypeptide production and cultured in conventional nutrient media modified as appropriate for inducing promoters, selecting transformants, or amplifying the genes encoding the desired sequences.

3. Selection and Use of a Replicable Vector

The nucleic acid (e.g., cDNA or genomic DNA) encoding anti-TAT antibody or TAT polypeptide may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The TAT may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the anti-TAT antibody- or TAT polypeptide-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the anti-TAT antibody- or TAT polypeptide-encoding nucleic acid, such as DHFR or thymidine kinase. An appropriate host cell when wild-type DHFR is employed is the CHO cell line deficient in DHFR activity, prepared and propagated as described by Urlaub et al., Proc. Natl. Acad. Sci. USA, 77:4216 (1980). A suitable selection gene for use in yeast is the trp1 gene present in the yeast plasmid YRp7

[Stinchcomb et al., Nature, 282:39 (1979); Kingsman et al., Gene, 7:141 (1979); Tschemper et al., Gene, 10:157 (1980)]. The trp1 gene provides a selection marker for a mutant strain of yeast lacking the ability to grow in tryptophan, for example, ATCC No. 44076 or PEP4-1 [Jones, Genetics, 85:12 (1977)].

Expression and cloning vectors usually contain a promoter operably linked to the anti-TAT antibody- or TAT polypeptide-encoding nucleic acid sequence to direct mRNA synthesis. Promoters recognized by a variety of potential host cells are well known. Promoters suitable for use with prokaryotic hosts include the β-lactamase and lactose promoter systems [Chang et al., Nature, 275:615 (1978); Goeddel et al., Nature, 281:544 (1979)], alkaline phosphatase, a tryptophan (trp) promoter system [Goeddel, Nucleic Acids Res., 8:4057 (1980); EP 36,776], and hybrid promoters such as the tac promoter [deBoer et al., Proc. Natl. Acad. Sci. USA, 80:21-25 (1983)]. Promoters for use in bacterial systems also will contain a Shine-Dalgarno (S.D.) sequence operably linked to the DNA encoding anti-TAT antibody or TAT polypeptide.

Examples of suitable promoting sequences for use with yeast hosts include the promoters for 3-phosphoglycerate kinase [Hitzeman et al., J. Biol. Chem., 255:2073 (1980)] or other glycolytic enzymes [Hess et al., J. Adv. Enzyme Reg., 7:149 (1968); Holland, Biochemistry, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

Anti-TAT antibody or TAT polypeptide transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the anti-TAT antibody or TAT polypeptide by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the anti-TAT antibody or TAT polypeptide coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding anti-TAT antibody or TAT polypeptide.

Still other methods, vectors, and host cells suitable for adaptation to the synthesis of anti-TAT antibody or TAT polypeptide in recombinant vertebrate cell culture are described in Gething et al., Nature, 293:620-625 (1981); Mantei et al., Nature, 281:40-46 (1979); EP 117,060; and EP 117,058.

4. Culturing the Host Cells

The host cells used to produce the anti-TAT antibody or TAT polypeptide of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

5. Detecting Gene Amplification/Expression

Gene amplification and/or expression may be measured in a sample directly, for example, by conventional Southern blotting, Northern blotting to quantitate the transcription of mRNA [Thomas, Proc. Natl. Acad. Sci. USA, 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence TAT polypeptide or against a synthetic peptide based on the DNA sequences provided herein or against exogenous sequence fused to TAT DNA and encoding a specific antibody epitope.

6. Purification of Anti-TAT Antibody and TAT Polypeptide

Forms of anti-TAT antibody and TAT polypeptide may be recovered from culture medium or from host cell lysates. If membrane-bound, it can be released from the membrane using a suitable detergent solution (e.g. Triton-X 100) or by enzymatic cleavage. Cells employed in expression of anti-TAT antibody and TAT polypeptide can be disrupted by various physical or chemical means, such as freeze-thaw cycling, sonication, mechanical disruption, or cell lysing agents.

It may be desired to purify anti-TAT antibody and TAT polypeptide from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the anti-TAT antibody and TAT polypeptide. Various methods of protein purification may be employed and such methods are known in the art and described for example in Deutscher, Methods in Enzymology, 182 (1990); Scopes, Protein Purification: Principles and Practice, Springer-Verlag, New York (1982). The purification step(s) selected will depend, for example, on the nature of the production process used and the particular anti-TAT antibody or TAT polypeptide produced.

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., Bio/Technology 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2 or γ4 heavy chains (Lindmark et al., J. Immunol. Meth. 62:1-13 (1983)). Protein G is recommended for all mouse isotypes and for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

J. Pharmaceutical Formulations

Therapeutic formulations of the anti-TAT antibodies, TAT binding oligopeptides, TAT binding organic molecules and/or TAT polypeptides used in accordance with the present invention are prepared for storage by mixing the antibody, polypeptide, oligopeptide or organic molecule having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as acetate, Tris, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g., Zn-protein complexes); and/or non-ionic surfactants such as TWEEN®, PLURONICS® or polyethylene glycol (PEG). The antibody preferably comprises the antibody at a concentration of between 5-200 mg/ml, preferably between 10-100 mg/ml.

The formulations herein may also contain more than one active compound as necessary for the particular indication being treated, preferably those with complementary activities that do not adversely affect each other. For example, in addition to an anti-TAT antibody, TAT binding oligopeptide, or TAT binding organic molecule, it may be desirable to include in the one formulation, an additional antibody, e.g., a second anti-TAT antibody which binds a different epitope on the TAT polypeptide, or an antibody to some other target such as a growth factor that affects the growth of the particular cancer. Alternatively, or additionally, the composition may further comprise a chemotherapeutic agent, cytotoxic agent, cytokine, growth inhibitory agent, anti-hormonal agent, and/or cardioprotectant. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT® (injectable microspheres composed of lactic acid-glycolic acid copolymer and leuprolide acetate), and poly-D-β-3-hydroxybutyric acid.

The formulations to be used for in vivo administration must be sterile. This is readily accomplished by filtration through sterile filtration membranes.

K. Diagnosis and Treatment with Anti-TAT Antibodies, TAT Binding Oligopeptides and TAT Binding Organic Molecules To determine TAT expression in the cancer, various diagnostic assays are available. In one embodiment, TAT polypeptide overexpression may be analyzed by immunohistochemistry (IHC). Parrafin embedded tissue sections from a tumor biopsy may be subjected to the IHC assay and accorded a TAT protein staining intensity criteria as follows:

Score 0—no staining is observed or membrane staining is observed in less than 10% of tumor cells.

Score 1+—a faint/barely perceptible membrane staining is detected in more than 10% of the tumor cells. The cells are only stained in part of their membrane.

Score 2+—a weak to moderate complete membrane staining is observed in more than 10% of the tumor cells.

Score 3+—a moderate to strong complete membrane staining is observed in more than 10% of the tumor cells.

Those tumors with 0 or 1+ scores for TAT polypeptide expression may be characterized as not overexpressing TAT, whereas those tumors with 2+ or 3+ scores may be characterized as overexpressing TAT.

Alternatively, or additionally, FISH assays such as the INFORM® (sold by Ventana, Ariz.) or PATHVISION® (Vysis, Ill.) may be carried out on formalin-fixed, paraffin-embedded tumor tissue to determine the extent (if any) of TAT overexpression in the tumor.

TAT overexpression or amplification may be evaluated using an in vivo diagnostic assay, e.g., by administering a molecule (such as an antibody, oligopeptide or organic molecule) which binds the molecule to be detected and is tagged with a detectable label (e.g., a radioactive isotope or a fluorescent label) and externally scanning the patient for localization of the label.

As described above, the anti-TAT antibodies, oligopeptides and organic molecules of the invention have various non-therapeutic applications. The anti-TAT antibodies, oligopeptides and organic molecules of the present invention can be useful for diagnosis and staging of TAT polypeptide-expressing cancers (e.g., in radioimaging). The antibodies, oligopeptides and organic molecules are also useful for purification or immunoprecipitation of TAT polypeptide from cells, for detection and quantitation of TAT polypeptide in vitro, e.g., in an ELISA or a Western blot, to kill and eliminate TAT-expressing cells from a population of mixed cells as a step in the purification of other cells.

Currently, depending on the stage of the cancer, cancer treatment involves one or a combination of the following therapies: surgery to remove the cancerous tissue, radiation therapy, and chemotherapy. Anti-TAT antibody, oligopeptide or organic molecule therapy may be especially desirable in elderly patients who do not tolerate the toxicity and side effects of chemotherapy well and in metastatic disease where radiation therapy has limited usefulness. The tumor targeting anti-TAT antibodies, oligopeptides and organic molecules of the invention are useful to alleviate TAT-expressing cancers upon initial diagnosis of the disease or during relapse. For therapeutic applications, the anti-TAT antibody, oligopeptide or organic molecule can be used alone, or in combination therapy with, e.g., hormones, antiangiogens, or radiolabelled compounds, or with surgery, cryotherapy, and/or radiotherapy. Anti-TAT antibody, oligopeptide or organic molecule treatment can be administered in conjunction with other forms of conventional therapy, either consecutively with, pre- or post-conventional therapy. Chemotherapeutic drugs such as TAXOTERE® (docetaxel), TAXOL® (palictaxel), estramustine and mitoxantrone are used in treating cancer, in particular, in good risk patients. In the present method of the invention for treating or alleviating cancer, the cancer patient can be administered anti-TAT antibody, oligopeptide or organic molecule in conjuction with treatment with the one or more of the preceding chemotherapeutic agents. In particular, combination therapy with palictaxel and modified derivatives (see, e.g., EP0600517) is contemplated. The anti-TAT antibody, oligopeptide or organic molecule will be administered with a therapeutically effective dose of the chemotherapeutic agent. In another embodiment, the anti-TAT antibody, oligopeptide or organic molecule is administered in conjunction with chemotherapy to enhance the activity and efficacy of the chemotherapeutic agent, e.g., paclitaxel. The Physicians' Desk Reference (PDR) discloses dosages of these agents that have been used in treatment of various cancers. The dosing regimen and dosages of these aforementioned chemotherapeutic drugs that are therapeutically effective will depend on the particular cancer being treated, the extent of the disease and other factors familiar to the physician of skill in the art and can be determined by the physician.

In one particular embodiment, a conjugate comprising an anti-TAT antibody, oligopeptide or organic molecule conjugated with a cytotoxic agent is administered to the patient. Preferably, the immunoconjugate bound to the TAT protein is internalized by the cell, resulting in increased therapeutic efficacy of the immunoconjugate in killing the cancer cell to which it binds. In a preferred embodiment, the cytotoxic agent targets or interferes with the nucleic acid in the cancer cell. Examples of such cytotoxic agents are described above and include maytansinoids, calicheamicins, ribonucleases and DNA endonucleases.

The anti-TAT antibodies, oligopeptides, organic molecules or toxin conjugates thereof are administered to a human patient, in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes.

Intravenous or subcutaneous administration of the antibody, oligopeptide or organic molecule is preferred.

Other therapeutic regimens may be combined with the administration of the anti-TAT antibody, oligopeptide or organic molecule. The combined administration includes co-administration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect.

It may also be desirable to combine administration of the anti-TAT antibody or antibodies, oligopeptides or organic molecules, with administration of an antibody directed against another tumor antigen associated with the particular cancer.

In another embodiment, the therapeutic treatment methods of the present invention involves the combined administration of an anti-TAT antibody (or antibodies), oligopeptides or organic molecules and one or more chemotherapeutic agents or growth inhibitory agents, including co-administration of cocktails of different chemotherapeutic agents. Chemotherapeutic agents include estramustine phosphate, prednimustine, cisplatin, 5-fluorouracil, melphalan, cyclophosphamide, hydroxyurea and hydroxyureataxanes (such as paclitaxel and doxetaxel) and/or anthracycline antibiotics. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992).

The antibody, oligopeptide or organic molecule may be combined with an anti-hormonal compound; e.g., an anti-estrogen compound such as tamoxifen; an anti-progesterone such as onapristone (see, EP 616 812); or an anti-androgen such as flutamide, in dosages known for such molecules. Where the cancer to be treated is androgen independent cancer, the patient may previously have been subjected to anti-androgen therapy and, after the cancer becomes androgen independent, the anti-TAT antibody, oligopeptide or organic molecule (and optionally other agents as described herein) may be administered to the patient.

Sometimes, it may be beneficial to also co-administer a cardioprotectant (to prevent or reduce myocardial dysfunction associated with the therapy) or one or more cytokines to the patient. In addition to the above therapeutic regimes, the patient may be subjected to surgical removal of cancer cells and/or radiation therapy, before, simultaneously with, or post antibody, oligopeptide or organic molecule therapy. Suitable dosages for any of the above co-administered agents are those presently used and may be lowered due to the combined action (synergy) of the agent and anti-TAT antibody, oligopeptide or organic molecule.

For the prevention or treatment of disease, the dosage and mode of administration will be chosen by the physician according to known criteria. The appropriate dosage of antibody, oligopeptide or organic molecule will depend on the type of disease to be treated, as defined above, the severity and course of the disease, whether the antibody, oligopeptide or organic molecule is administered for preventive or therapeutic purposes, previous therapy, the patient's clinical history and response to the antibody, oligopeptide or organic molecule, and the discretion of the attending physician. The antibody, oligopeptide or organic molecule is suitably administered to the patient at one time or over a series of treatments. Preferably, the antibody, oligopeptide or organic molecule is administered by intravenous infusion or by subcutaneous injections. Depending on the type and severity of the disease, about 1 μg/kg to about 50 mg/kg body weight (e.g., about 0.1-15 mg/kg/dose) of antibody can be an initial candidate dosage for administration to the patient, whether, for example, by one or more separate administrations, or by continuous infusion. A dosing regimen can comprise administering an initial loading dose of about 4 mg/kg, followed by a weekly maintenance dose of about 2 mg/kg of the anti-TAT antibody. However, other dosage regimens may be useful. A typical daily dosage might range from about 1 μg/kg to 100 mg/kg or more, depending on the factors mentioned above. For repeated administrations over several days or longer, depending on the condition, the treatment is sustained until a desired suppression of disease symptoms occurs. The progress of this therapy can be readily monitored by conventional methods and assays and based on criteria known to the physician or other persons of skill in the art.

Aside from administration of the antibody protein to the patient, the present application contemplates administration of the antibody by gene therapy. Such administration of nucleic acid encoding the antibody is encompassed by the expression "administering a therapeutically effective amount of an antibody". See, for example, WO96/07321 published Mar. 14, 1996 concerning the use of gene therapy to generate intracellular antibodies.

There are two major approaches to getting the nucleic acid (optionally contained in a vector) into the patient's cells; in vivo and ex vivo. For in vivo delivery the nucleic acid is injected directly into the patient, usually at the site where the antibody is required. For ex vivo treatment, the patient's cells are removed, the nucleic acid is introduced into these isolated cells and the modified cells are administered to the patient either directly or, for example, encapsulated within porous membranes which are implanted into the patient (see, e.g., U.S. Pat. Nos. 4,892,538 and 5,283,187). There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retroviral vector.

The currently preferred in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). For review of the currently known gene marking and gene therapy protocols see Anderson et al., Science 256:808-813 (1992). See also WO 93/25673 and the references cited therein.

The anti-TAT antibodies of the invention can be in the different forms encompassed by the definition of "antibody" herein. Thus, the antibodies include full length or intact antibody, antibody fragments, native sequence antibody or amino acid variants, humanized, chimeric or fusion antibodies, immunoconjugates, and functional fragments thereof. In fusion antibodies an antibody sequence is fused to a heterologous polypeptide sequence. The antibodies can be modified in the Fc region to provide desired effector functions. As discussed in more detail in the sections herein, with the appropriate Fc regions, the naked antibody bound on the cell surface can induce cytotoxicity, e.g., via antibody-dependent cellular cytotoxicity (ADCC) or by recruiting complement in complement dependent cytotoxicity, or some other mechanism. Alternatively, where it is desirable to eliminate or reduce effector function, so as to minimize side effects or therapeutic complications, certain other Fc regions may be used.

In one embodiment, the antibody competes for binding or bind substantially to, the same epitope as the antibodies of the invention. Antibodies having the biological characteristics of the present anti-TAT antibodies of the invention are also contemplated, specifically including the in vivo tumor targeting and any cell proliferation inhibition or cytotoxic characteristics.

Methods of producing the above antibodies are described in detail herein.

The present anti-TAT antibodies, oligopeptides and organic molecules are useful for treating a TAT-expressing cancer or alleviating one or more symptoms of the cancer in a mammal. Such a cancer includes prostate cancer, cancer of the urinary tract, lung cancer, breast cancer, colon cancer and ovarian cancer, more specifically, prostate adenocarcinoma, renal cell carcinomas, colorectal adenocarcinomas, lung adenocarcinomas, lung squamous cell carcinomas, and pleural mesothelioma. The cancers encompass metastatic cancers of any of the preceding. The antibody, oligopeptide or organic molecule is able to bind to at least a portion of the cancer cells that express TAT polypeptide in the mammal. In a preferred embodiment, the antibody, oligopeptide or organic molecule is effective to destroy or kill TAT-expressing tumor cells or inhibit the growth of such tumor cells, in vitro or in vivo, upon binding to TAT polypeptide on the cell. Such an antibody includes a naked anti-TAT antibody (not conjugated to any agent). Naked antibodies that have cytotoxic or cell growth inhibition properties can be further harnessed with a cytotoxic agent to render them even more potent in tumor cell destruction. Cytotoxic properties can be conferred to an anti-TAT antibody by, e.g., conjugating the antibody with a cytotoxic agent, to form an immunoconjugate as described herein. The cytotoxic agent or a growth inhibitory agent is preferably a small molecule. Toxins such as calicheamicin or a maytansinoid and analogs or derivatives thereof, are preferable.

The invention provides a composition comprising an anti-TAT antibody, oligopeptide or organic molecule of the invention, and a carrier. For the purposes of treating cancer, compositions can be administered to the patient in need of such treatment, wherein the composition can comprise one or more anti-TAT antibodies present as an immunoconjugate or as the naked antibody. In a further embodiment, the compositions can comprise these antibodies, oligopeptides or organic molecules in combination with other therapeutic agents such as cytotoxic or growth inhibitory agents, including chemotherapeutic agents. The invention also provides formulations comprising an anti-TAT antibody, oligopeptide or organic molecule of the invention, and a carrier. In one embodiment, the formulation is a therapeutic formulation comprising a pharmaceutically acceptable carrier.

Another aspect of the invention is isolated nucleic acids encoding the anti-TAT antibodies. Nucleic acids encoding both the H and L chains and especially the hypervariable region residues, chains which encode the native sequence antibody as well as variants, modifications and humanized versions of the antibody, are encompassed.

The invention also provides methods useful for treating a TAT polypeptide-expressing cancer or alleviating one or more symptoms of the cancer in a mammal, comprising administering a therapeutically effective amount of an anti-TAT antibody, oligopeptide or organic molecule to the mammal. The antibody, oligopeptide or organic molecule therapeutic compositions can be administered short term (acute) or chronic, or intermittent as directed by physician. Also provided are methods of inhibiting the growth of, and killing a TAT polypeptide-expressing cell.

The invention also provides kits and articles of manufacture comprising at least one anti-TAT antibody, oligopeptide or organic molecule. Kits containing anti-TAT antibodies, oligopeptides or organic molecules find use, e.g., for TAT cell killing assays, for purification or immunoprecipitation of TAT polypeptide from cells. For example, for isolation and purification of TAT, the kit can contain an anti-TAT antibody, oligopeptide or organic molecule coupled to beads (e.g., sepharose beads). Kits can be provided which contain the antibodies, oligopeptides or organic molecules for detection and quantitation of TAT in vitro, e.g., in an ELISA or a Western blot. Such antibody, oligopeptide or organic molecule useful for detection may be provided with a label such as a fluorescent or radiolabel.

L. Articles of Manufacture and Kits

Another embodiment of the invention is an article of manufacture containing materials useful for the treatment of anti-TAT expressing cancer. The article of manufacture comprises a container and a label or package insert on or associated with the container. Suitable containers include, for example, bottles, vials, syringes, etc. The containers may be formed from a variety of materials such as glass or plastic. The container holds a composition which is effective for treating the cancer condition and may have a sterile access port (for example the container may be an intravenous solution bag or a vial having a stopper pierceable by a hypodermic injection needle). At least one active agent in the composition is an anti-TAT antibody, oligopeptide or organic molecule of the invention. The label or package insert indicates that the composition is used for treating cancer. The label or package insert will further comprise instructions for administering the antibody, oligopeptide or organic molecule composition to the cancer patient. Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., for TAT-expressing cell killing assays, for purification or immunoprecipitation of TAT polypeptide from cells. For isolation and purification of TAT polypeptide, the kit can contain an anti-TAT antibody, oligopeptide or organic molecule coupled to beads (e.g., sepharose beads). Kits can be provided which contain the antibodies, oligopeptides or organic molecules for detection and quantitation of TAT polypeptide in vitro, e.g., in an ELISA or a Western blot. As with the article of manufacture, the kit comprises a container and a label or package insert on or associated with the container. The container holds a composition comprising at least one anti-TAT antibody, oligopeptide or organic molecule of the invention. Additional containers may be included that contain, e.g., diluents and buffers, control antibodies. The label or package insert may provide a description of the composition as well as instructions for the intended in vitro or diagnostic use.

M. Uses for TAT Polypeptides and TAT-Polypeptide Encoding Nucleic Acids

Nucleotide sequences (or their complement) encoding TAT polypeptides have various applications in the art of molecular biology, including uses as hybridization probes, in chromosome and gene mapping and in the generation of anti-sense RNA and DNA probes. TAT-encoding nucleic acid will also be useful for the preparation of TAT polypeptides by the recombinant techniques described herein, wherein those TAT polypeptides may find use, for example, in the preparation of anti-TAT antibodies as described herein.

The full-length native sequence TAT gene, or portions thereof, may be used as hybridization probes for a cDNA library to isolate the full-length TAT cDNA or to isolate still other cDNAs (for instance, those encoding naturally-occurring variants of TAT or TAT from other species) which have a desired sequence identity to the native TAT sequence disclosed herein. Optionally, the length of the probes will be about 20 to about 50 bases. The hybridization probes may be derived from at least partially novel regions of the full length native nucleotide sequence wherein those regions may be determined without undue experimentation or from genomic sequences including promoters, enhancer elements and introns of native sequence TAT. By way of example, a screening method will comprise isolating the coding region of the TAT gene using the known DNA sequence to synthesize a selected probe of about 40 bases. Hybridization probes may be labeled by a variety of labels, including radionucleotides such as 32P or 35S, or enzymatic labels such as alkaline phosphatase coupled to the probe via avidin/biotin coupling systems. Labeled probes having a sequence complementary to that of the TAT gene of the present invention can be used to screen libraries of human cDNA, genomic DNA or mRNA to determine which members of such libraries the probe hybridizes to. Hybridization techniques are described in further detail in the Examples below. Any EST sequences disclosed in the present application may similarly be employed as probes, using the methods disclosed herein.

Other useful fragments of the TAT-encoding nucleic acids include antisense or sense oligonucleotides comprising a singe-stranded nucleic acid sequence (either RNA or DNA) capable of binding to target TAT mRNA (sense) or TAT DNA (antisense) sequences. Antisense or sense oligonucleotides, according to the present invention, comprise a fragment of the coding region of TAT DNA. Such a fragment generally comprises at least about 14 nucleotides, preferably from about 14 to 30 nucleotides. The ability to derive an antisense or a sense oligonucleotide, based upon a cDNA sequence encoding a given protein is described in, for example, Stein and Cohen (Cancer Res. 48:2659, 1988) and van der Krol et al. (BioTechniques 6:958, 1988).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. Such methods are encompassed by the present invention. The antisense oligonucleotides thus may be used to block expression of TAT proteins, wherein those TAT proteins may play a role in the induction of cancer in mammals. Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Preferred intragenic sites for antisense binding include the region incorporating the translation initiation/start codon (5'-AUG/5'-ATG) or termination/stop codon (5'-UAA, 5'-UAG and 5-UGA/5'-TAA, 5'-TAG and 5'-TGA) of the open reading frame (ORF) of the gene. These regions refer to a portion of the mRNA or gene that encompasses from about 25 to about 50 contiguous nucleotides in either direction (i.e., 5' or 3') from a translation initiation or termination codon. Other preferred regions for antisense binding include: introns; exons; intron-exon junctions; the open reading frame (ORF) or "coding region," which is the region between the translation initiation codon and the translation termination codon; the 5' cap of an mRNA which comprises an N7-methylated guanosine residue joined to the 5'-most residue of the mRNA via a 5'-5' triphosphate linkage and includes 5' cap structure itself as well as the first 50 nucleotides adjacent to the cap; the 5' untranslated region (5'UTR), the portion of an mRNA in the 5' direction from the translation initiation codon, and thus including nucleotides between the 5' cap site and the translation initiation codon of an mRNA or corresponding nucleotides on the gene; and the 3' untranslated region (3'UTR), the portion of an mRNA in the 3' direction from the translation termination codon, and thus including nucleotides between the translation termination codon and 3' end of an mRNA or corresponding nucleotides on the gene.

Specific examples of preferred antisense compounds useful for inhibiting expression of TAT proteins include oligonucleotides containing modified backbones or non-natural internucleoside linkages. Oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides. Preferred modified oligonucleotide backbones include, for example, phosphorothioates, chiral phosphorothioates, phosphorodithioates, phosphotriesters, aminoalkylphosphotri-esters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included. Representative United States patents that teach the preparation of phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH.sub.2 component parts. Representative United States patents that teach the preparation of such oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

In other preferred antisense oligonucleotides, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

Preferred antisense oligonucleotides incorporate phosphorothioate backbones and/or heteroatom backbones, and in particular —CH2-NH—O—CH2-, —CH2-N(CH3)-O—CH2-[known as a methylene (methylimino) or MMI backbone], —CH2-O—N(CH3)-CH2-, —CH2-N(CH3)-N(CH3)-CH2- and —O—N(CH3)-CH2-CH2-[wherein the native phosphodiester backbone is represented as —O—P—O—CH2-] described in the above referenced U.S. Pat. No. 5,489,677, and the amide backbones of the above referenced U.S. Pat. No. 5,602,240. Also preferred are antisense oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-alkyl, S-alkyl, or N-alkyl; O-alkenyl, S-alkeynyl, or N-alkenyl; O-alkynyl, S-alkynyl or N-alkynyl; or O-alkyl-O-alkyl, wherein the alkyl, alkenyl and alkynyl may be substituted or unsubstituted C1 to C10 alkyl or C2 to C10 alkenyl and alkynyl. Particularly preferred are O[(CH2)nO]mCH3, O(CH2)nOCH3, O(CH2)nNH2, O(CH2)nCH3, O(CH2)nONH2, and O(CH2)nON[(CH2)nCH3)]2, where n and m are from 1 to about 10. Other preferred antisense oligonucleotides comprise one of the following at the 2' position: C1 to C10 lower alkyl, substituted lower alkyl, alkenyl, alkynyl, alkaryl, aralkyl, O-alkaryl or O-aralkyl, SH, SCH3, OCN, Cl, Br, CN, CF3, OCF3, SOCH3, SO2 CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy(2'-O—CH2CH$_2$OCH3, also known as 2'-O-(2-methoxyethyl) or 2'-MOE) (Martin et al., Helv. Chim. Acta, 1995, 78, 486-504) i.e., an alkoxyalkoxy group. A further preferred modification includes 2'-dimethylaminooxyethoxy, i.e., a O(CH2)2-ON(CH3)2 group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—CH2-O—CH2-N(CH2).

A further preferred modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne (—CH2-)n group bridging the 2' oxygen atom and the 4' carbon atom wherein n is 1 or 2. LNAs and preparation thereof are described in WO 98/39352 and WO 99/14226.

Other preferred modifications include 2'-methoxy(2'-O—CH3), 2'-aminopropoxy(2'-OCH2CH2CH2 NH2), 2'-allyl (2'-CH2-CH=CH2), 2'-O-allyl (2'-O—CH2-CH=CH2) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C=C—CH3 or —CH2-C=CH) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine(1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine(2H-pyrimido[4,5-b]indol-2-one), pyridoindole cytidine (H-pyrido[3',':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, and those disclosed by Englisch et al., Angewandte Chemie, International Edition, 1991, 30, 613. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2.degrees C. (Sanghvi et al, Antisense Research and Applications, CRC Press, Boca Raton, 1993, pp. 276-278) and are preferred base substitutions, even more particularly when combined with 2'-O-methoxyethyl sugar modifications. Representative United States patents that teach the preparation of modified nucleobases include, but are not limited to: U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; 5,681,941 and 5,750,692, each of which is herein incorporated by reference.

Another modification of antisense oligonucleotides chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, cation lipids, phospholipids, cationic phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-5-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) and U.S. Pat. Nos. 4,828, 979; 4,948,882; 5,218,105; 5,525,465; 5,541,313; 5,545, 730; 5,552,538; 5,578,717; 5,580,731; 5,580,731; 5,591, 584; 5,109,124; 5,118,802; 5,138,045; 5,414,077; 5,486, 603; 5,512,439; 5,578,718; 5,608,046; 4,587,044; 4,605, 735; 4,667,025; 4,762,779; 4,789,737; 4,824,941; 4,835, 263; 4,876,335; 4,904,582; 4,958,013; 5,082,830; 5,112, 963; 5,214,136; 5,082,830; 5,112,963; 5,214,136; 5,245, 022; 5,254,469; 5,258,506; 5,262,536; 5,272,250; 5,292, 873; 5,317,098; 5,371,241; 5,391,723; 5,416,203, 5,451, 463; 5,510,475; 5,512,667; 5,514,785; 5,565,552; 5,567, 810; 5,574,142; 5,585,481; 5,587,371; 5,595,726; 5,597, 696; 5,599,923; 5,599,928 and 5,688,941, each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Chimeric antisense compounds of the invention may be formed as composite structures of two or more oligonucleotides, modified oligonucleotides, oligonucleosides and/or oligonucleotide mimetics as described above. Preferred chimeric antisense oligonucleotides incorporate at least one 2' modified sugar (preferably 2'-O—(CH2)2-O—CH3) at the 3' terminal to confer nuclease resistance and a region with at least 4 contiguous 2'-H sugars to confer RNase H activity. Such compounds have also been referred to in the art as hybrids or gapmers. Preferred gapmers have a region of 2' modified sugars (preferably 2'-O—(CH2)$_2$—O—CH3) at the 3'-terminal and at the 5' terminal separated by at least one region having at least 4 contiguous 2'-H sugars and preferably incorporate phosphorothioate backbone linkages. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

Other examples of sense or antisense oligonucleotides include those oligonucleotides which are covalently linked to organic moieties, such as those described in WO 90/10048, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, CaPO4-mediated DNA transfection, electroporation, or by using gene transfer vectors such as Epstein-Barr virus. In a preferred procedure, an antisense or sense oligonucleotide is inserted into a suitable retroviral vector. A cell containing the target nucleic acid sequence is contacted with the recombinant retroviral vector, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see WO 90/13641).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Antisense or sense RNA or DNA molecules are generally at least about 5 nucleotides in length, alternatively at least about 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides in length, wherein in this context the term "about" means the referenced nucleotide sequence length plus or minus 10% of that referenced length.

The probes may also be employed in PCR techniques to generate a pool of sequences for identification of closely related TAT coding sequences.

Nucleotide sequences encoding a TAT can also be used to construct hybridization probes for mapping the gene which encodes that TAT and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

When the coding sequences for TAT encode a protein which binds to another protein (example, where the TAT is a receptor), the TAT can be used in assays to identify the other proteins or molecules involved in the binding interaction. By such methods, inhibitors of the receptor/ligand binding interaction can be identified. Proteins involved in such binding interactions can also be used to screen for peptide or small molecule inhibitors or agonists of the binding interaction. Also, the receptor TAT can be used to isolate correlative ligand(s). Screening assays can be designed to find lead compounds that mimic the biological activity of a native TAT or a receptor for TAT. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode TAT or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding TAT can be used to clone genomic DNA encoding TAT in accordance with established techniques and the genomic sequences used to generate transgenic animals that contain cells which express DNA encoding TAT. Methods for generating transgenic animals, particularly animals such as mice or rats, have become conventional in the art and are described, for example, in U.S. Pat. Nos. 4,736,866 and 4,870,009. Typically, particular cells would be targeted for TAT transgene incorporation with tissue-specific enhancers. Transgenic animals that include a copy of a transgene encoding TAT introduced into the germ line of the animal at an embryonic stage can be used to examine the effect of increased expression of DNA encoding TAT. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of TAT can be used to construct a TAT "knock out" animal which has a defective or altered gene encoding TAT as a result of homologous recombination between the endogenous gene encoding TAT and altered genomic DNA encoding TAT introduced into an embryonic stem cell of the animal. For example, cDNA encoding TAT can be used to clone genomic DNA encoding TAT in accordance with established techniques. A portion of the genomic DNA encoding TAT can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, Cell, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., Cell, 69:915 (1992)]. The selected cells are then injected into a blastocyst of an animal (e.g., a mouse or rat) to form aggregation chimeras [see e.g., Bradley, in Teratocarcinomas and Embryonic Stem Cells: A Practical Approach, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the TAT polypeptide.

Nucleic acid encoding the TAT polypeptides may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., Proc. Natl. Acad. Sci. USA 83:4143-4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., Trends in Biotechnology 11, 205-210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., J. Biol. Chem. 262, 4429-4432 (1987); and Wagner et al., Proc. Natl. Acad. Sci. USA 87, 3410-3414 (1990). For review of gene marking and gene therapy protocols see Anderson et al., Science 256, 808-813 (1992).

The nucleic acid molecules encoding the TAT polypeptides or fragments thereof described herein are useful for chromosome identification. In this regard, there exists an ongoing need to identify new chromosome markers, since relatively few chromosome marking reagents, based upon actual sequence data are presently available. Each TAT nucleic acid molecule of the present invention can be used as a chromosome marker.

The TAT polypeptides and nucleic acid molecules of the present invention may also be used diagnostically for tissue typing, wherein the TAT polypeptides of the present invention may be differentially expressed in one tissue as compared to another, preferably in a diseased tissue as compared to a normal tissue of the same tissue type. TAT nucleic acid molecules will find use for generating probes for PCR, Northern analysis, Southern analysis and Western analysis.

This invention encompasses methods of screening compounds to identify those that mimic the TAT polypeptide (agonists) or prevent the effect of the TAT polypeptide (antagonists). Screening assays for antagonist drug candidates are designed to identify compounds that bind or complex with the TAT polypeptides encoded by the genes identified herein, or otherwise interfere with the interaction of the encoded polypeptides with other cellular proteins, including e.g., inhibiting the expression of TAT polypeptide from cells. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

All assays for antagonists are common in that they call for contacting the drug candidate with a TAT polypeptide encoded by a nucleic acid identified herein under conditions and for a time sufficient to allow these two components to interact.

In binding assays, the interaction is binding and the complex formed can be isolated or detected in the reaction mixture. In a particular embodiment, the TAT polypeptide encoded by the gene identified herein or the drug candidate is immobilized on a solid phase, e.g., on a microtiter plate, by covalent or non-covalent attachments. Non-covalent attachment generally is accomplished by coating the solid surface with a solution of the TAT polypeptide and drying. Alternatively, an immobilized antibody, e.g., a monoclonal antibody, specific for the TAT polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular TAT polypeptide encoded by a gene identified herein, its interaction with that polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, Nature (London), 340:245-246 (1989); Chien et al., Proc. Natl. Acad. Sci. USA, 88:9578-9582 (1991)) as disclosed by Chevray and Nathans, Proc. Natl. Acad. Sci. USA, 89: 5789-5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a gene encoding a TAT polypeptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

To assay for antagonists, the TAT polypeptide may be added to a cell along with the compound to be screened for a particular activity and the ability of the compound to inhibit the activity of interest in the presence of the TAT polypeptide indicates that the compound is an antagonist to the TAT polypeptide. Alternatively, antagonists may be detected by combining the TAT polypeptide and a potential antagonist with membrane-bound TAT polypeptide receptors or recombinant receptors under appropriate conditions for a competitive inhibition assay. The TAT polypeptide can be labeled, such as by radioactivity, such that the number of TAT polypeptide molecules bound to the receptor can be used to determine the effectiveness of the potential antagonist. The gene encoding the receptor can be identified by numerous methods known to those of skill in the art, for example, ligand panning and FACS sorting. Coligan et al., Current Protocols in Immun., 1(2): Chapter 5 (1991). Preferably, expression cloning is employed wherein polyadenylated RNA is prepared from a cell responsive to the TAT polypeptide and a cDNA library created from this RNA is divided into pools and used to transfect COS cells or other cells that are not responsive to the TAT polypeptide. Transfected cells that are grown on glass slides are exposed to labeled TAT polypeptide. The TAT polypeptide can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an interactive sub-pooling and re-screening process, eventually yielding a single clone that encodes the putative receptor.

As an alternative approach for receptor identification, labeled TAT polypeptide can be photoaffinity-linked with cell membrane or extract preparations that express the receptor molecule. Cross-linked material is resolved by PAGE and exposed to X-ray film. The labeled complex containing the receptor can be excised, resolved into peptide fragments, and subjected to protein micro-sequencing. The amino acid sequence obtained from micro-sequencing would be used to design a set of degenerate oligonucleotide probes to screen a cDNA library to identify the gene encoding the putative receptor.

In another assay for antagonists, mammalian cells or a membrane preparation expressing the receptor would be incubated with labeled TAT polypeptide in the presence of the candidate compound. The ability of the compound to enhance or block this interaction could then be measured.

More specific examples of potential antagonists include an oligonucleotide that binds to the fusions of immunoglobulin with TAT polypeptide, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of the TAT polypeptide that recognizes the receptor but imparts no effect, thereby competitively inhibiting the action of the TAT polypeptide.

Another potential TAT polypeptide antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature TAT polypeptides herein, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al., Science, 241: 456 (1988); Dervan et al., Science, 251: 1360 (1991)), thereby preventing transcription and the production of the TAT polypeptide. The antisense RNA oligonucleotide hybridizes to the mRNA in vivo and blocks translation of the mRNA molecule into the TAT polypeptide (antisense—Okano, Neurochem., 56:560 (1991); Oligodeoxynucleotides as Antisense Inhibitors of Gene Expression (CRC Press: Boca Raton, Fla., 1988). The oligonucleotides described above can also be delivered to cells such that the antisense RNA or DNA may be expressed in vivo to inhibit production of the TAT polypeptide. When antisense DNA is used, oligodeoxyribonucleotides derived from the translation-initiation site, e.g., between about −10 and +10 positions of the target gene nucleotide sequence, are preferred.

Potential antagonists include small molecules that bind to the active site, the receptor binding site, or growth factor or other relevant binding site of the TAT polypeptide, thereby blocking the normal biological activity of the TAT polypeptide. Examples of small molecules include, but are not limited to, small peptides or peptide-like molecules, preferably soluble peptides, and synthetic non-peptidyl organic or inorganic compounds.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, Current Biology, 4:469-471 (1994), and PCT publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra.

These small molecules can be identified by any one or more of the screening assays discussed hereinabove and/or by any other screening techniques well known for those skilled in the art.

Isolated TAT polypeptide-encoding nucleic acid can be used herein for recombinantly producing TAT polypeptide using techniques well known in the art and as described herein. In turn, the produced TAT polypeptides can be employed for generating anti-TAT antibodies using techniques well known in the art and as described herein.

Antibodies specifically binding a TAT polypeptide identified herein, as well as other molecules identified by the screening assays disclosed hereinbefore, can be administered for the treatment of various disorders, including cancer, in the form of pharmaceutical compositions.

If the TAT polypeptide is intracellular and whole antibodies are used as inhibitors, internalizing antibodies are preferred. However, lipofections or liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., Proc. Natl. Acad. Sci. USA, 90: 7889-7893 (1993).

The formulation herein may also contain more than one active compound as necessary for the particular indication being treated, preferably those with complementary activities that do not adversely affect each other. Alternatively, or in addition, the composition may comprise an agent that enhances its function, such as, for example, a cytotoxic agent, cytokine, chemotherapeutic agent, or growth-inhibitory agent. Such molecules are suitably present in combination in amounts that are effective for the purpose intended.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example 1: Tissue Expression Profiling Using GeneExpress®

A proprietary database containing gene expression information (GeneExpress®, Gene Logic Inc., Gaithersburg, Md.) was analyzed in an attempt to identify polypeptides (and their encoding nucleic acids) whose expression is significantly and detectably upregulated in a particular human tumor tissue(s) of interest as compared to other human tumor(s) and/or normal human tissues. Specifically, analysis of the GeneExpress® database was conducted using either software available through Gene Logic Inc., Gaithersburg, Md., for use with the GeneExpress® database or with proprietary software written and developed at Genentech, Inc. for use with the GeneExpress® database. The rating of positive hits in the analysis is based upon several criteria including, for example, tissue specificity, tumor specificity and expression level in normal essential and/or normal proliferating tissues. Using this mRNA expression analysis, it was determined that mRNA encoding the TAT419 polypeptide is significantly, reproducibly and detectably overexpressed in human melanoma cancer tissue as compared to the corresponding normal human skin tissue.

Example 2: In Situ Hybridization

In situ hybridization is a powerful and versatile technique for the detection and localization of nucleic acid sequences within cell or tissue preparations. It may be useful, for example, to identify sites of gene expression, analyze the tissue distribution of transcription, identify and localize viral infection, follow changes in specific mRNA synthesis and aid in chromosome mapping.

In situ hybridization was performed following an optimized version of the protocol by Lu and Gillett, Cell Vision 1:169-176 (1994), using PCR-generated $^{32}$P-labeled riboprobes. Briefly, formalin-fixed, paraffin-embedded human tissues were sectioned, deparaffinized, deproteinated in proteinase K (20 g/ml) for 15 minutes at 37° C., and further processed for in situ hybridization as described by Lu and Gillett, supra. A $^{32}$P-UTP-labeled antisense riboprobe was generated from a PCR product and hybridized at 55° C. overnight. The slides were dipped in Kodak NTB2 nuclear track emulsion and exposed for 4 weeks.

$^{32}$P-Riboprobe Synthesis 6.0 µl (125 mCi) of $^{32}$P-UTP (Amersham BF 1002, SA<2000 Ci/mmol) were speed vac dried. To each tube containing dried $^{32}$P-UTP, the following ingredients were added: 2.0 µl 5× transcription buffer, 1.0 µl DTT (100 mM), 2.0 µl NTP mix (2.5 mM: 10µ; each of 10 mM GTP, CTP & ATP+10 µl H$_2$O), 1.0 µl UTP (50 µM), 1.0 µl Rnasin, 1.0 µl DNA template (1 µg), 1.0 µl H$_2$O, 1.0 µl RNA polymerase (for PCR products T3=AS, T7=S, usually).

The tubes were incubated at 37° C. for one hour. 1.0 µl RQ1 DNase were added, followed by incubation at 37° C. for 15 minutes. 90 µl TE (10 mM Tris pH 7.6/1 mM EDTA pH 8.0) were added, and the mixture was pipetted onto DE81 paper. The remaining solution was loaded in a Microcon-50 ultrafiltration unit, and spun using program 10 (6 minutes). The filtration unit was inverted over a second tube and spun using program 2 (3 minutes). After the final recovery spin, 100 µl TE were added. 1 µl of the final product was pipetted on DE81 paper and counted in 6 ml of Biofluor II.

The probe was run on a TBE/urea gel. 1-3 µl of the probe or 5 µl of RNA Mrk III were added to 3 µl of loading buffer. After heating on a 95° C. heat block for three minutes, the probe was immediately placed on ice. The wells of gel were flushed, the sample loaded, and run at 180-250 volts for 45 minutes. The gel was wrapped in saran wrap and exposed to XAR film with an intensifying screen in −70° C. freezer one hour to overnight.

$^{32}$P-Hybridization

A. Pretreatment of Frozen Sections

The slides were removed from the freezer, placed on aluminium trays and thawed at room temperature for 5 minutes. The trays were placed in 55° C. incubator for five minutes to reduce condensation. The slides were fixed for 10 minutes in 4% paraformaldehyde on ice in the fume hood, and washed in 0.5×SSC for 5 minutes, at room temperature (25 ml 20×SSC+975 ml SQ H2O). After deproteination in 0.5 µg/ml proteinase K for 10 minutes at 37° C. (12.5 µl of 10 mg/ml stock in 250 ml prewarmed RNase-free RNAse buffer), the sections were washed in 0.5×SSC for 10 minutes at room temperature. The sections were dehydrated in 70%, 95%, 100% ethanol, 2 minutes each.

B. Pretreatment of Paraffin-Embedded Sections

The slides were deparaffinized, placed in SQ H2O, and rinsed twice in 2×SSC at room temperature, for 5 minutes each time. The sections were deproteinated in 20 µg/ml proteinase K (500 µl of 10 mg/ml in 250 ml RNase-free RNase buffer; 37° C., 15 minutes)—human embryo, or 8× proteinase K (100 µl in 250 ml Rnase buffer, 37° C., 30 minutes)-formalin tissues. Subsequent rinsing in 0.5×SSC and dehydration were performed as described above.

C. Prehybridization

The slides were laid out in a plastic box lined with Box buffer (4×SSC, 50% formamide)—saturated filter paper.

D. Hybridization 1.0×106 cpm probe and 1.0 µl tRNA (50 mg/ml stock) per slide were heated at 95° C. for 3 minutes. The slides were cooled on ice, and 48 µl hybridization buffer were added per slide. After vortexing, 50 µl $^{32}$P mix were added to 50 µl prehybridization on slide. The slides were incubated overnight at 55° C.

E. Washes

Washing was done 2×10 minutes with 2×SSC, EDTA at room temperature (400 ml 20×SSC+16 ml 0.25M EDTA, Vf=4L), followed by RNaseA treatment at 37° C. for 30 minutes (500 µl of 10 mg/ml in 250 ml Rnase buffer=20 µg/ml). The slides were washed 2×10 minutes with 2×SSC, EDTA at room temperature. The stringency wash conditions were as follows: 2 hours at 55° C., 0.1×SSC, EDTA (20 ml 20×SSC+16 ml EDTA, Vf=4L).

F. Oligonucleotides

In situ analysis was performed on a variety of DNA sequences disclosed herein. The oligonucleotides employed for these analyses were obtained so as to be complementary to the nucleic acids (or the complements thereof) as shown in the accompanying figures.

G. Results

With regard to TAT419, weak or no observable expression is observed in the majority of normal tissues tested. In contrast, strong and quantitatively reproducible TAT419 expression was observed in a majority of human melanoma cells and tissues tested.

Example 3: Microarray Analysis to Detect Upregulation of TAT Polypeptides in Cancerous Tumors Nucleic acid microarrays, often containing thousands of gene sequences, are useful for identifying differentially expressed genes in diseased tissues as compared to their normal counterparts. Using nucleic acid microarrays, test and control mRNA samples from test and control tissue samples are reverse transcribed and labeled to generate cDNA probes. The cDNA probes are then hybridized to an array of nucleic acids immobilized on a solid support. The array is configured such that the sequence and position of each member of the array is known. For example, a selection of genes known to be expressed in certain disease states may be arrayed on a solid support. Hybridization of a labeled probe with a particular array member indicates that the sample from which the probe was derived expresses that gene. If the hybridization signal of a probe from a test (disease tissue) sample is greater than hybridization signal of a probe from a control (normal tissue) sample, the gene or genes overexpressed in the disease tissue are identified. The implication of this result is that an overexpressed protein in a diseased tissue is useful not only as a diagnostic marker for the presence of the disease condition, but also as a therapeutic target for treatment of the disease condition.

The methodology of hybridization of nucleic acids and microarray technology is well known in the art. In the present example, the specific preparation of nucleic acids for hybridization and probes, slides, and hybridization conditions are all detailed in PCT Patent Application Serial No. PCT/US01/10482, filed on Mar. 30, 2001 and which is herein incorporated by reference.

In the present example, cancerous tumors derived from various human tissues were studied for upregulated gene expression relative to cancerous tumors from different tissue types and/or non-cancerous human tissues in an attempt to identify those polypeptides which are overexpressed in a particular cancerous tumor(s). In certain experiments, cancerous human tumor tissue and non-cancerous human tumor tissue of the same tissue type (often from the same patient) were obtained and analyzed for TAT polypeptide expression. Additionally, cancerous human tumor tissue from any of a variety of different human tumors was obtained and compared to a "universal" epithelial control sample which was prepared by pooling non-cancerous human tissues of epithelial origin, including liver, kidney, and lung. mRNA isolated from the pooled epithelial tissues represents a mixture of expressed gene products from various different epithelial tissues, thereby providing an excellent negative control against which to quantitatively compare gene expression levels in tumors of epithelial origin. Microarray hybridization experiments using the pooled control samples generated a linear plot in a 2-color analysis. The slope of the line generated in a 2-color analysis was then used to normalize the ratios of (test:control detection) within each experiment. The normalized ratios from various experiments were then compared and used to identify clustering of gene expression. Thus, the pooled "universal control" sample not only allowed effective relative gene expression determinations in a simple 2-sample comparison, it also allowed multi-sample comparisons across several experiments.

In the present experiments, nucleic acid probes derived from the herein described TAT polypeptide-encoding nucleic acid sequences were used in the creation of the microarray and RNA from various tumor tissues were used for the hybridization thereto. A value based upon the normalized ratio:experimental ratio was designated as a "cutoff ratio". Only values that were above this cutoff ratio were determined to be significant. Significance of ratios were estimated from the amount of noise or scatter associated with each experiment, but typically, a ratio cutoff of 1.8 fold-2 fold or greater was used to identify candidate genes relatively overexpressed in tumor samples compared to the corresponding normal tissue and/or the pooled normal epithelial universal control. Ratios for genes identified in this way as being relatively overexpressed in tumor samples varied from 2 fold to 40 fold, or even greater. By comparison, in a control experiment in which the same RNA was labeled in each color and hybridized against itself, for virtually all genes with signals above background, the observed ratio is significantly less than 1.8 fold. This indicates that experimental noise above a ratio of 1.8 fold is extremely low, and that an observed fold change of 1.8 fold or greater is expected to represent a real, detectably and reproducible difference in expression between the samples analyzed and compared.

The data from these experiments demonstrated that TAT419 polypeptide is significantly, detectably and reproducibly overexpressed in human melanoma tumor tissues and derived cell lines as compared to the normal counterpart human tissues or cells and/or the pooled normal epithelial control tissue. As described above, these data demonstrate that the TAT419 polypeptides of the present invention are useful not only as diagnostic markers for the presence of one or more cancerous tumors in humans, but also serve as therapeutic targets for the treatment of those cancerous tumors that overexpress TAT419 polypeptide.

Example 4: Preparation of Antibodies that Bind to TAT419 Polypeptides

This example illustrates preparation of monoclonal antibodies which can specifically bind TAT419.

Techniques for producing the monoclonal antibodies are known in the art and are described, for instance, in Goding, supra. Immunogens that may be employed include purified TAT, fusion proteins containing TAT, and cells expressing recombinant TAT on the cell surface. Selection of the immunogen can be made by the skilled artisan without undue experimentation.

Mice, such as Balb/c, are immunized with the TAT immunogen emulsified in complete Freund's adjuvant and injected subcutaneously or intraperitoneally in an amount from 1-100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-TAT antibodies.

After a suitable antibody titer has been detected, the animals "positive" for antibodies can be injected with a final intravenous injection of TAT. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against TAT. Determination of "positive" hybridoma cells secreting the desired monoclonal antibodies against TAT is within the skill in the art.

The positive hybridoma cells can be injected intraperitoneally into syngeneic Balb/c mice to produce ascites containing the anti-TAT monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Using the above described technique, a variety of separate and distinct hybridoma cell lines have been generated, each of which produce monoclonal antibodies that bind to TAT419 polypeptide. The monoclonal antibodies produced by these hybridoma lines are functional in that they have been shown to bind to the TAT419 polypeptide using well-known and routinely employed techniques such as Western blot, ELISA analysis, FACS sorting analysis of cells expressing the TAT419 polypeptide (both cells transfected to express the TAT419 polypeptide on the cell surface and certain human melanoma tumor cell lines that express TAT419 polypeptide) and/or immunohistochemistry analysis.

Example 5: Molecular Cloning of the Light and Heavy Chains (and Variable Light and Variable Heavy Chains) of Anti-TAT419 Murine Monoclonal Antibody 5E9

One of the anti-TAT419 murine monoclonal antibodies generated as described above was herein designated as 5E9. This example demonstrates the preparation of cDNA molecules encoding the variable regions of the murine anti-TAT419 monoclonal antibody 5E9. Forward PCR primers were designed such that they are specific for the mRNA encoding the beginning of the nucleotide sequence of the $V_L$ and $V_H$ regions of the murine monoclonal antibody 5E9. The forward primers were designed such that the majority of the possible codons for the first 8-9 N-terminal amino acids would hybridize to the PCR primer.

Hybridoma cells expressing the anti-TAT419 murine monoclonal antibodies were used as sources for antibody mRNA together with the above oligonucleotide primers. Total RNA was isolated from $1 \times 10^8$ cells using the procedure described by Chomczynski and Sachhi 1987 *Anal. Biochem.* 162:156. The variable light ($V_L$) and variable heavy ($V_H$) domains were amplified using RT-PCR with the above degenerate N-terminal primers together with reverse primers that were designed to anneal to a region in the constant light (CL) and constant heavy domain 1 (CH1), which are highly conserved across species.

The forward primers were specific for the N-terminal amino acid sequence of the $V_L$ and $V_H$ regions. Respectively, the LC and HC reverse primers were designed to anneal to a region in the constant light (CL) and constant heavy domain 1 (CH1), which are highly conserved across species. The polynucleotide sequence of the inserts was determined using routine sequencing methods. The full-length light (SEQ ID NO:3) and full-length heavy (SEQ ID NO:4) chain sequences of the murine 5E9 monoclonal antibody are shown in FIGS. 3 and 4, respectively. The $V_L$ (SEQ ID NO:5) and $V_H$ (SEQ ID NO:6) amino acid sequences of the murine 5E9 monoclonal antibody are also shown in FIGS. 3 and 4, respectively. Further characterization of these amino acid sequences showed the following amino acid sequences for the various CDR regions of the murine anti-TAT419 5E9 monoclonal antibody: CDR-L1 (KSSQSLLDSDGKTYLN, SEQ ID NO:7), CDR-L2 (LVSKLDS, SEQ ID NO:8), CDR-L3 (WQGTHFPYT; SEQ ID NO:9), CDR-H1 (GYTFTSYWMQ; SEQ ID NO:10), CDR-H2 (TIYPGDGDTSYAQKFKG; SEQ ID NO:11), and CDR-H3 (WGYAYDIDN; SEQ ID NO:12).

The amplified $V_L$ and $V_H$ cDNAs of the antibody light and heavy chains were subsequently cloned into pRK mammalian cell expression vectors. (Shields et al 2000 *J. Biol. Chem.* 276:659-604) The amplified variable light chain $V_L$ cDNA was cloned into a pRK mammalian cell expression vector containing the human kappa constant domain using the sites for EcoRV and KpnI (pRK.LPG3.HumanKappa; Genentech, South San Francisco, Calif.). The amplified variable heavy chain $V_H$ cDNA was inserted into pRK mammalian cell expression vector encoding the full-length human IgG1 constant domain (pRK.LPG4.HumanHC; Genentech) using sites for BsiWI and ApaI.

Example 6: Immunohistochemistry Analysis

Antibodies against TAT419 polypeptide were prepared as described above and employed in immunohistochemistry analysis as follows. Tissue sections were first fixed for 5 minutes in acetone/ethanol (frozen or paraffin-embedded). The sections were then washed in PBS and then blocked with avidin and biotin (Vector kit) for 10 minutes each followed by a wash in PBS. The sections were then blocked with 10% serum for 20 minutes and then blotted to remove the excess. A primary antibody was then added to the sections at a concentration of 10 μg/ml for 1 hour and then the sections were washed in PBS. A biotinylated secondary antibody (anti-primary antibody) was then added to the sections for 30 minutes and then the sections were washed with PBS. The sections were then exposed to the reagents of the Vector ABC kit for 30 minutes and then the sections were washed in PBS. The sections were then exposed to Diaminobenzidine (Pierce) for 5 minutes and then washed in PBS. The sections were then counterstained with Mayers hematoxylin, covered with a coverslip and visualized. Immunohistochemistry analysis can also be performed as described in Sambrook et al., Molecular Cloning: A Laboratory Manual, New York: Cold Spring Harbor Press, 1989 and Ausubel et al., Current Protocols of Molecular Biology, Unit 3.16, John Wiley and Sons (1997).

The results from these analyses demonstrate that the monoclonal antibody employed in these analyses identified observable TAT419 expression in approximately 90% of all independent primary human melanoma cancer samples tested, wherein approximately 65% of those evidenced moderate (2+) to high (3+) expression of the TAT419 polypeptide.

Example 7: Humanization of Murine Monoclonal Antibodies

This example demonstrates the applicability of methods to humanize the murine antibody 5E9 directed against TAT419.

An extracellular domain of TAT419 was expressed in *E. coli* (unglycosylated) and as an immunoadhesin (Fc fusion) in CHO (glycosylated) cells and purified by conventional means. A murine hybridoma expressing the antibody 5E9 was obtained by immunizing mice with the recombinant TAT419 extracellular domain derived from *E. coli* and identified by its ability to bind to TAT419 coated plates by ELISA.

Cloning of the Murine 5E9 Variable Domains

Total RNA was extracted from hybridoma cells producing 5E9 using standard methods. The variable light (VL) and variable heavy (VH) domains were amplified using RT-PCR with degenerate primers to the heavy and light chains. The forward primers were specific for the N-terminal amino acid sequence of the VL and VH regions. Respectively, the LC and HC reverse primers were designed to anneal to a region in the constant light (CL) and constant heavy domain 1 (CH1), which are highly conserved across species. The polynucleotide sequence of the inserts was determined using routine sequencing methods.

Direct Hypervariable Region Grafts onto the Acceptor Human Consensus Framework

The phagemid used for this work is a monovalent Fab-g3 display vector and consists of 2 open reading frames under control of a single phoA promoter. The first open reading frame consists of the stII signal sequence fused to the VL and CH1 domains of the acceptor light chain and the second consists of the stII signal sequence fused to the VH and CH1 domains of the acceptor heavy chain followed by the minor phage coat protein P3.

The VL and VH domains from murine 5E9 were aligned with the human VL kappa I (huKI) and human VH subgroup III (huIII) consensus sequences. To make the CDR graft, hypervariable regions from 5E9 were grafted into the huKI and huIII consensus acceptor frameworks to generate "5E9-graft", the direct CDR-graft. In the VL domain the following regions were grafted to the human consensus acceptor: positions 24-34 (L1), 50-56 (L2) and 89-97 (L3). In the VH domain, positions 26-35 (H1), 49-65 (H2) and 93-102 (H3) were grafted. MacCallum et al. (J. Mol. Biol. 262: 732-745 (1996)) have analyzed antibody and antigen complex crystal structures and found position 49 and 93 of the heavy chain to be part of the contact region thus it seems reasonable to include these positions in the definition of CDR-H2 and CDR-H3 when humanizing antibodies.

"5E9-graft" was generated as IgG by Kunkel mutagenesis of LC and HC expression vectors using separate oligonucleotides for each hypervariable region. Amino acid changes to increase affinity or stability were also made using Kunkel mutagenesis. Correct clones were identified by DNA sequencing.

Randomization of the Hypervariable Regions

Sequence diversity was introduced separately into each hypervariable region of 5E9-graft using a soft randomization strategy that maintains a bias towards the murine hypervariable region sequence. This was accomplished using a poisoned oligonucleotide synthesis strategy first described by Gallop et al., J. Med. Chem. 37:1233-1251 (1994). For a given position within a hypervariable region to be mutated, the codon encoding the wild-type amino acid is poisoned with a 70-10-10-10 mixture of nucleotides resulting in an average 50 percent mutation rate at each position.

Soft randomized oligonucleotides were patterned after the murine hypervariable region sequences and encompassed the same regions defined by the direct hypervariable region grafts. The amino acid position at the beginning of H2 (position 49) in the VH domain, was limited in sequence diversity to A, G, S or T by using the codon RGC.

To avoid reselecting the wild type CDR grafted sequence, a stop codon (TAA) was introduced in the middle of each CDR of 5E9-graft by Kunkel mutagenesis resulting in 6 different templates, each with a stop codon introduced into a different CDR. Randomized oligonucleotides were used to introduce diversity as well as to repair the stop codon in the corresponding template.

Generation of Phage Libraries

Randomized oligonucleotide pools designed to introduce diversity into each hypervariable region as outlined above, were phosphorylated separately in 20 µl reactions containing 660 ng of oligonucleotide, 50 mM Tris pH 7.5, 10 mM MgCl2, 1 mM ATP, 20 mM DTT, and 5 U polynucleotide kinase for 1 h at 37° C.

Each phosphorylated oligonucleotide pool directed to introduce diversity into a single CDR was combined with 20 µg of Kunkel template containing the corresponding stop codon. The reaction was performed in 50 mM Tris pH 7.5, 10 mM $MgCl_2$ in a final volume of 500 µl resulting in a oligonucleotide to template ratio of 3. The mixture was annealed at 90° C. for 4 min, 50° C. for 5 min and then cooled on ice. The annealed template (250 µl) was then filled in by adding 1 µl 100 mM ATP, 10 µl 25 mM dNTPs (25 mM each of dATP, dCTP, dGTP and dTTP), 15 µl 100 mM DTT, 25 µl 10×TM buffer (0.5 M Tris pH 7.5, 0.1 M $MgCl_2$), 2400 U T4 ligase, and 30 U T7 polymerase for 3 hours at room temperature. The filled in product was then cleaned-up and electroporated into SS320 cells and propagated in the presence of M13/KO7 helper phage as described by Sidhu et al., Methods in Enzymology 328:333-363 (2000). Library sizes ranged from 1-2×109 independent clones. Random clones from the initial libraries were sequenced to assess library quality.

Phage Selection

For the phage selections, CHO derived TAT419 extracellular domain (2 µg/ml) was immobilized in PBS on MaxiSorp microtiter plates (Nunc) overnight at 4° C. Plates were blocked for at least 1 h using Casein Blocker (Pierce). Phage were harvested from the culture supernatant and suspended in PBS containing 0.5% BSA and 0.05% Tween 20 (PBSBT). Following phage selection, microtiter wells were washed extensively with PBS containing 0.05% Tween 20 (PBST) and bound phage were eluted by incubating the wells with 100 mM HCl for 30 min. Phage were neutralized with 1 M Tris, pH 8 and amplified using XL1-Blue cells and M13/KO7 helper phage and grown overnight at 37° C. in 2YT, 50 µg/ml carbenacillin. The titers of phage eluted from a target containing well were compared to titers of phage recovered from a non-target containing well to assess enrichment.

Fab and IgG Production

To express Fab protein for affinity measurements, a stop codon was introduced between the heavy chain and g3 in the phage display vector. Clones were transformed into E. coli 34B8 cells and grown in Complete C.R.A.P. media at 30° C. (Presta et al. Cancer Res. 57: 4593-4599 (1997)). Cells were harvested by centrifugation, suspended in PBS, 100 uM PMSF, 100 uM benzamidine, 2.5 mM EDTA and broken open using a microfluidizer. Fab was purified with Protein G affinity chromatography.

For screening purposes, IgG variants were initially produced in 293 cells. Vectors coding for VL and VH (25 µg) were transfected into 293 cells using the FuGene system. 500 µl of FuGene was mixed with 4.5 ml of DMEM media containing no FBS and incubated at room temperature for 5 min. Each chain (25 µg) was added to this mixture and incubated at room temperature for 20 min and then transferred to five T-150 flasks for transfection overnight at 37° C. in 5% $CO_2$. The following day the media containing the transfection mixture is removed and replaced with 23 ml PS04 media with 0.1 ml/L trace elements (A0934) and 10 mg/L insulin (A0940). Cells were incubated for an additional 5 days after which the media was harvested at 1000 rpm for 5 min and sterile filtered using a 0.22 µm low protein-binding filter. Samples could be stored at 4° C. after addition of 2.5 ml 0.1% PMSF for every 125 ml of media. The IgG was purified using Protein G affinity chromatography.

Affinity Determinations

Affinity determinations were performed by Scatchard analysis and by surface plasmon resonance using a BIAcore™-2000 or A100.

Biacore 2000

TAT419 extracellular domain (glycosylated) was immobilized (approximately 100-400 RU, in 10 mM Sodium Acetate pH 4.8 on a CM5 sensor chip) and the 5E9 antibody variant served as the analyte (injected at a flow rate of 30 µL/min, using a 2-fold serial dilution of 4 to 1000 nM in PBST). Each sample was analyzed with 4-minute association and 10-minute disassociation. After each injection the chip was regenerated using 10 mM Glycine pH 1.7.
Results and Discussion The human acceptor framework used for humanization is based on the consensus human kappa I VL domain and the consensus human subgroup III VH domain. The VL and VH domains of 5E9 were aligned with the human kappa I and subgroup III domains; each complementarity determining region (CDR) was identified and grafted into the human acceptor framework to generate a CDR graft that could be expressed as an IgG (5E9-graft).

Fab displaying phage libraries were generated in which diversity was introduced separately into each CDR of 5E9-graft and panned against CHO derived TAT419 extracellular domain. Enrichment was observed after the second round in all 6 libraries. Following round 6, clones were picked for DNA sequence analysis from each library and revealed sequence changes targeted at each of the six CDRs. These sequence changes identified from the library could represent changes that lead to variants with improved binding or simply indicate amino acid changes at positions that have no impact on TAT419 extracellular domain binding.

Several selected clones were expressed as Fab and characterized for binding to TAT419 extracellular domain by Biacore. All clones bound to TAT419 on the surface of cells and most clones bound with affinities greatly improved relative to 5E9-graft.

The humanized anti-TAT419 antibody designated herein as hu5E9.v1, having the full-length light chain amino acid sequence shown in FIG. 5 (SEQ ID NO:13), the full-length heavy chain amino acid sequence shown in FIG. 6 (SEQ ID NO:14), the VL amino acid sequence shown in FIG. 5 (SEQ ID NO:15), and the VH amino acid sequence shown in FIG. 6 (SEQ ID NO:16), was shown to bind to TAT419 on the surface of cells with a higher affinity than does murine 5E9 and, as such, was chosen as a lead candidate for further development. The various CDR sequences of the hu5E9.v1 are as follows: CDR-L1 (KSSQSLLDSDGKTYLN, SEQ ID NO:7), CDR-L2 (LVSKLDS, SEQ ID NO:8), CDR-L3 (WQGTHFPYT; SEQ ID NO:9), CDR-H1 (GYTFTSY-WMQ; SEQ ID NO:10), CDR-H2 (TIYPGDGDTSYAQK-FKG; SEQ ID NO:11), and CDR-H3 (WGYAYDIDN; SEQ ID NO:12).

A second humanized anti-TAT419 antibody designated herein as hu5E9.v2 was also identified, having the same VL sequence (SEQ ID NO:15) as hu5E9.v1 and a VH amino acid sequence as shown in FIG. 7 (SEQ ID NO:17).

Example 8: Binding Analyses and TAT419 Epitope Mapping

Binding affinity of the various anti-TAT419 antibodies can be determined by surface plasmon resonance using Pharmacia BIAcore® 3000 (BIAcore AB, Uppsala, Sweden) at room temperature (see, e.g., Morton et al 1998 *Methods in Enzymology*, 295, 268-294). The various anti-TAT419 antibodies are immobilized to the sensor chip (CM5) through primary amine groups. The carboxymethylated sensor chip surface matrix is activated by injecting 20 ml of a mixture of 0.025 M N-hydroxysuccinimide and 0.1 M N-ethyl-N'(dimethylaminopropyl) carbodiimide at 5 ml/min. 5-10 ml of 10 mg/ml solution of anti-TAT419 antibodies in 10 mM sodium acetate, pH 4.5, this is injected at 5 ml/min. After coupling, unoccupied sites on the chip are blocked by injecting 20 ml of 1M ethanolamine, pH 8.5. The running buffer is PBS containing 0.05% polysorbate 20. For kinetic measurements, two-fold serial dilutions of the various anti-TAT419 antibodies in running buffer are injected over the flow cells for 3 minutes at a flow rate of 30 ml/min and the bound material is allow to dissociate for 20 minutes. The binding surface is regenerated by injecting 20 ml of 10 mM glycine.HCl (pH 1.5). Flow cell one, which is activated but does not have antibody immobilized, is used as a reference cell. There is negligible non-specific binding of material to flow cell one. For the calculation of apparent binding affinity, data are analyzed using a 1:1 binding model using global fitting. The association and dissociation rate constants are fitted simultaneously (BIA evaluation software).

The TAT419 epitopes bound by the various monoclonal antibodies described above are determined by standard competitive binding analysis (Fendly et al 1990 Cancer Research 50:1550-1558). Cross-blocking studies are done on antibodies by direct fluorescence using the PANDEX™ Screen Machine to quantitate fluorescence, on intact cells engineered to express the TAT419 polypeptide.

Each monoclonal antibody is conjugated with fluorescein isothiocyanate (FITC), using established procedures (Wofsy et al 1980 *Selected Methods in Cellular Immunology*, p. 287, Eds. Mishel and Schiigi San Francisco: W.J. Freeman Co.). The samples tested as were confluent monolayers of TAT419-expressing cells that were trypsinized, washed once, and resuspended at $1.75 \times 10^6$ cell/ml in cold PBS containing 0.5% bovine serum albumin (BSA) and 0.1% NaN3. A final concentration of 1% latex particles (IDC, Portland, Oreg.) was added to reduce clogging of the PANDEX™ plate membranes. Cells in suspension, 20 µl, and 20 µl of purified monoclonal antibodies (100 µg/ml to 0.1 µg/ml) were added to the PANDEX™ plate wells and incubated on ice for 30 minutes. A predetermined dilution of FITC-labeled monoclonal antibodies in 20 µl was added to each well, incubated for 30 minutes, washed, and the PANDEX™ Screen Machine quantitated the fluorescence. Monoclonal antibodies were considered to share an epitope only if they blocked the binding of itself equal to that of the second monoclonal. In this experiment, the murine monoclonal antibodies designated herein as 5E9 and 3C3 were each assigned to different epitopes on cell surface expressed TAT419 polypeptide. Using this assay, one of ordinary skill in the art can identify other monoclonal antibodies that bind to the same epitopes as those described herein.

Binding analysis was also conducted to identify the approximate location of the epitopes. Several TAT419-derived peptide variants were expressed in 293 cells. Western blots were carried out using various of the murine anti-TAT419 monoclonal antibodies described herein. Results from these analyses demonstrated that the 5E9 murine anti-TAT419 antibody recognized and bound to 293 cells expressing the full-length TAT419 polypeptide, whereas a second, independent murine anti-TAT419 monoclonal antibody did not recognize nor bind to 293 cells expressing a TAT419 polypeptide with a section of its N-terminus deleted, suggesting the identification of two separate, distinct epitopes.

More specifically, certain murine anti-TAT419 monoclonal antibodies tested herein were shown to bind to an epitope (or epitopes) located between the 27th and 64th amino acid of the TAT419 sequence shown herein as SEQ ID NO:2. Moreover, other murine anti-TAT419 monoclonal antibodies (including the murine 5E9 monoclonal antibody, and the various humanized versions thereof) were shown to bind to an epitope (or epitopes) located between 65th and 101st amino acid of the TAT419 polypeptide sequence shown herein as SEQ ID NO:2.

Example 9: Anti-TAT419 Antibodies are Internalized by Cells that Express TAT419 Polypeptide Cellular internalization of anti-TAT419 antibodies was investigated with cells that express TAT419 on their surface. In order to investigate the fate of antibodies that are bound to TAT419, samples of TAT419-expressing melanoma cell lines were incubated with the various anti-TAT419 antibodies on ice for one hour then fixed for staining with a secondary antibody. The secondary antibody was either anti-murine Cy3 for the 5E9 murine monoclonal antibody and the other anti-TAT419 murine monoclonal antibodies tested, or anti-human Cy3 for chimeric versions of the murine monoclonal antibodies. Significant plasma membrane staining by the murine monoclonal antibodies was observed with the TAT419-expressing cells using a Deconvolution Microscope, indicating the formation of an antibody-cell surface protein complex.

For continued methods, see "Internalization studies" in Polson et al., *Blood* 110(2):616-23 (2007) at page 618. Immunofluorescence showed cell surface staining and internalization when visualized using Deconvolution Microscopy, 60× Magnification.) Control cells that do not express TAT419 did not evidence plasma membrane staining. These observations were compared with cells that were kept on ice for one hour then shifted to 37° C. for 2 hours. Significant plasma membrane staining and internal cell staining was observed using both the murine 5E9 and 3C3 anti-TAT419 antibodies with the TAT419-expressing cells, indicating the trafficking of the antibody-cell surface protein complex into the cell itself. Further antibody/TAT419 complex uptake was observed after overnight incubation.

Plasma membrane staining with 5E9 was carried out for 1 hour with incubation at 4° C. then the cells were fixed and treated with a secondary antibody, "Cy3 mouse". Internalization was demonstrated after 2 hours or after overnight incubation at 37° C. followed by fixation and treatment with the secondary antibody.

Cells were seeded in 8-well chamber slides (Nalge Nunc Intl.) (abt. 100,000 cells/well) and incubated at 37° C./5% $CO_2$ for 24-48 hours. Anti-TAT419 antibodies were added at 2-5 ug/ml in growth media either overnight or for 2 hours with protease inhibitors (50 ug/ml Leupeptin and 5 ug/ml Pepstatin). These protease inhibitors prevent degradation of the primary antibody, allowing detection of the antibody in lysosomes. For live labelling, cells were incubated with antibodies at room temperature for 45 minutes. All cells were then washed, fixed in 3% formaldehyde for 10 minutes, permeabilized with 0.05% saponin for 5-10 minutes and non-specific antibody binding sites blocked by PBS+1% BSA for 20 minutes at room temperature. Cells were then incubated with secondary antibody labelled with Alexa-488 (Molecular Probes) at 37° C. for 1 hour, washed and then chamber inserts were removed to expose the glass slide with cells. Slides were mounted by applying VectaShield with DAPI to label nuclei (Vector Laboratories), then placed under a glass coverslip and sealed with clear nail polish.

The results from these analyses demonstrated that the various anti-TAT419 antibodies described herein (including the murine 5E9 monoclonal antibody, and the various humanized versions thereof) bind to TAT419 polypeptide on the surface of live cells and are rapidly internalized into the cell and located to the lysosomes of the cell within less than 20 hours after addition of the antibodies to the cells. As such, the anti-TAT419 antibodies described herein are excellent candidates for toxin-conjugated tumor therapy for tumors that express TAT419 polypeptides.

Example 10: Preparation of Toxin-Conjugated Antibodies that Bind TAT419

The use of antibody-drug conjugates (ADC), i.e. immunoconjugates, for the local delivery of cytotoxic or cytostatic agents, i.e. drugs to kill or inhibit tumor cells in the treatment of cancer (Payne (2003) Cancer Cell 3:207-212; Syrigos and Epenetos (1999) Anticancer Research 19:605-614; Niculescu-Duvaz and Springer (1997) Adv. Drug Del. Rev. 26:151-172; U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) Lancet (Mar. 15, 1986) pp. 603-05; Thorpe, (1985) "Antibody Carriers Of Cytotoxic Agents In Cancer Therapy: A Review," in Monoclonal Antibodies '84: Biological And Clinical Applications, Pinchera et al. (eds.), pp. 475-506). Maximal efficacy with minimal toxicity is sought thereby. Efforts to design and refine ADC have focused on the selectivity of monoclonal antibodies (mAbs) as well as drug-linking and drug-releasing properties. Both polyclonal antibodies and monoclonal antibodies have been reported as useful in these strategies (Rowland et al., (1986) Cancer Immunol. Immunother., 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al. (2000) J. of the Nat. Cancer Inst. 92(19): 1573-1581; Mandler et al. (2000) Bioorganic & Med. Chem. Letters 10:1025-1028; Mandler et al. (2002) Bioconjugate Chem. 13:786-791), maytansinoids (EP 1391213; Liu et al., (1996) Proc. Natl. Acad. Sci. USA 93:8618-8623), and calicheamicin (Lode et al. (1998) Cancer Res. 58:2928; Hinman et al. (1993) Cancer Res. 53:3336-3342).

In the antibody drug conjugates (ADC) of the invention, an antibody (Ab) is conjugated to one or more drug moieties (D), e.g. about 1 to about 20 drug moieties per antibody, through a linker (L). The ADC having the formula:

Ab-(L-D)p may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody. Additional methods for preparing ADC are described herein.

The linker may be composed of one or more linker components. Exemplary linker components include 6-maleimidocaproyl ("MC"), maleimidopropanoyl ("MP"), valine-citrulline ("val-cit"), alanine-phenylalanine ("ala-phe"), p-aminobenzyloxycarbonyl ("PAB"), N-Succinimidyl 4-(2-pyridylthio)pentanoate ("SPP"), N-Succinimidyl 4-(N-maleimidomethyl)cyclohexane-1 carboxylate ("SMCC"), and N-Succinimidyl (4-iodo-acetyl)aminobenzoate ("SIAB"). Additional linker components are known in the art and some are described herein.

In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzyme, for example, a tumor-associated protease, cathepsin B, C and D, or a plasmin protease.

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, hydroxyl, hydrazide, oxime, hydrazine, thiosemicarbazone, hydrazine carboxylate, and arylhydrazide groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues).

Antibody drug conjugates of the invention may also be produced by modification of the antibody to introduce electrophilic moieties, which can react with nucleophilic substituents on the linker reagent or drug. The sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either glactose oxidase or sodium meta-periodate may yield carbonyl (aldehyde and ketone) groups in the protein that can react with appropriate groups on the drug (Hermanson, Bioconjugate Techniques). In another embodiment, proteins containing N-terminal serine or threonine residues can react with sodium meta-periodate, resulting in production of an aldehyde in place of the first amino acid (Geoghegan & Stroh, (1992) Bioconjugate Chem. 3:138-146; U.S. Pat. No. 5,362,852). Such aldehyde can be reacted with a drug moiety or linker nucleophile.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

Specific techniques for producing antibody-drug conjugates by linking toxins to purified antibodies are well known and routinely employed in the art. For example, conjugation of a purified monoclonal antibody to the toxin DM1 may be accomplished as follows. Purified antibody is derivatized with N-succinimidyl-4-(2-pyridylthio)pentanoate to introduce dithiopyridyl groups. Antibody (376.0 mg, 8 mg/mL) in 44.7 ml of 50 mM potassium phosphate buffer (pH 6.5) containing NaCl (50 mM) and EDTA (1 mM) is treated with SPP (5.3 molar equivalents in 2.3 ml ethanol). After incubation for 90 minutes under argon at ambient temperature, the reaction mixture is gel filtered through a Sephadex G25 column equilibrated with 35 mM sodium citrate, 154 mM NaCl and 2 mM EDTA. Antibody containing fractions are then pooled and assayed. Antibody-SPP-Py (337.0 mg with releasable 2-thiopyridine groups) is diluted with the above 35 mM sodium citrate buffer, pH 6.5, to a final concentration of 2.5 mg/ml. DM1 (1.7 equivalents, 16.1 mols) in 3.0 mM dimethylacetamide (DMA, 3% v/v in the final reaction mixture) is then added to the antibody solution. The reaction is allowed to proceed at ambient temperature under argon for 20 hours. The reaction is loaded on a Sephacryl S300 gel filtration column (5.0 cm×90.0 cm, 1.77 L) equilibrated with 35 mM sodium citrate, 154 mM NaCl, pH 6.5. The flow rate is 5.0 ml/min and 65 fractions (20.0 ml each) are collected. Fractions are pooled and assayed, wherein the number of DM1 drug molecules linked per antibody molecule (p') is determined by measuring the absorbance at 252 nm and 280 nm.

For illustrative purposes, conjugation of a purified monoclonal antibody to the toxin DM1 may also be accomplished as follows. Purified antibody is derivatized with (Succinimidyl 4-(N-maleimidomethyl)cyclohexane-1-carboxylate (SMCC, Pierce Biotechnology, Inc) to introduce the SMCC linker. The antibody is treated at 20 mg/ml in 50 mM potassium phosphate/50 mM sodium chloride/2 mM EDTA, pH 6.5 with 7.5 molar equivalents of SMCC (20 mM in DMSO, 6.7 mg/ml). After stirring for 2 hours under argon at ambient temperature, the reaction mixture is filtered through a Sephadex G25 column equilibrated with 50 mM potassium phosphate/50 mM sodium chloride/2 mM EDTA, pH 6.5. Antibody containing fractions are pooled and assayed. Antibody-SMCC is then diluted with 50 mM potassium phosphate/50 mM sodium chloride/2 mM EDTA, pH 6.5, to a final concentration of 10 mg/ml, and reacted with a 10 mM solution of DM1 (1.7 equivalents assuming 5 SMCC/antibody, 7.37 mg/ml) in dimethylacetamide. The reaction is stirred at ambient temperature under argon 16.5 hours. The conjugation reaction mixture is then filtered through a Sephadex G25 gel filtration column (1.5×4.9 cm) with 1×PBS at pH 6.5. The DM1/antibody ratio (p) is then measured by the absorbance at 252 nm and at 280 nm.

Moreover, a free cysteine on an antibody of choice may be modified by the bis-maleimido reagent BM(PEO)4 (Pierce Chemical), leaving an unreacted maleimido group on the surface of the antibody. This may be accomplished by dissolving BM(PEO)4 in a 50% ethanol/water mixture to a concentration of 10 mM and adding a tenfold molar excess to a solution containing the antibody in phosphate buffered saline at a concentration of approximately 1.6 mg/ml (10 micromolar) and allowing it to react for 1 hour. Excess BM(PEO)4 is removed by gel filtration in 30 mM citrate, pH 6 with 150 mM NaCl buffer. An approximate 10 fold molar excess DM1 is dissolved in dimethyl acetamide (DMA) and added to the antibody-BMPEO intermediate. Dimethyl formamide (DMF) may also be employed to dissolve the drug moiety reagent. The reaction mixture is allowed to react overnight before gel filtration or dialysis into PBS to remove unreacted drug. Gel filtration on S200 columns in PBS is used to remove high molecular weight aggregates and furnish purified antibody-BMPEO-DM1 conjugate.

Cytotoxic drugs have typically been conjugated to antibodies through the often numerous lysine residues of the antibody. Conjugation through thiol groups present, or engineered into, the antibody of interest has also been accomplished. For example, cysteine residues have been introduced into proteins by genetic engineering techniques to form covalent attachment sites for ligands (Better et al. (1994) J. Biol. Chem. 13:9644-9650; Bernhard et al. (1994) Bioconjugate Chem. 5:126-132; Greenwood et al. (1994) Therapeutic Immunology 1:247-255; Tu et al. (1999) Proc. Natl. Acad. Sci. USA 96:4862-4867; Kanno et al. (2000) J. of Biotechnology, 76:207-214; Chmura et al. (2001) Proc. Nat. Acad. Sci. USA 98(15):8480-8484; U.S. Pat. No. 6,248, 564). Once a free cysteine residue exists in the antibody of interest, toxins can be linked to that site. As an example, the drug linker reagents, maleimidocaproyl-monomethyl auristatin E (MMAE), i.e. MC-MMAE, maleimidocaproyl-monomethyl auristatin F (MMAF), i.e. MC-MMAF, MC-val-cit-PAB-MMAE or MC-val-cit-PAB-MMAF, dissolved in DMSO, is diluted in acetonitrile and water at known concentration, and added to chilled cysteine-derivatized antibody in phosphate buffered saline (PBS). After about one hour, an excess of maleimide is added to quench the reaction and cap any unreacted antibody thiol groups. The reaction mixture is concentrated by centrifugal ultrafiltration and the toxin conjugated antibody is purified and desalted by elution through G25 resin in PBS, filtered through 0.2m filters under sterile conditions, and frozen for storage.

Additionally, anti-TAT419 antibodies of the present invention may be conjugate to auristatin and dolostatin toxins (such as MMAE and MMAF) using the following technique. Antibody, dissolved in 500 mM sodium borate and 500 mM sodium chloride at pH 8.0 is treated with an excess of 100 mM dithiothreitol (DTT). After incubation at 37° C. for about 30 minutes, the buffer is exchanged by elution over Sephadex G25 resin and eluted with PBS with 1 mM DTPA. The thiol/Ab value is checked by determining the reduced antibody concentration from the absorbance at 280 nm of the solution and the thiol concentration by reaction with DTNB (Aldrich, Milwaukee, Wis.) and determination of the absorbance at 412 nm. The reduced antibody dissolved in PBS is chilled on ice.

The drug linker reagent, (1) maleimidocaproyl-monomethyl auristatin E (MMAE), i.e. MC-MMAE, (2) MC-MMAF, (3) MC-val-cit-PAB-MMAE, or (4) MC-val-cit-PAB-MMAF dissolved in DMSO, is diluted in acetonitrile and water at known concentration, and added to the chilled reduced antibody in PBS. After about one hour, an excess of maleimide is added to quench the reaction and cap any unreacted antibody thiol groups. The reaction mixture is concentrated by centrifugal ultrafiltration and the conjugated antibody is purified and desalted by elution through G25 resin in PBS, filtered through 0.2 m filters under sterile conditions, and frozen for storage.

Toxin-conjugated anti-TAT419 antibodies described herein were prepared as described and were tested using standard FACS analysis to determine whether conjugation to the toxin affected the antibody's ability to bind to TAT419 polypeptide on the surface of TAT419-expressing cells. The results from these analyses demonstrated that no loss in binding to TAT419 polypeptide was observed upon conjugation of the antibodies to the toxin.

Example 11: In Vitro Tumor Cell Killing Assay

Mammalian cells expressing the TAT419 polypeptide of interest may be obtained using standard expression vector and cloning techniques. Alternatively, many tumor cell lines expressing TAT419 polypeptides of interest are publicly available, for example, through the ATCC and can be routinely identified using standard ELISA or FACS analysis. Anti-TAT419 polypeptide monoclonal antibodies (and toxin conjugated derivatives thereof) may then be employed in assays to determine the ability of the antibody to kill TAT419 polypeptide expressing cells in vitro.

For example, cells expressing the TAT419 polypeptide of interest are obtained as described above and plated into 96 well dishes. In one analysis, the antibody/toxin conjugate (or naked antibody) is included throughout the cell incubation for a period of 4 days. In a second independent analysis, the cells are incubated for 1 hour with the antibody/toxin conjugate (or naked antibody) and then washed and incubated in the absence of antibody/toxin conjugate for a period of 4 days. In yet another independent analysis, cells genetically engineered to express TAT419 polypeptide on their cell surface (and control cells that do not express TAT419 polypeptide) can be treated with toxin-conjugated anti-TAT419 antibody, and comparisons made. Cell viability is then measured using the CellTiter-Glo Luminescent Cell Viability Assay from Promega (Cat# G7571). Untreated cells serve as a negative control.

In a first experiment and with specific regard to the present invention, various concentrations of ADC MC-vc-PAB-MMAE toxin conjugates of certain anti-TAT419 antibodies (including the murine 5E9 murine monoclonal and the hu5E9.v1 and hu5E9.v2 humanzied versions thereof) were tested for the ability to bind to and kill the TAT419 polypeptide-expressing melanoma cell lines 526mel, 537mel, 888mel, 928mel, 1300mel, A375, A2058, COL0829, G361, Hs-294-T, Malme3m, SK23, SKmel5, SKmel5-RC, SKmel28, WM-266-4, UACC257, and UACC257-NCI60. More specifically, TAT419-expressing cells were treated in vitro either with PBS (as a negative control), an MC-vc-PAB-MMAE toxin conjugate of a control antibody that does not bind to TAT419 polypeptide (as a negative control), or an anti-TAT419-MC-vc-PAB-MMAE toxin conjugated antibody. The results of these analyses demonstrated that all of the toxin-conjugated anti-TAT419 antibodies tested (including 5E9, hu5E9.v1 and hu5E9.v2) were capable of inducing significant, TAT419 target-specific cell killing of cells that express TAT419 polypeptide on the surface, whereas no specific cell killing was observed with either of the negative controls.

As a specific illustrative example of the results from this study, UACC257X2.2 cells (which express TAT419 polypeptide on their cell surface) were treated in vitro with various concentrations of either with PBS (as a negative control), an MC-vc-PAB-MMAE toxin conjugate of a control antibody that does not bind to TAT419 polypeptide (Ctrl-vc-MMAE), or an 5E9-MC-vc-PAB-MMAE toxin conjugated antibody (5E9-vc-MMAE) as described above. The data from these analyses are shown in FIG. 8 and demonstrate that the 5E9-vc-MMAE toxin conjugated antibody is capable of killing cells that express TAT419 of the surface of those cells. Comparative data obtained with different cell lines that express different amounts of TAT419 polypeptide on the cell surface demonstrates that the efficiency of cell killing is proporational to the amount of TAT419 expression on the cell surface.

These data demonstrate that the various anti-TAT419 antibodies employed in these assays (including 5E9, hu5E9.v1 and hu5E9.v2) are capable of binding to TAT419 polypeptide on the cell surface and inducing the death of those cells to which the antibody binds.

Example 12: In Vivo Tumor Cell Killing Assay Intraperitoneal Human Xenograft Tumor Model The in vivo potency of antibody-drug conjugates can be measured by treatment of NCR nude mice having human tumors implanted (so called xenografts). These studies used human melanoma cell lines and human tumors propagated in mice though implantation of the tumor samples. In the study 10 mice per group, that each have a melanoma tumor (approximately 100-200 mm$^3$), are treated IV through tail vein, with a dose of 3 mg/kg, and again at 3 weeks. Measurements of tumors carried out throughout the test period, followed by a collection of tumor samples that are then formalin fixed or snap-frozen for "TaqMan®" analysis as well as histological examination.

The human melanoma cell lines and tumors established by serial passage in nude mice are implanted i.p., and growth measured during the study. Once the tumors reach a suitable size, treatment groups of mice are dosed with antibody-drug conjugates. Xenograft tumor growth retardation is a characteristic of efficacy relative to vehicle control or control antibody. Overall, these results demonstrate specificity and efficacy of anti-TAT419 drug conjugates in in vivo tumor growth models. Tumor volume is measured in each mouse on days 0, 2, 7, 10, 13, 17, 20, 24 and 27 post-injection to determine the efficacy of each treatment in reducing tumor volume. Additionally, % animal survival is determined daily through ~30 days post treatment.

The results of these in vivo analyses demonstrate that mice treated with vehicle alone or with the non-TAT419-specific toxin-conjugated antibody show little observable reduction in tumor progression subsequent to treatment. Such results demonstrate that antibodies that do not bindi to TAT419 polypeptide, even if toxin-conjugated, provide no specific (or non-specific) therapeutic effect. In contrast, the majority of animals in the test groups evidenced a significant and apparent reproducible reduction in tumor progression post-treatment, when treated with vc-MMAE-conjugated anti-TAT419 antibodies (including 5E9, hu5E9.v1 and hu5E9.v2) demonstrating that anti-TAT419 antibody drug conjugates provide a specific in vivo therapeutic effect with animals that have tumors that express TAT419 polypeptide.

Figure 9:
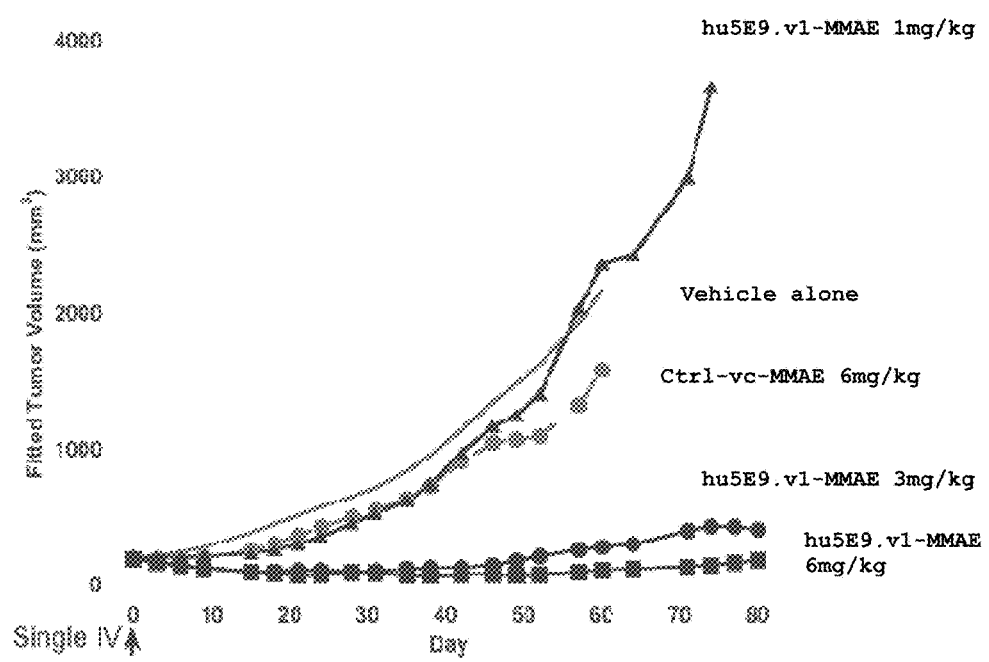
FIG. 9 shows the in vivo therapeutic efficacy of treatment with various concentrations of hu5E9.v1-vc-MMAE (hu5E9.v1-MMAE), vehicle alone (vehicle), or an MMAE-conjugated control antibody that does not bind to TAT419 polypeptide (Ctrl-vc-MMAE) against UACC257X2.2 xenografts in nude mice.

More specifically, FIG. 9 shows the data obtained from one such experiment wherein the in vivo therapeutic efficacy of a vc-MMAE conjugate of the hu5E9.v1 humanized antibody was analyzed. Xenografts derived from the UACC257X2.2 human melanoma cell line (cells which express TAT419 polypeptide on the cell surface) were propagated in nude mice as described above, and the mice were then subsequently treated as described above with vehicle alone, an MMAE-conjugated control antibody that does not bind to TAT419 polypeptide, or various amounts of hu5E9.v1-vc-MMAE. The data from these analyses demonstrate that the hu5E9.v1-vc-MMAE toxin conjugated antibody is capable of killing cells that express TAT419 of the surface of those cells. Other data demonstrated that other toxin-conjugated anti-TAT419 antibodies (including 5E9 and hu5E9.v2) were also capable of inhibiting the growth of xenograft tumors in nude mice derived from a variety of different TAT419-expressing melanoma cell lines, in a target-specific and dose-dependent manner.

Such data clearly demonstrate that anti-TAT419 antibody-drug conjugates provide a specific, significant and reproducible in vivo therapeutic effect for the treatment of tumors that express the TAT419 polypeptide.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. A method of therapeutically treating a mammal having a cancerous tumor comprising cells that express a TAT419 polypeptide, said method comprising administering to said mammal a therapeutically effective amount of a conjugated anti-TAT419 antibody, wherein the antibody comprises:
   (a) a CDR-L1 sequence of SEQ ID NO:7;
   (b) a CDR-L2 sequence of SEQ ID NO:8;
   (c) a CDR-L3 sequence of SEQ ID NO:9;
   (d) a CDR-H1 sequence of SEQ ID NO: 10;
   (e) a CDR-H2 sequence of SEQ ID NO: 11; and
   (f) a CDR-H3 sequence of SEQ ID NO: 12, thereby effectively treating said mammal.

2. The method of claim 1, wherein the mammal is human.

3. The method of claim 1, wherein the cancerous tumor is melanoma.

4. The method of claim 1, wherein the antibody is a chimeric or a humanized antibody.

5. The method of claim 1, wherein the antibody is conjugated to a cytotoxic agent.

6. The method of claim 5, wherein the cytotoxic agent is a toxin.

7. The method of claim 6, wherein the toxin is selected from the group consisting of maytansinoid, calicheamicin and auristatin.

8. The method of claim 7, wherein the auristatin is monomethyl auristatin E (MMAE).

9. The method of claim 1, wherein the antibody comprises a VL sequence of SEQ ID NO: 13 and a VH sequence of SEQ ID NO: 14.

10. The method of claim 1, wherein the antibody comprises a VL sequence of SEQ ID NO: 15 and a VH sequence of SEQ ID NO: 16.

11. The method of claim 1, wherein said TAT419 polypeptide comprises the amino acid sequence of SEQ ID NO:2 or an extracellular domain thereof.

* * * * *